United States Patent [19]

Hamanaka et al.

[11] 3,951,952

[45] Apr. 20, 1976

[54] BROAD SPECTRUM ANTIBIOTICS

[75] Inventors: Ernest S. Hamanaka, Groton; John G. Stam, Lyme, both of Conn.

[73] Assignee: Pfizer Inc., New York, N.Y.

[22] Filed: Dec. 14, 1973

[21] Appl. No.: 424,891

Related U.S. Application Data

[63] Continuation-in-part of Ser. No. 277,064, Aug. 2, 1972, abandoned.

[52] U.S. Cl............................... 260/239.1; 424/271
[51] Int. Cl.² ......................................... C07D 499/68
[58] Field of Search ................................. 260/239.1

[56] References Cited

UNITED STATES PATENTS

| | | | |
|---|---|---|---|
| 3,579,501 | 5/1971 | McGregor | 260/239.1 |
| 3,634,405 | 1/1972 | Holdrege | 260/239.1 |
| 3,870,709 | 3/1975 | Hamanaka | 260/239.1 |

*Primary Examiner*—R. J. Gallagher
*Assistant Examiner*—Jose Tovar
*Attorney, Agent, or Firm*—Connolly and Hutz

[57] ABSTRACT

6-[α-(Amidino- and imidoylaminoalkanoylamino)aracylamino]-penicillanic acids and synthetic methods for the preparation thereof.

8 Claims, No Drawings

BROAD SPECTRUM ANTIBIOTICS

CROSS-REFERENCE TO RELATED APPLICATIONS

This application is a continuation-in-part of co-pending application Ser. No. 277,064, filed Aug. 2, 1972 and now abandoned.

BACKGROUND OF THE INVENTION

This invention relates to a series of penicillins and in particular to 6-[2-aryl-2-(amidino- and imodoylaminoalkanoylamino)acetamido]penicillanic acids and to the pharmaceutically acceptable salts thereof, possessing high antibacterial activity, especially against gram-negative micro-organisms.

The compounds in the group belonging to the family of penicillins differ from each other in the nature of the R variable and possess the general formula indicated below wherein the acyl moiety on the 6-aminopenicillanic acid

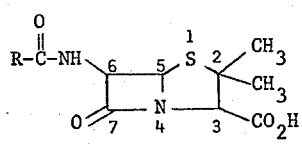

is derived from a carboxylic acid or functional derivative thereof such as an acyl halide or anhydride.

The pharmacodynamic properties and antibiotic profile of a given penicillin are determined to a large extent by the nature of the R group. The most widely used penicillins are those wherein the R moiety is represented by benzyl-, phenoxymethyl- or α-phenoxyethyl-. While these well-known analogs are highly antagonistic toward gram-positive micro-organisms they have limited gram-negative activity. Consequently, drugs which will combat a rise in gram-negative infections, e.g., *E. coli*, *Pseudomonas* or *Klebsiella*, are of value to the medical profession.

Recent efforts to improve the profile of activity within the family of penicillins has resulted in the synthesis of several new agents. α-Carboxybenzylpenicillin (U.S. Pat. No. 3,142,673), a broad spectrum antibiotic, is reported to have greater efficacy against gram-negative bacteria via the parenteral route of administration, but has limited utility via oral administration. α-Aminoarylmethylpenicillins and congeners thereof (U.S. Pat. Nos. 2,985,648; 3,140,282; 3,373,156; 3,308,023 and 3,342,677) are known, but have a limited spectrum of activity against certain gram-negative miro-organisms. Both gram-negative and gram-positive activity are claimed for 6-ureidopenicillanic acid derivatives in U.S. Pat. Nos. 3,180,863; 3,120,512 and 3,118,877 and for α-ureidopenicillins in U.S. Pat. No. 3,352,851. Activity against gram-negative bacteria, especially those of the genus Pseudomonas, is claimed for α-carbamylureidopenicillins (U.S. Pat. No. 3,483,118) and α-alkoxycarbonylureidopenicillins (U.S. Pat. No. 3,481,922). More recently, α-guanylureidopenicillins (U.S. Pat. No. 3,579,501) and α-imidoylureidopenicillins (U.S. Pat. No. 3,634,405) have been reported to be useful against infectious diseases, especially those caused by the Pseudomonas genus.

SUMMARY OF THE INVENTION

It has now been found that certain 6-[2-aryl-2-(amidinoalkanoylamino)acetamido]penicillanic acid and 6-[2-aryl-2-(imidoylamino alkanoylamino)acetamido]penicillanic acids and pharmaceutically acceptable salts thereof are outstandingly active against a broad spectrum of micro-organisms, especially gram-negative micro-organisms.

A preferred group of compounds and their pharmaceutically acceptable basic salts are those of the formula

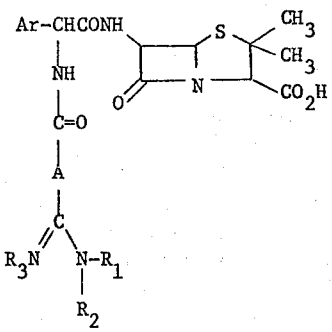

wherein Ar is phenyl, 4-hydroxyphenyl, 2-thienyl or 3-thienyl; A is alkylene containing 1 to 2 carbon atoms or alkylidene containing 2 to 3 carbon atoms; $R_1$ and $R_2$ when considered separately are each hydrogen or alkyl containing 1 to 3 carbon atoms; $R_3$ is hydrogen, alkyl containing 1 to 3 carbon atoms, naphthyl, thienyl, pyrryl, furyl, pyridyl, phenyl, benzyl or substituted phenyl or benzyl wherein said substituent is chloro, fluoro, bromo, methyl, methoxy, trifluoromethyl, 3,4-dichloro, 3,5-dibromo or 3,5-dichloro; $R_1$ and $R_2$ when considered together are alkylene containing 2 to 6 carbon atoms; and $R_2$ and $R_3$ when considered together are alkylene containing from 2 to 4 carbon atoms.

A second preferred class of penicillanic acid derivatives and their pharmaceutically acceptable basic salts are of the formula

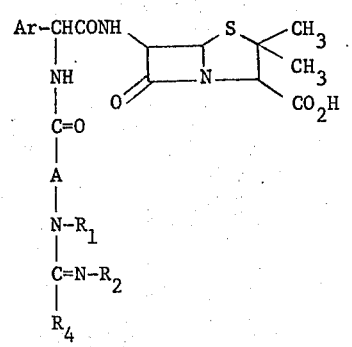

wherein Ar is phenyl, 4-hydroxyphenyl, 2-thienyl or 3-thienyl; A is methylene or alkylidene containing 2 to 3 carbon atoms; $R_1$, $R_2$ and $R_4$ when considered separately are each hydrogen or alkyl containing 1 to 3 carbon atoms; $R_1$ and $R_2$ when considered together are alkylene containing 2 to 3 carbon atoms; and $R_2$ and $R_4$ when considered together are alkylene containing 3 to 5 carbon atoms.

A third preferred class of congeners are of the formula

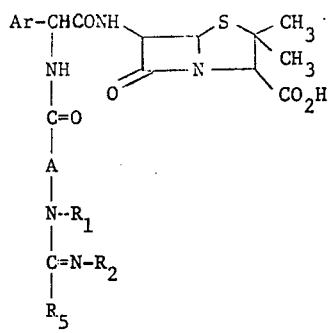

and the pharmaceutically acceptable salts thereof wherein Ar is phenyl, 4-hydroxyphenyl, 2-thienyl or 3-thienyl; A is methylene or alkylidene containing 2 to 3 carbon atoms; $R_1$ and $R_2$ are each hydrogen or alkyl containing 1 to 3 carbon atoms; and $R_5$ is naphthyl; phenyl; benzyl; monosubstituted phenyl where said substituent is fluoro, chloro, iodo, bromo, methyl, methoxy, acetyl, dimethylamino, amidino, phenyl, cyano, carboxamido, trifluoromethyl, amino, hydroxy, alkanoylamino containing 2–5 carbon atoms, methylthio, nitro, carbethoxy, methylsulfonyl, sulfamoyl, N-methylsulfamoyl or N,N-dimethylsulfamoyl; disubstituted phenyl wherein said substituent is hydroxy, alkoxy containing 1 to 5 carbon atoms, methylthio, acetoxy, methylsulfonyl, cyano, trifluoromethyl, N,N-dimethylsulfamoyl, iodo, bromo, chloro, fluoro, carbethoxy or allyloxy; trisubstituted phenyl wherein said substituent is fluoro, chloro, bromo, iodo or methoxy; or substituted benzyl wherein said substituent is chloro, fluoro, methoxy, hydroxy, dichloro, methyl or trifluoromethyl.

A fourth preferred class of compounds and their pharmaceutically acceptable basic salts are of the formula:

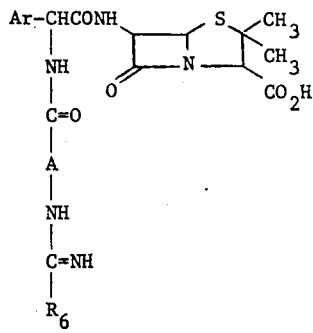

wherein Ar is phenyl, 4-hydroxyphenyl, 2-thienyl or 3-thienyl; A is methylene or alkylidene containing 2 to 3 carbon atoms; and $R_6$ is furyl; dibromo-2-furyl; thienyl; thenyl; thiazolyl; isothiazolyl; oxazolyl; isoxazolyl; 1,2,3-thiadiazolyl; 2,3-dihydro-1,4-thiazinyl; 2-benzo-γ-pyrone; 2-benzoxazolyl; 2-benzothiazolyl; 2-benzothienyl; halo substituted 2-benzothienyl; benzofuryl; mono- or di-substituted thienyl wherein said substituent is bromo, chloro, methoxy, methyl, sulfamoyl of the formula $R_7R_8NSO_2-$ wherein $R_7$ and $R_8$ are each hydrogen or alkyl containing 1 to 3 carbon atoms; or monomethyl substituted thiazolyl, isothiazolyl, oxazolyl or isoxazolyl.

A fifth preferred class of compounds are of the formula

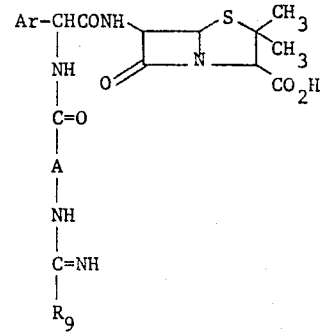

and the pharmaceutically acceptable basic or acid addition salts thereof, wherein Ar is phenyl, 4-hydroxyphenyl, 2-thienyl or 3-thienyl; A is methylene or alkylidene containing 2 to 3 carbon atoms and $R_9$ is pyridyl; pyrimidinyl; pyridazinyl; pyrazinyl; benzimidazolyl; pyrryl; 2-pyrrolinyl; picolyl; substituted pyridyl wherein said substituent is fluoro, chloro, bromo or 2,6-dichloro; or pyridyl-N-oxide.

A sixth group of preferred penicillins and the pharmaceutically acceptable basic salts thereof are of the formula

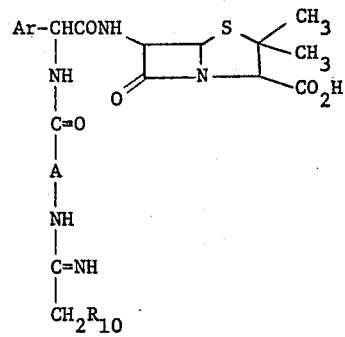

wherein Ar is phenyl, 4-hydroxyphenyl, 2-thienyl or 3-thienyl; A is methylene or alkylidene containing 2 to 3 carbon atoms; and $R_{10}$ is alkylthio containing 1 to 3 carbon atoms; alkylsulfinyl containing 1 to 3 carbon atoms; alkylsulfonyl containing 1 to 3 carbon atoms; phenylthio; benzylthio; substituted phenylthio wherein said substituent is methyl, methoxy, fluoro, chloro or bromo; alkoxy containing 1 to 3 carbon atoms; phenoxy; substituted phenoxy wherein said substituent is chloro, 3,5-dichloro or 3,4-dichloro; fluoro, chloro; hydroxy; amino; or substituted amino wherein said substituent is alkanoyl containing 2 to 4 carbon atoms, alkyl containing 1 to 3 carbon atoms, benzoyl, benzenesulfonyl, substituted benzoyl wherein said substituent is 3,4-dichloro or chloro, 2-thenoyl, phenyl or substituted phenyl wherein said substituent is chloro or 3,4-dichloro.

A seventh group of preferred congeners and their pharmaceutically acceptable basic salts are those of the formula

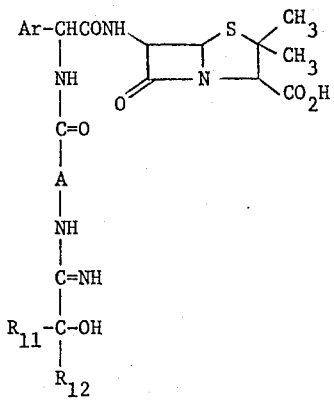

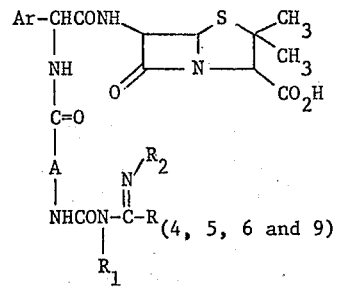

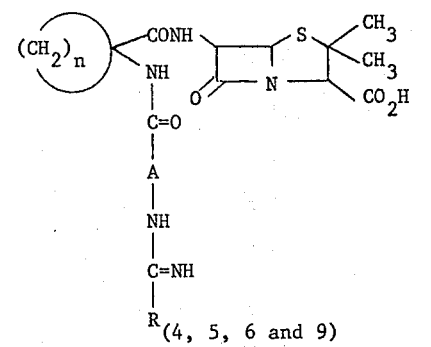

wherein Ar is phenyl, 4-hydroxyphenyl, 2-thienyl or 3-thienyl; A is methylene or alkylidene containing 2 to 3 carbon atoms; $R_{11}$ is hydrogen or alkyl containing 1 to 3 carbon atoms; and $R_{12}$ is phenyl or alkyl containing 1 to 3 carbon atoms.

In addition to the aforementioned variable definitions, the scope of the instant invention is meant to include congeners wherein Ar is 1,4-cyclohexadien-1-yl; A is 1,4- and 1,3-phenylene, bivalent heterocyclic ring, cycloalkylene, cycloalkylidene, arylene, aralkylene, alkylenearalkylene or alkylenearylene; A when taken with the nitrogen to which it is attached can form a heterocyclic ring; $R_1$ and $R_2$ when considered separately are each aroyl, cycloalkyl, alkanoyl, alkyl- and arylsulfonyl, aryl or alkyl substituted by halogen or amino; $R_1$ and $R_2$ when considered together with the nitrogen to which they are attached form a heterocyclic ring interrupted by a hetero atom selected from the group comprised of oxygen, sulphur and nitrogen, said nitrogen being optionally substituted by alkyl, substituted alkyl, aryl, acyl or sulfonyl; $R_3$ is cycloalkyl; and $R_6$ and $R_9$ are each heteroalkyl. Also included are alkyl and 1-alkanoyloxyalkyl esters of these claimed and disclosed penicillins.

Also considered within the purview of the instant invention are compounds of formulae III, IV and V of the structures:

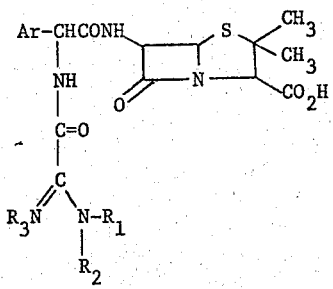

wherein Ar, A, $R_1$, $R_2$, $R_3$ and $R_{(4, 5, 6 \text{ and } 9)}$ are as previously defined and $n$ is an integer of 3 to 6.

As one skilled in the art can readily appreciate, the α-carbon atom of the penicillin side chain to which the amidino- or imidoylaminoalkanoylamino moiety is attached is an asymmetric carbon atom allowing for the existence of two optically active isomers, the D- and L-diastereoisomers, as well as the racemate, DL form. In accord with previous findings concerning the activity of such penicillins possessing asymmetric α-carbon atoms, the compounds of the present invention possessing the D-configuration are more active than those of the L-configuration and are the preferred compounds, although the L and DL forms of the instant compounds are also considered within the purview of the present invention.

Compounds of the instant application wherein A is alkylidene, derived from an α-aminoacid, have an asymmetric carbon atom allowing the D, L and DL forms. Although the unnatural form of the starting amino acid, the D-form, is the preferred, the DL and L isomers are considered within the scope of the present invention.

Further, it is noteworthy to mention while considering asymmetric centers, that there are several in the 6-aminopenicillanic acid nucleus, the basic building block from which the compounds of the present invention are derived. These potential additional isomers are not significant in this instance since the 6-aminopenicillanic acid employed leading to the product of this invention is that which is produced by fermentation and is consistently of one configuration.

DETAILED DESCRIPTION OF THE INVENTION

In accordance with the process employed for synthesizing the penicillins of the present invention three preparative routes are amenable. The first is illustrated as follows:

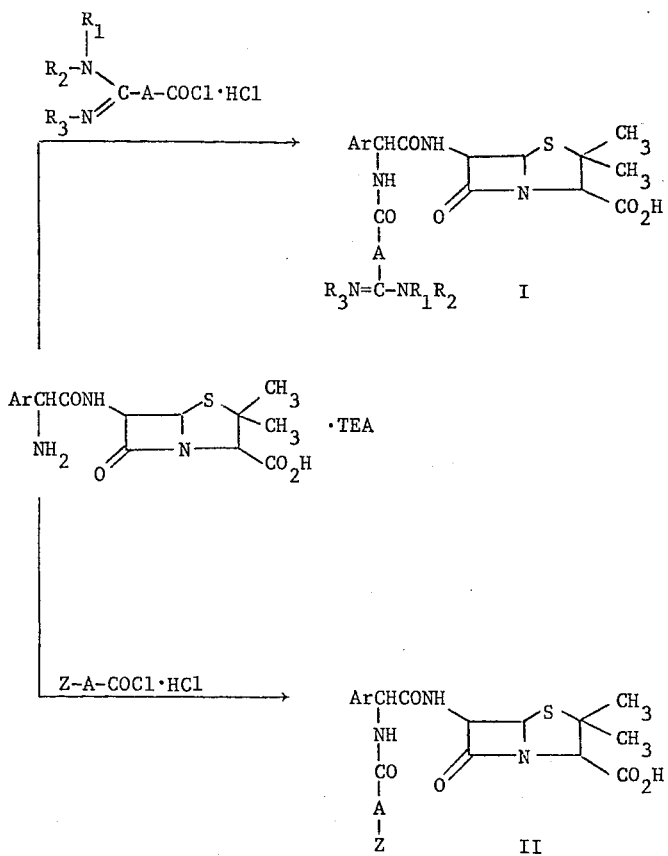

wherein $R_1$, $R_2$, $R_3$, Ar and A are as previously defined, and Z represents $R_4C(=NR_2)NR_1-$, $R_5C(=NR_2)NR_1-$, $R_6C(=NH)NH-$, $R_9C(=NH)NH-$ and $R_{10}CH_2C(=NH)NH-$ wherein $R_1$, $R_2$, $R_4$, $R_5$, $R_6$, $R_9$ and $R_{10}$ are as previously defined.

In practice, the requisite α-aminoarylmethylpenicillin triethylamine (TEA) salt and acid chloride hydrochloride, wherein Ar, A, $R_1$, $R_2$, $R_3$, $R_4$ and Z are as previously indicated, are contacted in a reaction-inert, aprotic solvent in the presence of a hydrogen halide scavenger, such as a tertiary amine, at −30° to 0°C. Generally, it is advantageous to employ an excess of the acid chloride as large as 100–200%. Under these conditions it is necessary to add a sufficient amount of a tertiary amine, preferably triethylamine, to neutralize the hydrogen chloride of the acid chloride as well as the hydrogen chloride which is generated by the interaction of the acid chloride with the α-amino group of the appropriate penicillin.

The reaction-inert solvent comprising the liquid phase of said reaction mixture should be one which does not react to any appreciable extent with either the reactants or product of said reaction. The preferred solvents should be anhydrous, aprotic, polar solvents such as dimethylformamide or hexamethylphosphoramide.

Although the initial contacting of the reactant is carried out at cold temperatures, in order to reduce the incidence of by-products, it is frequently desirable after a few minutes of mixing to allow the reaction mixture to warm to room temperature until the reaction is complete or nearly complete. The reaction time, which will vary depending on temperature, concentration and inherent reactivity of the starting reagents, is usually from 0.5 to 12 hours.

On completion of the above-mentioned reaction, any insolubles are filtered and the product is precipitated by adding the filtrate to a large volume of diethyl ether, or some other solvent in which the product is insoluble. The crude product is isolated by suction filtration and drying. A suspension of the crude product in methylene chloride is rendered free of any trace amounts of starting α-aminoarylmethylpenicillin by the addition of a small amount of triethylamine, which converts the starting penicillin to the methylene chloride soluble triethylamine salt. The pure product is subsequently filtered and dried.

The starting reagents leading to the products of the present invention are easily prepared by methods familiar to those skilled in the art. The α-aminoarylmethylpenicillins are known and described in U.S. Pat. Nos. 2,985,648 and 3,342,677 and by Long, et al., J. Chem. Soc., 1920 (1971), while the acid chloride hydrochlorides are readily synthesized from the corresponding acids employing thionyl chloride or phosphorous pentachloride. The corresponding acids are, in turn, prepared by synthetic methods well known to those skilled in the art. Noteworthy in this regard are the preparations as taught by Ried, et al., Ann., 661, 76 (1963), Ried, et al., Chem. Ber., 95, 728 (1962), McElvain, et al., J. Am. Chem. Soc., 71, 40 (1949), Bauer, et al., J. Org. Chem., 27, 4382 (1962) and Cardellini, et al., Ann. Chim. (Rome), 58, 183, 1199 (1958).

The second synthetic procedure employed in the preparation of the compounds of the instant invention is illustrated as follows:

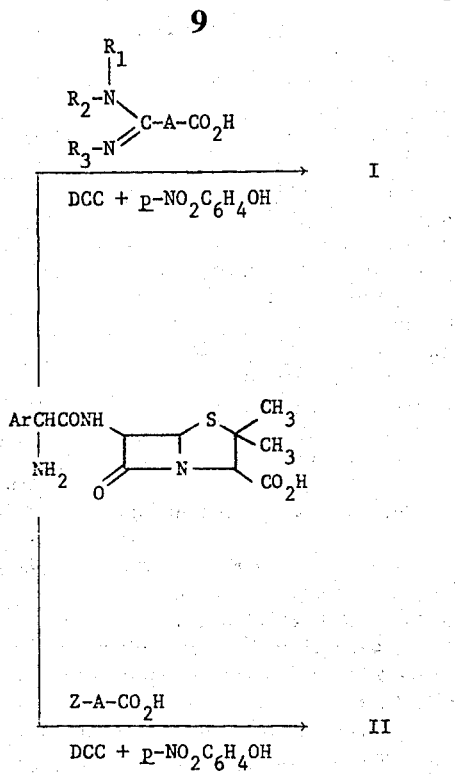

wherein Z, Ar, A, $R_1$, $R_2$, $R_3$, $R_4$, $R_5$, $R_6$ and $R_{10}$ are as previously indicated.

In accordance with the above outlined synthetic scheme, equimolar amounts of the requisite alkanoic acid hydrochloride, p-nitrophenol and dicyclohexylcarbodiimide (DCC), are contacted in a reaction-inert solvent, such as those indicated in the previously discussed preparative procedure, at ambient temperatures. After 1 to 3 hrs., the intermediate p-nitrophenyl ester, generated in situ, is treated with an equimolar amount, or a slightly lesser amount, of the appropriate α-aminoarylmethylpenicillin, preferably as a basic tertiary amine salt. The reaction time can vary from 1 to 6 hrs. depending on the temperature, concentration and reactivity of the reagents employed.

The product is isolated, after filtration of the reaction mixture, by addition of the reaction filtrate to a large volume of diethyl ether. The product can be purified, when required, by employing triethylamine as mentioned in the previously discussed preparative method.

The third synthetic procedure, one which allows the synthesis of compounds of formula II, is illustrated as follows:

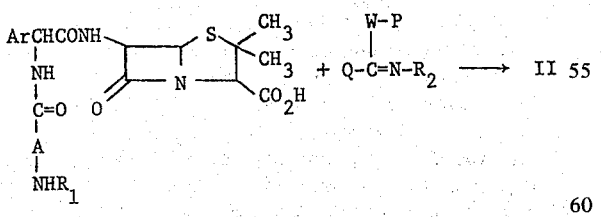

wherein Ar, A, R and $R_2$ are as previously defined, P is lower alkyl, Q is $R_4$, $R_5$, $R_6$, $R_9$, $R_{10}CH_2$ or $R_{11}R_{12}C(OH)$—, and W is —O— or —S—.

Experimentally, the aforedescribed reaction between an imino ether and a 6-(α-aminoalkanoylamino)aracylaminopenicillanic acid leading to the compounds of formula II is carried out between equimolar amounts of said reactants plus as much as a 5–20% excess of the appropriate imino ether. Further, it is desired, although not absolutely necessary, to conduct the condensation in a reaction-inert solvent. The preferred solvents should be anhydrous, aprotic, polar solvents such as dimethylformamide or hexamethylphosphoramide.

The order of addition is not critical, and the reactants can be combined together in the same solvent or the predissolved reactants can be combined. It is preferred to cool the solvent or the solutions of individual reactants before combining to minimize any side reactions which may occur when one reactant is present in large excess during the initial phase of combining. Once the reactants are combined the cooling bath is removed and the reaction subsequently allowed to warm to room temperature.

Reaction time is not critical and is influenced by reaction temperature, concentration and inherent reactivity of the starting reagents. When ambient temperatures are employed, reaction time is generally 1–8 hours.

At the completion of the reaction period, the mixture or solution is poured into a miscible solvent, such as diethyl ether, in which the desired product II is insoluble. The precipitated product is separated by filtration, washed successively with ether, acetone or methylene chloride and dried in vacuo.

As one skilled in the art can recognize, the amidino and imidoylamino moieties of the instantly claimed compounds can exist in several different tautomeric forms, all of which are considered within the purview of the present invention.

As has been previously noted, a characteristic feature of the acidic compounds of the instant invention is their ability to form basic salts. Acid congeners of the present invention are converted to basic salts by the interaction of said acid with an appropriate base in an aqueous or nonaqueous medium. Such basic reagents suitably employed in the preparation of said salts can vary in nature, and are meant to contemplate such bases as organic amines, ammonia, alkali metal hydroxides, carbonates, bicarbonates, hydrides and alkoxides, as well as alkali earth metal hydroxides, hydrides, alkoxides and carbonates. Representative of such bases are ammonia, primary amines such as n-propylamine, n-butylamine, aniline, cyclohexylamine, benzylamine, p-toluidine, ethylamine, octylamine, secondary amines such as dicyclohexylamine and tertiary amines such as diethylaniline, N-methylpyrrolidine, N-methylmorpholine and 1,5-diazabicyclo-[4,3,0]-5-nonene; sodium hydroxide, potassium hydroxide, ammonium hydroxide, sodium ethoxide, potassium methoxide, magnesium hydroxide, calcium hydride and barium hydroxide.

As one skilled in the art can readily appreciate, the compounds of the instant invention are sufficiently basic, by virtue of the amidino and imidoylamino moieties, to form acid addition salts; said salts, especially the pharmaceutically acceptable acid addition salts, are also considered within the scope of this invention.

In the utilization of the chemotherapeutic activity of those compounds of the present invention which form basic salts, it is preferred, of course, to use pharmaceutically acceptable salts. Although water insolubility, high toxicity, or lack of crystalline nature may make some salt species unsuitable or less desirable for use as such in a given pharmaceutical application, the water insoluble or toxic salts can be converted to the corresponding acids by decomposition of the salts, or alternately they can be converted to any desired pharmaceutically acceptable basic salt. The salt pharmaceutically acceptable salts preferred include the sodium, aluminum, potassium, calcium, magnesium, ammonium and substitued ammonium salts, e.g., procaine, dibenzylamine, N,N-bis(dehydroabietyl)ethylenediamine, 1-ephenamine, N-ethylpiperidine, N-benzyl-β-phenethylamine, N,N'-dibenzylethylenediamine, triethylamine, as well as salts with other amines which have been used to form salts with benzylpenicillin.

The novel penicillins described herein exhibit in vitro activity against a wide variety of micro-organisms, including both gram-positive and gram-negative bacteria. Their useful activity can readily be demonstrated by in vitro tests against various organisms in a brain-heart infusion medium by the usual two-fold serial dilution technique. The in vitro activity of the herein described compounds renders them useful for topical application in the form of ointments, creams and the like, or for sterilization purposes, e.g., sick-room utensils.

These novel penicillins are also effective antibacterial agents in vivo in animals, including man, not only via the parenteral route of administration buty also by the oral route of administration.

Obviously, the physician will utimately determine the dosage which will be most suitable for a particular individual person, and it will vary with the age, weight and response of the particular patient as well as with the nature and extent of the symptoms, the nature of the bacterial infection being treated and the pharmacodynamic characteristics of the particular agent to be administered. It will often be found that when the composition is administered orally, larger quantities of the active ingredient will be required to produce the same level as produced by a small quantity administered parenterally.

Having full regard for the foregoing factors it is considered that an effective daily oral dose of the compounds of the present invention in humans of approximately 10–100 mg./kg. per day, with a preferred range of about 50–75 mg./kg. per day in single or divided doses, and a parenteral dose of 25–100 mg./kg. per day, with a preferred range of about 20–75 mg./kg. per day will effectively alleviate the symptons of the infection. These values are illustrative, and there may, of course, be individual cases where higher or lower dose ranges are merited.

As has been previously mentioned, the penicillins of the present invention are broad spectrum antibiotics which are, unlike many penicillin analogs, highly antagonistic toward gram-negative microorganisms, in particular *E. coli*, *Pseudomonas* and *Klebsiella*. Further, they appear to be more resistant than most penicillins to destruction by penicillinase, an enzyme produced by certain bacteria which degrades penicillin to an inactive penicillanic acid.

The preferred compounds of the present invention are 6-[2-phenyl-2-(amidinoacetamido)acetamido]-penicillanic acid, 6-[2-phenyl-2-(3-amidinopropionamido)acetamido]penicillanic acid, 6-[2-phenyl-2-(2-imidazolinylacetamido)acetamido]penicillanic acid, 6-[2-phenyl-2-(3-[2-imidazolinyl)propionamido)acetamido]penicillanic acid, 6-[2-phenyl-2-(formimidoylaminoacetamido)acetamido]penicillanic acid, 6-[2-phenyl-2-(acetimidoylaminoacetamido)acetamido]penicillanic acid, 6-[2-phenyl-2-(propionimidoylaminoacetamido)acetamido]penicillanic acid, 6-[2-phenyl-2-(butyrimidoylaminoacetamido)acetamido]penicillanic acid, 6-[2-phenyl-2-(isobutyrimidoylaminoacetamido)acetamido penicillanic acid, 6-[2-phenyl-2-(benzimidoylaminoacetamido)acetamido]penicillanic acid, 6-[2-phenyl-2-(p-chlorobenzimidoylaminoacetamido)acetamido]penicillanic acid, 6-[2-phenyl-2-(p-fluorobenzimidoylaminoacetamido)acetamido]penicillanic acid, 6-[2-phenyl-2-(p-bromobenzimidoylaminoacetamido)acetamido]penicillanic acid, 6-[2-phenyl-2-(2-furoimidoylaminoacetamido)acetamido]penicillanic acid, 6-[2-phenyl-2-(2-thenoimidoylaminoacetamido)acetamido]penicillanic acid, 6-[2-phenyl-2-(3,4-dichlorobenzimidoylaminoacetamido)acetamido]penicillanic acid, 6-[2-phenyl-2-(3,5-dichlorobenzimidoylaminoacetamido)acetamido]penicillanic acid 6-[2-phenyl-2-(3-cyano-5-chlorobenzimidoylaminoacetamido)acetamido]pencillanic acid, 6-[2-phenyl-2-(3-cyano-5-bromobenzimidoylaminoacetamido)acetamido]penicillanic acid, 6-[2-phenyl-2-(3,5-difluorobenzimidoylaminoacetamido)acetamido]penicillanic acid, 6-[2-phenyl-2-(3,5-diiodoenzimidoylaminoacetamido)acetamido]penicillanic acid, 6-[2-phenyl-2-(3,5-dicyanobenzimidoylaminoacetamido)acetamido]penicillanic acid, 6-[2-phenyl-2-(3,4,5-triidobenzimidoylaminoacetamido)acetamido]pencillanic acid, 6-[2-phenyl-2-(m-chlorobenzimidoylaminoacetamido)acetamido]penicillanic acid, 6-[2-phenyl-2-(m-cyanobenzimidoylaminoacetamido)acetamido]penicillanic acid, 6-[2-phenyl-2-(2-pyrrylimidoyl-)aminoacetamido)acetamido]penicillanic acid, 6-[2-phenyl-2-(3,4-dibromobenzimidoylaminoacetamido)acetamido]penicillanic acid, 6-[2-phenyl-2-(3,5-dibromobenzimidoylaminoacetamido)acetamido]penicillanic acid, 6-[2-phenyl-2-(3,5-bis{trifluoromethyl}benzimidoylaminoacetamido)acetamido]pencillanic acid, 6-[2-phenyl-2-(3,5-bis{methylthio}benzimidoylaminoacetamido)acetamido]pencillanic acid, 6-[2-phenyl-2-(3,5-methylsulfonyl)benzimidoylaminoacetamido)acetamido]penicillanic acid, 6-[2-phenyl-2-(3,5-bis{N,N-dimethylsulfamoyl}benzimidoylaminoacetamido)acetamido]penicillanic acid, 6-[2-phenyl-2-(3,4,5-tribromobenzimidoylaminoacetamido)acetamido]penicillanic acid, 6-[2-phenyl-2-(3,5-dichloro-4-bromobenzimidoylaminoactamido)acetamido]penicillanic acid, 6-[2-phenyl-2-(3,4,5-trichlorobenzimidoylaminoacetamido)acetamido]penicillanic acid, 6-[2-phenyl-2-(3,5-dibromo-4-chlorobenzimidoylaminoacetamido)acetamido]penicillanic acid, 6-[2-phenyl-2-(3,5-dibromo-4-fluorobenzimidoylaminoacetamido)acetamido]penicillanic acid, 6-[2-phenyl-2-(4,5-dibromo-2-thenoimidoylaminoacetamido)acetamido]penicillanic acid, 6-[2-phenyl-2-(5-bromo2-thenoimidoylaminoacetamido)acetamido]penicillanic acid, 6-[2-phenyl-2-(4-pyridylimidoylaminoacetamido)acetamido]penicillanic acid, 6-[2-phenyl-2-(3-pyridylimidoylaminoacetamido)acetamido]pencillanic acid, 6 -[2-phenyl-2-(1-oxo-4-pyridylimidoylaminoacetamido)acetamido]penicillanic acid, 6-[2-phenyl-2-(2,6-dichloro-4-pyridylimidoylaminoacetamido)acetamido]penicillanic acid, 6-[2-phenyl-2-(2-benzimidazoylimidoylaminoacetamido)acetamido]penicillanic acid, 6-[2-phenyl-2-(methylthioacetimidoylaminoacetamido)acetamido]penicillanic acid, 6-[2-phenyl-2-(methoxyacetimidoylaminoacetamido)acetamido]penicillanic acid, and 6-[2-phenyl-2-(α-hydroxyphenylacetimidoylaminoacetamido)acetamido]-penicillanic acid. Further preferred within this group of outstanding compounds are those diasterioisomers of the D-configuration.

The antimicrobial spectra of a number of compounds of the instant invention are provided in the following tables. Table I compares the in vitro profile of 6-[D-2-phenyl-2-(amidinopropionamido)acetamido]penicillanic acid (PAP) with ampicillin (AMP) and carbenicillin (CAR). The tests were run under standardized conditions in which nutrient broth containing various concentrations of the test material was seeded with the particular organism specified, and the minimum concentration (MIC) at which growth of each organism failed to occur was observed and recorded.

TABLE I

In vitro Comparison Data for PAP, AMP, and CAR (MIC; mcg./ml.)

| Organism | PAP | AMP | CAR |
|---|---|---|---|
| E. coli 51A266 | 1.56 | 3.12 | 3.12 |
| E. coli 51A002 | 200 | 200 | 200 |
| Ps. aeruginosa 52A490 | 1.56 | 0.78 | 0.6 |
| Ps. aeruginosa 52A104 | 12.5 | 200 | 50 |
| Ps. aeruginosa 52A173 | 0.78 | 38 | 75 |
| Kleb. pneumoniae 53A009 | 25 | 100 | 200 |
| Kleb. pneumoniae 53A015 | >200 | 250 | >200 |
| A. aerogenes 55A002 | 100 | 100 | 25 |
| A. aerogenes 55A004 | 6.25 | 5 | 50 |
| Ser. marcescens 63A001 | 3.12 | 200 | 25 |
| P. mirabilis 57C015 | 6.25 | 1.56 | 1.25 |
| P. vulgaris 57A059 | 1.56 | 6 | 12.5 |
| S. aureus | — | 0.09 | 1.56 |

Table II presents the in vivo comparison data for the three compounds contained in Table I aganst several experimental infections in mice.

The values (% survivors) are obtained under standard conditions known to those skilled in the art. For the E. coli organism, the test compound is administered to the infected mice by a multiple dosing regimen in which the first dose is given 0.5 hour after inoculation and is repeated 4 and 24 hours later.

TABLE II

| Organism | Route* | Dose (mg./kg.) | % Protection+ PAP | AMP | CAR |
|---|---|---|---|---|---|
| E. coli 51A266 | PO | 200 | 30 | 90 | 70 |
|  |  | 50 | 20 | 80 | 10 |
| E. coli 51A266 | SC | 200 | 80 | 90 | 90 |
|  |  | 50 | 80 | 80 | 90 |

*PO = oral  
SC = subcutaneous } route of administration  
+% survivors

Table III presents additional in vitro data for related compounds of the instant invention.

TABLE III

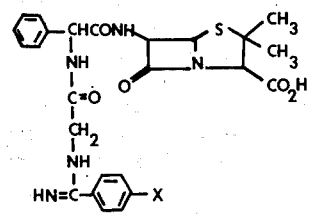

| Organism | MIC (mcg./ml.) | | | |
|---|---|---|---|---|
|  | X = H | X = F | X = Cl | X = Br |
| S. aureus 01A005 | 0.78 | 0.39 | 0.39 | 0.39 |
| Ps. aeruginosa 52A104 | 25 | 12.5 | 25 | 25 |
| Ps. aeruginosa 52A490 | 12.5 | 3.12 | 12.5 | 6.25 |
| Kleb. pneumoniae 53A009 | 100 | 25 | 12.5 | 12.5 |
| A. aerogenes | 25 | 25 | 3.12 | 3.12 |
| P. mirabilis 57C015 | 12.5 | 3.12 | 3.12 | 3.12 |
| Ser. marcescens 63A001 | 12.5 | 6.25 | 6.25 | 6.25 |
| E. coli 51A266 | 12.5 | 1.56 | 0.78 | 0.39 |

Table IV presents in vivo comparison data for the four compounds in Table III against E. coli infections in mice.

The values, reported as % survivors, are obtained under standard conditions familiar to those skilled in the art. The test compound is administered to the infected mice by a multiple dosing regimen in which the first dose is given 0.5 hour after inoculation and is repeated 4 and 24 hours later.

TABLE IV

| Organism | Route | Dose (mg./kg.) | % Survivors | | | |
|---|---|---|---|---|---|---|
|  |  |  | X=H | X=F | X=Cl | X=Br |
| E. coli 51A266 | PO | 200 | 10 | 10 | 0 | 0 |
|  |  | 50 | 0 | 0 | 0 | 0 |
|  |  | 25 | 0 | 10 | 0 | 10 |
| E. coli 51A266 | SC | 200 | 90 | 90 | 70 | 90 |
|  |  | 50 | 70 | 70 | 60 | 60 |
|  |  | 25 | 10 | 50 | 50 | 50 |

The novel products of this invention are of value as antibacterial agents and are remarkably effective in treating a number of infections caused by susceptible gram-negative and gram-positive bacteria in poultry and animals including man. For such purposes, the pure materials or mixtures thereof with other antibiotics can be employed. They may be administered alone or in combination with a pharmaceutical carrier on the basis of the chosen route of administration and standard pharmaceutical practice. For example, they may be administered orally in the form of tablets containing such excipients as starch, milk sugar, certain types of clay, etc., or in capsules alone or in admixture with the same or equivalent excipients. They may also be administered orally in the form of elixirs or oral suspensions which may contain flavoring or coloring agents, or be injected parenterally, that is, intramuscularly or subcutaneously. For parenteral administration, they are best used in the form of a sterile aqueous solution which may be either aqueous such as water, isotonic saline, isotonic dextrose, Ringer's solution, or non-aqueous such as fatty oils of vegetable origin (cotton seed, peanut oil, corn, sesame) and other non-aqueous vehicles which will not interfere with the therapeutic efficiency of the preparation and are nontoxic in the volume or proportion used (glycerol, propylene glycol, sorbitol). Additonally, compositions suitable for extemporaneous preparation of solutions prior to administration may advantageously be made. Such compositions may include liquid diluents, for example, propylene glycol, diethyl carbonate, glycerol, sorbitol, etc.; buffering agents, as well as local anesthetics and inorganic salts to afford desirable pharmacological properties.

The following examples are provided solely for the purpose of illustration and are not to be construed as limitations of this invention, many variations of which are possible without departing from the spirit or scope thereof.

EXAMPLE 1

6-[D-2-Phenyl-2-(amidinoacetamido)acetamido]-penicillanic acid ($Ar = C_6H_5$; $A = -CH_2-$; $R_1$, $R_2$ and $R_3 = H$)

To 10 ml. of dry dimethylformamide at room temperature and maintained under a nitrogen atmosphere is added 810 mg. (6 m moles) of p-nitrophenol, 1.24 g. (6 m moles) of dicyclohexylcarbodiimide and 830 mg. (6 m moles) of amidinoacetic hydrochloride, and the mixture allowed to stir for 2 hrs. D-α-Aminobenzylpenicillin, triethylamine salt (1.8 g., 4 m moles) is added to the yellow suspension and the mixture allowed to stir overnight at ambient temperatures. The solids are filtered and the clear filtrate poured into 200 ml. of diethyl ether. The precipitated yellow product is filtered and suspended in 100 ml. of methylene chloride to which is added 2 ml. of triethylamine. After stirring for 1 hr. the purified product is filtered and dried in vacuo, 910 mg., (52.5% yield).

Infrared spectrum peaks (microns; KBr): 3.0(b), 3.4, 5.6, 6.0, 6.25, 6.6, 6.85, 7.15, 7.4, 8.1 and 8.85.

Nuclear magnetic resonance spectrum peaks (PPM; DMSO-$D_6$): 1.48(d,6H), 3.95(s,2H), 4.04(1H), 5.2–5.8(c,3H), 7.36(7H) and 8–9(b,3H).

EXAMPLE 2

6-[D-2-Phenyl-2-(3-amidinopropionamido)acetamido]penicillanic acid ($Ar = C_6H_5$; $A = -(CH_2)_2-$; $R_1$, $R_2$ and $R_3 = H$)

To a suspension of 1.35 g. (3 m moles) of D-α-aminobenzylpenicillin, triethylamine salt in 15 ml. of dry dimethylformamide maintained under nitrogen, is added 0.63 ml. (4.5 m moles) of triethylamine and the mixture cooled in an ice bath to 0° C. 3-Amidinopropionyl chloride hydrochloride (770 mg., 4.5 m moles) is added and the mixture allowed to stir for 15 min. at 0° C. and an additional hour at room temperature. The mixture is then cooled to 0° C. and an additional 237 mg. (1.5 m moles) of the acid chloride hydrochloride and 0.21 ml. (1.5 m moles) of triethylamine is added and the reaction mixture allowed to stir 1 hour at room temperature. The solids are filtered, and the filtrate added dropwise into 200 ml. of diethyl ether with stirring. The crude, dried product, 1.2 g., is suspended in 200 ml. of methylene chloride and treated with 1 ml. of triethylamine. After stirring for 30 min. the purified product is filtered and dried under reduced pressure, 640 mg. (47.4% yield).

Infrared spectrum peaks (microns; KBr): 3.0(b), 3.35, 5.6, 6.0, 6.2, 6.6, 6.85, 7.15, 7.65, 8.0, 8.15 and 8.85.

Nuclear magnetic resonance spectrum peaks (PPM; DMSO-$D_6$): 1.5(d,6H), 2.55(b,4H), 4.0(s,1H), 5.24–5.85(c,3H), 7.4(7H) and 9.0(b,3H).

EXAMPLE 3

6-[DL-2-{2-thienyl}-2-(N-methylamidino)acetamido]-penicillanic acid ($Ar = C_4H_3S$; $A = -CH_2-$; $R_1 = CH_3$; $R_2$ and $R_3 = H$)

A 150 ml. flask fitted with a nitrogen bleed is charged with a suspension of 3.55 g. (0.01 mole) of DL-α-amino-2-thienylmethylpenicillin in 70 ml. of dry dimethylformamide and 3.06 ml. (0.022 mole) of triethylamine. The reaction mixture is cooled to 0° C. and 1.88 g. (0.011 mole) of N-methylamidinoacetyl chloride hydrochloride added portionwise. The suspension is allowed to warm to room temperature and remain at this temperature for 1 hour. The mixture is then filtered and the clear filtrate added dropwise to 1.1 l. of rapidly stirred diethyl ether. The resulting suspension is stirred for an additional 30 min. and is then filtered and the solids dried in vacuo. The crude product is suspended in 100 ml. of methylene chloride to which is added 2 ml. of triethylamine. After 45 min. the purified product is suction filtered and dried under reduced pressure.

EXAMPLE 4

Starting with the appropriate D-α-aminoarylmethyl-penicillin or triethylamine salt thereof and the requisite aminoalkanoic acid or acid chloride and following the procedure of Example 1 or 2, as indicated, the following penicillins are synthesized:

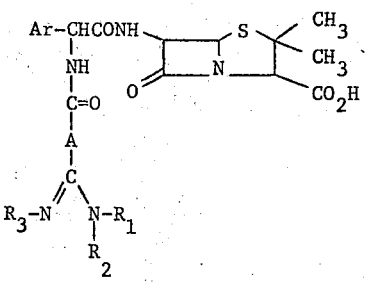

| Ar | A+ | $R_1$ | $R_2$ | $R_3$ | Procedure |
|---|---|---|---|---|---|
| $C_6H_5-$ | $-CH_2-$ | $CH_3-$ | $H-$ | $H-$ | Example 1 |
| $C_6H_5-$ | $-CH_2-$ | $H-$ | $C_2H_5-$ | $C_2H_5-$ | Example 1 |
| $C_6H_5-$ | $-CH_2-$ | $CH_3-$ | $n-C_3H_7-$ | $H-$ | Example 1 |
| $C_6H_5-$ | $-(CH_2)_2-$ | $CH_3-$ | $CH_3-$ | $CH_3-$ | Example 2 |
| $C_6H_5-$ | $-(CH_2)_2-$ | $H-$ | $i-C_3H_7-$ | $i-C_3H_7-$ | Example 1 |
| $C_6H_5-$ | $-(CH_2)_2-$ | $C_2H_5-$ | $H-$ | $H-$ | Example 2 |
| $C_6H_5-$ | $-CH_2-$ | $n-C_3H_7-$ | $H-$ | $H-$ | Example 1 |

-continued

| Ar | A+ | R₁ | R₂ | R₃ | Procedure |
|---|---|---|---|---|---|
| C₆H₅— | CH₃CH— | CH₃— | H— | H— | Example 1 |
| C₆H₅— | CH₃CH— | H— | CH₃— | CH₃— | Example 1 |
| C₆H₅— | (CH₃)₂C— | H— | H— | H— | Example 1 |
| C₆H₅— | CH₃CH₂CH— | H— | C₂H₅— | C₂H₅— | Example 2 |
| 4-HOC₆H₄— | —CH₂— | H— | H— | H— | Example 1 |
| 4-HOC₆H₄— | —CH₂— | CH₃— | H— | H— | Example 1 |
| 4-HOC₆H₄— | —CH₂— | H— | C₂H₅— | C₂H₅— | Example 1 |
| 4-HOC₆H₄— | —(CH₂)₂— | CH₃— | CH₃— | CH₃— | Example 2 |
| 4-HOC₆H₄— | —(CH₂)₂— | C₂H₅— | H— | H— | Example 2 |
| 2-C₄H₃S— | —CH₂— | H— | H— | H— | Example 1 |
| 2-C₄H₃S— | —CH₂— | CH₃— | n-C₃H₇— | H— | Example 1 |
| 2-C₄H₃S— | —CH₂— | H— | C₂H₅— | C₂H₅— | Example 1 |
| 2-C₄H₃S— | —CH₂— | n-C₃H₇— | H— | H— | Example 1 |
| 2-C₄H₃S— | —CH₂— | n-C₃H₇— | H— | H— | Example 1 |
| 2-C₄H₃S— | —CH₂— | CH₃— | CH₃— | CH₃— | Example 1 |
| 2-C₄H₃S— | —(CH₂)₂— | H— | i-C₃H₇— | i-C₃H₇— | Example 2 |
| 2-C₄H₃S— | —(CH₂)₂— | H— | H— | H— | Example 2 |
| 2-C₄H₃S— | —(CH₂)₂— | C₂H₅— | H— | H— | Example 2 |
| 2-C₄H₃S— | CH₃CH— | CH₃ | H— | H— | Example 2 |
| 2-C₄H₃S— | CH₃CH— | H— | H— | H— | Example 2 |
| 2-C₄H₃S— | CH₃CH— | H— | CH₃— | CH₃— | Example 2 |
| 2-C₄H₃S— | CH₃CH₂CH— | H— | C₂H₅— | C₂H₅— | Example 2 |
| 2-C₄H₃S— | CH₃CH₂CH— | H— | H— | H— | Example 2 |
| 2-C₄H₃S— | CH₃CH₂CH— | CH₃— | H— | H— | Example 2 |
| 3-C₄H₃S— | —CH₂— | H— | H— | H— | Example 1 |
| 3-C₄H₃S— | —CH₂— | CH₃— | H— | H— | Example 1 |
| 3-C₄H₃S— | —CH₂— | H— | C₂H₅— | C₂H₅— | Example 1 |
| 3-C₄H₃S— | —CH₂— | CH₃— | n-C₃H₇— | H— | Example 1 |
| 3-C₄H₃S— | —(CH₂)₂— | H— | H— | H— | Example 2 |
| 3-C₄H₃S— | —(CH₂)₂— | C₂H₅— | H— | H— | Example 2 |
| 3-C₄H₃S— | —(CH₂)₂— | CH₃— | CH₃— | CH₃— | Example 1 |
| 3-C₄H₃S— | CH₃CH— | H— | H— | H— | Example 2 |
| 3-C₄H₃S— | CH₃CH— | CH₃— | H— | H— | Example 2 |
| 3-C₄H₃S— | CH₃CH— | CH₃— | H— | H— | Example 2 |
| 3-C₄H₃S— | (CH₃)₂C— | H— | H— | H— | Example 1 |
| 3-C₄H₃S— | (CH₃)₂C— | CH₃— | H— | H— | Example 1 |
| 3-C₄H₃S— | (CH₃)₂C— | H— | CH₃— | CH₃— | Example 1 |
| 3-C₄H₃S— | (CH₃)₂C— | H— | H— | i-C₃H₇— | Example 2 |

⁺In this and subsequent tables, the A group representing alkylene or alkylidene is written in such a manner that the left bond of the group is attached to the O
‖
—C— group and the right bond of the group to the carbon atom of the amidino moiety.

EXAMPLE 5

Employing the procedure of Example 2, and starting with the appropriate chemical intermediates, the following congeners are prepared: 6-[D-2-phenyl-2-(N-phenylamidinoacetamido)acetamido]penicillanic acid, 6-[D-2-phenyl-2-(4-{N-p-chlorophenyl-N'-methylamidino}acetamido)acetamido]penicillanic acid, 6-[DL-2-phenyl-2-(3-{N-methyl-N'-p-bromophenylamidino}propionamido)acetamido]penicillanic acid, 6-[D-2-p-hydroxyphenyl-2-(3-{-p-methylbenzylamidino}propionamido)acetamido]-penicillanic acid, 6-[D-2-p-hydroxyphenyl-2-(2-{-ethyl-N'-m-trifluoromethyl-phenylamidino}acetamido)acetamido]penicillanic acid, 6-[D-2-p-hydroxyphenyl-2-(2-{N,N-dimethyl-N'-p-fluorobenzylamidino}propionamido)acetamido]-penicillanic acid, 6-[D-2-α-thienyl-2-(3-{N-2-pyrrylamidino}propionamido)acetamido]penicillanic acid, 6-[D-2-α-thienyl-2-(N,N-dimethyl-N'-p-methoxyphenylamidinoacetamido)acetamido]penicillanic acid, 6-[D-2-α-thienyl-2-(N-m-methyl-phenylamidinoacetamido)acetamido]penicillanic acid, 6-[D-2-β-thienyl-2-(N-n-propyl-N'-o-chlorobenzylamidinoacetamido)acetamido]penicillanic acid, 6-[D-2-β-thienyl-2-(4-{N-β-thienylamidino}acetamido)acetamido]penicillanic acid and 6-[D-2-β-thienyl-2-(N-4-pyridylamidinoacetamido)acetamido]-penicillanic acid.

EXAMPLE 6

6-[D-2-Phenyl-2-(p-amidinobenzamido)acetamido]-penicillanic acid (Ar = C₆H₅; A = 1,4—C₆H₄; R₁, R₂ and R₃ = H)

To a suspension of 806 mg. (2 m moles) of D-α-aminobenzylpenicillin trihydrate in 10 ml. of dry dimethylformamide containing 0.56 ml. of triethylamine under a nitrogen atmosphere and cooled to 0° C. in an ice bath is added dropwise 438 mg. (2 m moles) of p-amidinobenzoyl chloride hydrochloride in 10 ml. of the same solvent. The resulting solution is allowed to stir for 10 min. at 0° C. and then for 50 min. at room temperature. The precipitate which forms during the reaction is filtered and the clear filtrate added dropwise to 400 ml. of well stirred diethyl ether. The tan product is purified by suspending it in 30 ml. of methylene chloride to which is added 0.5 ml. of triethylamine. After stirring for 1.5 hrs., the product is filtered and dried in vacuo 750 mg. (75.5% yield).

EXAMPLE 7

The procedure of Example 6 is repeated, starting with the appropriate D-α-aminoarylmethylpenicillin and acid chloride hydrochloride, to provide the following analogs:

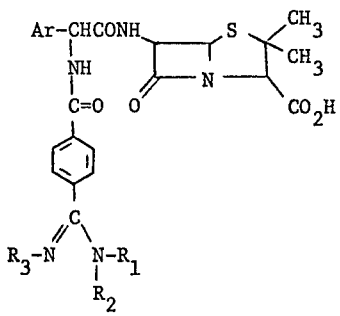

| Ar | $R_1$ | $R_2$ | $R_3$ |
|---|---|---|---|
| $C_6H_5-$ | $CH_3-$ | $H-$ | $H-$ |
| $C_6H_5-$ | $CH_3$ | $CH_3-$ | $H-$ |
| $C_6H_5-$ | $H-$ | $C_2H_5-$ | $C_2H_5-$ |
| $C_6H_5-$ | $i-C_3H_7-$ | $H-$ | $H-$ |
| $4-HOC_6H_4-$ | $H-$ | $H-$ | $H-$ |
| $4-HOC_6H_4-$ | $C_2H_5-$ | $H-$ | $H-$ |
| $4-HOC_6H_4-$ | $CH_3-$ | $CH_3-$ | $CH_3-$ |
| $2-C_4H_3S-$ | $H-$ | $H-$ | $H-$ |
| $2-C_4H_3S-$ | $CH_3-$ | $H-$ | $H-$ |
| $2-C_4H_3S-$ | $H-$ | $C_2H_5-$ | $C_2H_5-$ |
| $2-C_4H_3S-$ | $CH_3-$ | $CH_3-$ | $CH_3-$ |
| $3-C_4H_3S-$ | $H-$ | $H-$ | $H-$ |
| $3-C_4H_3S-$ | $CH_3-$ | $CH_3-$ | $CH_3-$ |

EXAMPLE 8

6-[D-2-Phenyl-2-(2-imidazolinylacetamido)acetamido]penicillanic acid (Ar = $C_6H_5$; A = $CH_2$; $R_1$ = H, $R_2$ and $R_3$ together = $-CH_2CH_2-$)

Employing the procedure of Example I, 825 mg. (5 m moles) of 2imidazolinylacetic acid hydrochloride, 1.04 g. (5 m moles) of dicyclohexylcarbodiimide, 695 mg. (5 m moles) of p-nitrophenol and 2.25 g. (5 m moles) of D-α-aminobenzylpenicillin triethylamine salt are reacted in 20 ml. of dry dimethylformamide to yield 1.2 g. (49% yield) of the purified product.

Infrared spectrum peaks (microns; KBr): 3.0(b), 3.35, 5.6, 6.0, 6.2, 6.5, 6.85, 7.15, 7.5, 7.7, 8.0 and 8.85.

Nuclear magnetic resonance spectrum peaks (PPM; DMSO-$D_6$): 1.48(d,6H), 3.72(6H), 3.93(1H), 5.2–5.8(c,3H), 7.3(7H) and 8.9(1H).

EXAMPLE 9

6-[D-2-Phenyl-2-(3-{2-imidazolinyl}propionamido)acetamido]penicillanic acid (Ar = $C_6H_5$; A = $-(CH_2)_2-$; $R_1$ = H; $R_2$ and $R_3$ together = $-CH_2CH_2-$)

Employing the procedure of Example 2, 1.8 g. (4 m moles) of D-α-aminobenzylpenicillin triethylamine salt, 1.97 g. (10 m moles) of 3-(2-imidazolinyl)propionyl chloride hydrochloride and 1.4 ml. (10 m moles) of triethylamine in 25 ml. of dry dimethylformamide gave, on work-up, 1.55 g. (77% yield) of the purified product.

Infrared spectrum peaks (microns; KBr): 3.0(b), 3.4, 5.62, 6.0, 6.2, 6.6, 6.95, 7.15, 7.55, 7.75, 8.0, 8.3 and 8.8.

Nuclear magnetic resonance spectrum peaks (PPM; DMSO-$D_6$): 1.5(6H), 2.55(b,4H), 3.75(s,4H), 4.05(s,1H), 5.24–5.6(c,3H), 7.36(5H), 7.8(b,2H) and 8.4(1H).

EXAMPLE 10

6-[DL-2-Phenyl-2-(N,N-pentamethyleneamidinoacetamido)acetamido]penicillanic acid (Ar = $C_6H_5$; A = $-CH_2-$; $R_1$ and $R_2$ together = $-(CH_2)_5-$; $R_3$ = H)

Dicyclohexylcarbodiimide (1.04 g., 5 m moles) is added with stirring to a solution of 695 mg. (5 m moles) of p-nitrophenol and 1.03 g. (5 m moles) of N,N-pentamethyleneamidinoacetic acid hydrochloride in 20 ml. of dimethylformamide, and the reaction mixture allowed to stir for 2 hrs. at room temperature under a nitrogen atmosphere. DL-α-Aminobenzylpenicillin triethylamine salt (2.25 g., 5 m moles) is then added and the stirring continued for 24 hrs. The mixture is filtered and the filtrate poured into 300 ml. of diethyl ether. The resulting precipitate is filtered and purified by suspension in 300 ml. of methylene chloride to which is added 1.5 ml. of triethylamine. The purified product is filtered and dried in vacuo.

EXAMPLE 11

Employing the indicated procedure, and starting with the requisite D-α-aminoarylmethylpenicillin and acid or acid chloride, the following congeners are synthesized:

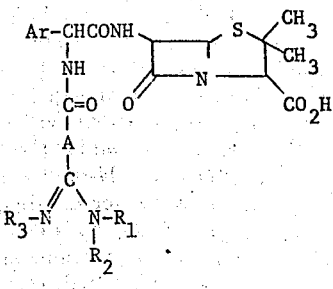

| Ar | A | $R_1$ | $R_2$ | $R_3$ | Procedure |
|---|---|---|---|---|---|
| $C_6H_5-$ | $CH_3\overset{|}{C}H-$ | $H-$ | | $-(CH_2)_2-$ | Example 2 |
| $C_6H_5-$ | $-CH_2-$ | $H-$ | | $-(CH_2)_3-$ | Example 1 |

| Ar | A | R₁ | R₂ R₃ | -continued<br>Procedure |
|---|---|---|---|---|
| $C_6H_5-$ | $-CH_2-$ | $H-$ | $-(CH_2)_5-$ | Example 1 |
| $C_6H_5-$ | $-CH_2-$ | $CH_3-$ | $-(CH_2)_2-$ | Example 1 |
| $C_6H_5-$ | $-CH(CH_3)CH_2-$ | $n-C_3H_7-$ | $-(CH_2)_3-$ | Example 2 |
| $C_6H_5-$ | $CH_3CH_2CH-$ | $H-$ | $-(CH_2)_4-$ | Example 2 |
| $C_6H_5-$ | $-(CH_2)_2-$ | $C_2H_5-$ | $-(CH_2)_3-$ | Example 2 |
| $C_6H_5-$ | $(CH_3)_2C-$ | $CH_3-$ | $-(CH_2)_2-$ | Example 2 |
| $4-HOC_6H_5-$ | $-CH_2-$ | $H-$ | $-(CH_2)_2-$ | Example 1 |
| $4-HOC_6H_5-$ | $-CH_2-$ | $CH_3-$ | $-(CH_2)_2-$ | Example 1 |
| $4-HOC_6H_5-$ | $-(CH_2)_2-$ | $H-$ | $-(CH_2)_5-$ | Example 2 |
| $4-HOC_6H_5-$ | $-(CH_2)_2-$ | $C_2H_5-$ | $-(CH_2)_3-$ | Example 2 |
| $4-HOC_6H_5-$ | $-CH(CH_3)CH_2-$ | $n-C_3H_7-$ | $-(CH_2)_3-$ | Example 1 |
| $4-HOC_6H_5-$ | $CH_3CH-$ | $H-$ | $-(CH_2)_2-$ | Example 1 |
| $2-C_4H_3S-$ | $-CH_2-$ | $H-$ | $-(CH_2)_3-$ | Example 1 |
| $2-C_4H_3S-$ | $-CH_2-$ | $H-$ | $-(CH_2)_3-$ | Example 1 |
| $2-C_4H_3S-$ | $-CH_2-$ | $CH_3-$ | $-(CH_2)_2-$ | Example 1 |
| $2-C_4H_3S-$ | $-(CH_2)_2-$ | $C_2H_5-$ | $-(CH_2)_3-$ | Example 2 |
| $3-C_4H_3S-$ | $-CH_2-$ | $H-$ | $-(CH_2)_2-$ | Example 1 |
| $3-C_4H_3S-$ | $-CH_2-$ | $CH_3-$ | $-(CH_2)_2-$ | Example 1 |
| $3-C_4H_3S-$ | $-(CH_2)_2-$ | $H-$ | $-(CH_2)_3-$ | Example 2 |
| $3-C_4H_3S-$ | $CH_3CH-$ | $H-$ | $-(CH_2)_2-$ | Example 2 |
| $3-C_4H_3S-$ | $(CH_3)_2C-$ | $CH_3-$ | $-(CH_2)_2-$ | Example 2 |
| $3-C_4H_3S-$ | $-CH(CH_3)CH_2-$ | $n-C_3H_7-$ | $-(CH_2)_3-$ | Example 2 |
| $3-C_4H_3S-$ | $-CH_2-$ | $H-$ | $-(CH_2)_5-$ | Example 2 |

EXAMPLE 12

6-[D-2-Phenyl-2-(acetimidoylaminoacetamido)acetamido]penicillanic acid (Ar = $C_6H_5$; A = $-CH_2-$; $R_1$ and $R_2$ = H; $R_4$ = $CH_3$)

A suspension of 1.58 g. (3.5 m moles) of D-α-aminobenzylpenicillin triethylamine salt in 35 ml. of dry dimethylformamide is treated with 0.5 ml. (3.5 m moles) of triethylamine and the mixture cooled to 0° C. in an ice bath while being vigorously stirred. Acetimidoylaminoacetyl chloride hydrochloride (595 ml., 3.5 m moles) is added and the reaction mixture allowed to stir in the cold for 30 min. An additional 595 mg. (3.5 m moles) of the acid chloride and 0.5 ml. (3.5 m moles) of triethylamine are added and stirring continued for 30 min. at 0° C. and at room temperature for 30 min. The mixture is filtered, and the clear filtrate poured into 400 ml. of diethyl ether. The crude product, after filtering, is suspended in 5 ml. of methylene chloride to which is then added 1 ml. of triethylamine. After stirring at room temperature for 5 hrs., the product is filtered and dried in vacuo, 755 mg. (48% yield).

Infrared spectrum peaks (microns; KBr): 3.0(b), 3.3, 5.62, 6.0, 6.2, 6.5, 6.85, 7.2, 7.6, 8.1 and 8.85.

Nuclear magnetic resonance spectrum peaks (PPM; DMSO-D₆): 1.47(d,6H), 2.18(3H), 4.0(s,1H), 4.15(2H), 5.25–5.84(c,3H), 7.38(7H) and 9.2(b,2H).

EXAMPLE 13

Employing the procedure of Example 12, 1.35 g. (3 m moles) of D-α-aminobenzylpenicillin triethylamine salt, 1.1 g. (7 m moles) of formimidoylaminoacetyl chloride hydrochloride and .98 ml. (7 m moles) of triethylamine in 15 ml. of dry dimethylformamide yielded 913 mg. (72% yield) of the desired product, 6-[D-2-phenyl-2-(formimidoylaminoacetamido)acetamido]penicillanic acid (Ar = $C_6H_5$; A = $-CH_2-$; $R_1$, $R_2$ and $R_4$ = H).

EXAMPLE 14

6-[D-2-Phenyl-2-(propionimidoylaminoacetamido)acetamido]penicillanic acid (Ar = $C_6H_5$; A = $-CH_2-$; $R_1$ and $R_2$ = H; $R_4$ = $C_2H_5-$)

A mixture of 4.5 g. (10 m moles) of D-α-aminobenzylpenicillin triethylamine salt and 1 g. (10 m moles) of triethylamine in 80 ml. of dimethylformamide, cooled to −30° C., is treated with 1.0 g. (5.2 m moles) of propionimidoylaminoacetyl chloride hydrochloride and the mixture allowed to stir at −20° to −30° C. for 20 min. at which time 1 g. more of the acid chloride is added and the stirring continued for 20 min. An additional 1 g. of triethylamine and 1 g. of acid chloride is added and the procedure repeated again after 20 min. of stirring in the cold, making a total of 4.0 g. of acid chloride and 3 g. of amine. The reaction mixture is warmed to 20° C., filtered and the yellow filtrate added to 1 l. of chloroform. The crude product, after washing with chloroform and drying (in vacuo), is dissolved in 20 ml. of dimethylformamide to which is added 1 ml. of triethylamine. The insolubles are filtered, and the filtrate added to 200 ml. of chloroform. The product is filtered and the purification procedure repeated again to provide 1.6 g. of the desired material. Trace amounts of solvent are removed by trituration of the product with diethyl ether and subsequent drying in vacuo, 1.5 g. (33% yield).

Nuclear magnetic resonance spectrum peaks (PPM: D₂O): 1.3(t,3H), 1.4(d,6H), 2.65(q,2H), 4.2(s,1H), 4.25(s,2H), 5.45(s,2H), 5.58(s,1H) and 7.5(s,5H).

EXAMPLE 15

Starting with the requisite chemical reagents and employing the procedure of Example 14, the following homologs are synthesized:

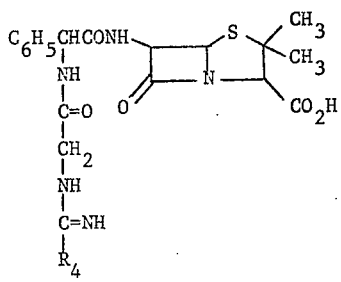

| $R_4$ | Yield, % | NMR+ |
|---|---|---|
| n-$C_3H_7$ | 36.5 | 0.9(t,3H), 1.4(s,6H), 1.2–2.0(q, 2H), 2.2–2.6(t,2H), 3.8(s,1H), 4.2 (d,2H), 5.3(s,2H), 5.4(s,1H), and 7.3(s,5H). |
| i-$C_3H_7$ | 38.0 | 1.0–1.6(2xd,12H), 2.4–3.0(2H), 3.8 (s,1H), 4.2(d,2H), 5.35(s,2H), 5.5 (s,1H), and 7.3(s,5H). |

+nuclear magnetic resonance peaks PPM - $D_2O$.

EXAMPLE 16

Employing the procedure of Example 14, and starting with the requisite reagents, the following penicillins are prepared:

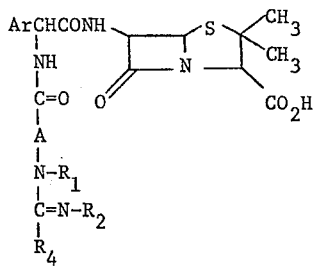

| Ar | A | $R_1$ | $R_2$ | $R_4$ |
|---|---|---|---|---|
| $C_6H_5$— | —$CH_2$— | $CH_3$— | H— | H— |
| $C_6H_5$— | —$CH_2$— | H— | $CH_3$— | $CH_3$— |
| $C_6H_5$— | —$CH_2$— | $C_2H_5$— | $CH_3$— | $CH_3$— |
| $C_6H_5$— | —$(CH_2)_2$— | H— | n-$C_3H_7$— | n-$C_3H_7$— |
| $C_6H_5$— | —$(CH_2)_2$— | i-$C_3H_7$— | H— | H— |
| $C_6H_5$— | $CH_3CH$— | H— | $C_2H_5$— | $C_2H_5$— |
| $C_6H_5$— | $CH_3CH_2CH$— | n-$C_3H_7$— | H— | i-$C_3H_7$— |
| $C_6H_5$— | —$CH(CH_3)CH_2$— | H— | H— | $CH_3$— |
| 4-$HOC_6H_4$— | —$CH_2$— | H— | H— | H— |
| 4-$HOC_6H_4$— | —$CH_2$— | H— | H— | i-$C_3H_7$— |
| 4-$HOC_6H_4$— | —$CH_2$— | H— | $CH_3$— | $CH_3$— |
| 4-$HOC_6H_4$— | —$(CH_2)_2$— | $CH_3$— | H— | $C_2H_5$— |
| 4-$HOC_6H_4$— | $CH_3CH$— | H— | $C_2H_5$— | $C_2H_5$— |
| 4-$HOC_6H_4$— | —$CH_2CH(CH_3)$— | H— | H— | H— |
| 2-$C_4H_3S$— | —$CH_2$— | H— | H— | H— |
| 2-$C_4H_3S$— | —$CH_2$— | H— | H— | $C_2H_5$— |
| 2-$C_4H_3S$— | —$CH_2$— | $CH_3$— | H— | H— |
| 2-$C_4H_3S$— | —$CH_2$— | $C_2H_5$— | $CH_3$— | $CH_3$— |
| 2-$C_4H_3S$— | —$(CH_2)_2$— | H— | n-$C_3H_7$— | n-$C_3H_7$— |
| 2-$C_4H_3S$— | $CH_3CH$— | H— | $C_2H_5$— | $C_2H_5$— |
| 3-$C_4H_3S$— | —$CH_2$— | i-$C_3H_7$— | H— | H— |
| 3-$C_4H_3S$— | —$(CH_2)_2$— | H— | i-$C_3H_7$— | $CH_3$— |
| 3-$C_4H_3S$— | $CH_3CH_2CH$— | n-$C_3H_7$— | H— | i-$C_3H_7$— |
| 3-$C_4H_3S$— | —$CH(CH_3)CH_2$— | H— | H— | $CH_3$— |
| 3-$C_4H_3S$— | —$CH_2CH(CH_3)$— | H— | H— | H— |

EXAMPLE 17

6-[D-2-Phenyl-2-(p-chloro-phenylacetimidoylaminoacetamido)acetamido]-penicillanic acid (Ar = $C_6H_5$; A = —$CH_2$—; $R_1$ and $R_2$ = H; $R_5$ = p-$ClC_6H_4CH_2$—)

To 13.5 g. (0.03 mole) of D-α-aminobenzylpenicillin triethylamine salt and 3 g. (0.03 mole) of triethylamine in 240 ml. of dry dimethylformamide, cooled to −30° C., is added 4.2 g. (0.015 mole) of p-chloro-phenylacetimidoylaminoacetyl chloride hydrochloride. After stirring in the cold for 45 min. 4.2 g. (0.015 mole) more of the acid chloride is added, followed, after 45 min., by the addition of 3 g. (0.03 mole) of triethylamine. Alternate additions are continued at 45 min. intervals until a total of 16.8 g. (0.06 mole) of acid chloride and 9.09 g. (0.09 mole) of triethylamine has been added to the penicillin salt. The reaction mixture is allowed to warm to room temperature and is subsequently filtered and the filtrate poured into 2.5 l. of chloroform. The resulting precipitate is filtered, washed successively with chloroform and ether and dried in vacuo, 5.6 g. The crude product is then dissolved in 50 ml of dimethylformamide containing 4 g. of triethylamine. A small amount of insolubles are filtered, the filtrate added to 700 ml. of chloroform and the precipitate product suction filtered. The product is further purified by trituration twice in 80 ml. of methylene chloride containing 2 g. of triethylamine and, finally, by trituration in methylene chloride alone. The pure product is dried in vacuo, 4.8 g. (28% yield).

Nuclear magnetic resonance spectrum peaks (PPM; DMSO-$D_6$): 1.4(d,6H), 3.4–4.3(s,6H), 5.3(s,2H), 5.8(s,1H), 7–7.7(s,11H) and 9.0(s,2H).

EXAMPLE 18

Employing the procedure of Example 17, and starting with D-α-aminobenzylpenicillin triethylamine salt and the appropriate acid chloride the following congeners are synthesized:

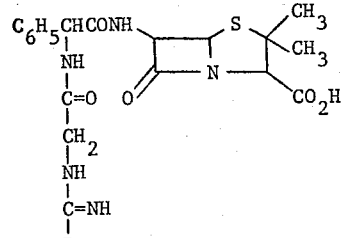

| $R_5$ | Yield, % | NMR+* |
|---|---|---|
| $C_6H_5$— | 4.7 | 1.5(d,6H), 4.0–5.2(m,9H), 5.3 (s,2H), 5.8(s,1H), and 7–8.0 (m,12H). |
| p-$CH_3OC_6H_4$— | 9.8 | *1.4(d,6H), 3.8(s,3H), 3.95(s, 1H), 4.3(s,3H), 5.3(s,2H), 5.8(s,1H) and 6.8–8.0(m,10H). |
| p-$CF_3C_6H_4$— | 6.8 | *1.4(d,6H), 4.0(s,1H), 4.2(s, 2H), 5.25(s,2H), 5.7(s,1H) and 6.8–8(m,14H). |

-continued

| $R_5$ | Yield, % | NMR+* |
|---|---|---|
| p-ClC$_6$H$_4$— | 12.0 | 1.3(d,6H), 3.8(s,1H), 4.1(s, 2H), 5.2(s,2H), 5.62(s,1H), 5.8–7.0(s,3H), 7.0–7.8(m,9H) and 8.35(s,2H). |
| p-FC$_6$H$_4$— | 16.0 | 1.4(d,6H), 4(s,1H), 4.3(s, 2H), 4–5.3(s,6H), 5.3(s,2H), 5.8(s,1H), 7–7.6(s,7H), and 7.6–8(m-2H). |
| p-BrC$_6$H$_4$— | 8.5 | 1.45(d,6H), 3.9(s,1H), 4.2(s, 2H), 5.25(s,2H), 4.4–5.8(s, 7H), 5.8(s,1H), 7–8(2xs,12H), and 9.0(s,2H). |
| p-CH$_3$C$_6$H$_4$— | 5.1 | 1.4(d,6H), 2.4(s,3H), 4.0(s, 1H), 4.3(s,2H), 5.25(s,2H), 5.3–6.2(m,8H), and 7–8(m,10H). |
| m-ClC$_6$H$_4$— | 8.7 | 1.4(d,6H), 3.9(s,1H), 4.2(s, 2H), 5–6.6(m,8H), 7–8(m,11H) and 9.05(t,2H). |
| 3,4-Cl$_2$C$_6$H$_3$— | 6.5 | *1.4(d,6H), 3.9(s,1H), 4.1(s, 2H), 4.8–6(m,11H), 7.2(s,7H), 7.7(s,2H) and 8.0(s,1H). |
| 3,5-Cl$_2$C$_6$H$_3$— | 7.4 | *1.4(d,6H), 4.0(overlapping s, 3H), 5.0–7.0(m,9H), 7.4(s,5H), 7.8(s,3H) and 9.0(t,2H). |
| 3,5-Br$_2$C$_6$H$_3$— | 21 | 1.5(d,6H), 4.1(s,3H), 5.4(m, 2H), 5.8(d,1H), 7.4(s,5H), 8.0 s,3H), 8.0–9.1(s,5H), and 9.15 5,2H). |

| and | $R_6$ | Yield, % | NMR |
|---|---|---|---|
| | 2-C$_4$H$_3$S | 17 | 1.4(d,6H), 4.0(s,3H), 5.2–5.5 (s,2H), 5.7(d,1H), 7–7.6(s,6H), 7.6–7.9(5H) and 8.6–9.3(t,2H). |
| | 2-C$_4$H$_3$O | 8.4 | 1.5(d,6H), 4.0(s,1H), 4.2(s, 2H), 5.4(s,2H), 5.9(s,1H), 4.7–6.2(s,6H), 6.9(s,1H), 7.2–7.7(s,5H), 7.8(s,1H), and 8.15(s,1H). |

+nuclear magnetic resonance spectrum peaks PPM - DMSO-D$_6$
*not scanned above 500 Hz

EXAMPLE 19

The procedure of Example 17 is again repeated, starting with the requisite reagents, to provide the following penicillin analogs: 6-[D-2-phenyl-2-(N-{o-chlorobenzimidoyl} N-methylaminoacetamido)acetamido]penicillanic acid, 6-[D-2-phenyl-2-(N{N'-ethyl-m-fluorobenzimidoyl}aminoacetamido]penicillanic acid, 6-[D-2-phenyl-2-(N-{m-methoxy-phenylacetimidoyl}aminoacetamido)acetamido]-penicillanic acid, 6-[D-2-phenyl-2-(2-N-{o-trifluoromethylbenzimidoyl}aminopropionamido)acetamido]penicillanic acid, 6-[D-2-phenyl-2-(4-N-{N'-n-propyl-m-bromo-phenylacetimidoyl}aminobutyramido)acetamido]-penicillanic acid, 6-[D-2-p-hydroxyphenyl-2-(N-{N'-methyl-p-trifluoro-phenylacetimidoyl}aminoacetamido)acetamido]-penicillanic acid, 6-[D-2-p-hydroxyphenyl-2-(N-{m-methoxybenzmidoyl}aminoacetamido)acetamido]-penicillanic acid, 6-[D-2-p-hydroxyphenyl-2-(3-N-{o-chlorobenzimidoyl}aminobutyramido)acetamido]-penicillanic acid, 6-[D-2-α-thienyl-2-(N-{O-chlorobenzimidoyl}N-methylaminoacetamido)acetamido]-penicillanic acid, 6-[DL-2-α-thienyl-2-(N-{N'-ethyl-m-fluorobenzimidoyl}aminoacetamido)acetamido]-penicillanic acid, 6-[D-2-α-thienyl-2-(N-{m-methoxy-phenylacetimidoyl}aminoacetamido)acetamido]-penicillanic acid, 6-[D-2-α-thienyl-2-(2-N-{o-trifluoromethylzimidoyl}aminopropionamido)acetamido]penicillanic acid, 6-[D-2-β-thienyl-2-(4-N-{N'-n-propyl-m-bromo-phenylacetimidoyl}aminobutyramido)acetamido]-penicillanic acid, 6-[D-2-β-thienyl-2-(3-N-{o-chlorobenzimidoyl}aminobutyramido)acetamido]-penicillanic acid, 6-[DL-2-β-thienyl-2-(N-{N'-ethyl-m-fluorobenzimidoyl}aminoacetamido)acetamido]-penicillanic acid. 6-[D-2-phenyl-2-(N-{N'-methyl-3,5-dichlorobenzimidoyl}aminoacetamido)acetamido]-penicillanic acid and 6-[D-2-p-hydroxyphenyl-2-(N-{3,5-dichlorobenzimidoyl}aminoacetamido)acetamido]penicillanic acid.

EXAMPLE 20

6-[D-2-Phenyl-2-(2-pyrrolinylaminoacetamido)acetamido]penicillanic acid
(Ar 32 C$_6$H$_5$; A = —CH$_2$—; R$_1$ = H; R$_2$ and R$_4$ together = —(CH$_2$)$_3$—)

A suspension of 4.5 g. (0.01 mole) of D-α-aminobenzylpenicillin triethylamine salt in 85 ml. of dry dimethylformamide is cooled to −10° C. in a salt ice bath and subsequently treated with 985 mg. (0.01 mole) of 2-pyrrolinylaminoacetyl chloride hydrochloride and 1.01 g. (0.01 mole) of triethylamine. After 30 min. of continued stirring and cooling an additional 985 mg. (0.01 mole) of acid chloride and 1.01 mole) of triethylamine are added and the mixture stirred for 1 hour. The ice bath is then removed and the reaction mixture allowed to warm to room temperature and stir for 45 min. The solids are filtered and the clear filtrate is added dropwise to 1 l. of diethyl ether with vigorous stirring. The crude product is filtered and suspended in 20 ml. of methylene chloride containing 3 ml. of triethylamine. After stirring at room temperature for 5 hrs., the purified product is filtered, washed with diethyl ether and

EXAMPLE 21

Employing the procedure of Example 20, and starting with the appropriate acid chloride and D-α-aminoarylmethylpenicillin, the following congeners are prepared:

EXAMPLE 22

The procedure of Example 1 is again repeated, starting with the requisite chemical reagents, to provide the following penicillins:

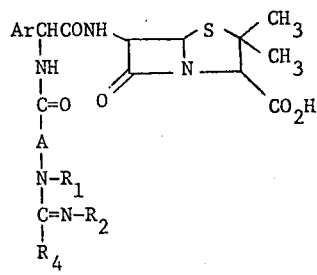

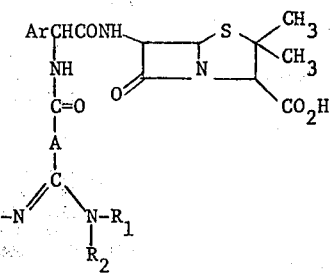

| Ar | A | $R_1$ | $R_2$ | $R_4$ |
|---|---|---|---|---|
| $C_6H_5-$ | $-CH_2-$ | $CH_3-$ | | $-(CH_2)_3-$ |
| $C_6H_5-$ | $-CH_2-$ | $n-C_3H_7-$ | | $-(CH_2)_5-$ |
| $C_6H_5-$ | $-(CH_2)_2-$ | $H-$ | | $-(CH_2)_3-$ |
| $C_6H_5-$ | $CH_3CH-$ | $H-$ | | $-(CH_2)_3-$ |
| $C_6H_5-$ | $(CH_3)_2C-$ | $CH_3-$ | | $-(CH_2)_3-$ |
| $C_6H_5-$ | $-CH(CH_3)CH_2-$ | $H-$ | | $-(CH_2)_3-$ |
| $C_6H_5-$ | $-CH_2-$ | | $-(CH_2)_2-$ | $H-$ |
| $C_6H_5-$ | $-CH_2-$ | | $-(CH_2)_3-$ | $CH_3-$ |
| $4-HOC_6H_4-$ | $-CH_2-$ | $H-$ | | $-(CH_2)_3-$ |
| $4-HOC_6H_4-$ | $-CH_2-$ | $CH_3-$ | | $-(CH_2)_3-$ |
| $4-HOC_6H_4-$ | $-CH_2-$ | $n-C_3H_7-$ | | $-(CH_2)_5-$ |
| $4-HOC_6H_4-$ | $-(CH_2)_2-$ | $H-$ | | $-(CH_2)_3-$ |
| $4-HOC_6H_4-$ | $CH_3CH-$ | $H-$ | | $-(CH_2)_3-$ |
| $4-HOC_6H_4-$ | $-CH(CH_3)CH_2-$ | $H-$ | | $-(CH_2)_3-$ |
| $4-HOC_6H_4-$ | $-CH_2-$ | | $-(CH_2)_2-$ | $H-$ |
| $2-C_4H_3S-$ | $-CH_2-$ | $H-$ | | $-(CH_2)_3-$ |
| $2-C_4H_3S-$ | $-CH_2-$ | $CH_3-$ | | $-(CH_2)_3-$ |
| $2-C_4H_3S-$ | $-CH_2-$ | $n-C_3H_7-$ | | $-(CH_2)_5-$ |
| $2-C_4H_3S-$ | $CH_3CH-$ | $H-$ | | $-(CH_2)_3-$ |
| $2-C_4H_3S-$ | $-CH_2-$ | | $-(CH_2)_2-$ | $H-$ |
| $3-C_4H_3S-$ | $-CH_2-$ | $H-$ | | $-(CH_2)_3-$ |
| $3-C_4H_3S-$ | $-CH_2-$ | $CH_3-$ | | $-(CH_2)_3-$ |
| $3-C_4H_3S-$ | $-CH_2-$ | $C_2H_5-$ | | $-(CH_2)_3-$ |
| $3-C_4H_3S-$ | $-CH(CH_3)CH_2-$ | $H-$ | | $-(CH_2)_3-$ |

| Ar | A | $R_1$ $R_2$ | $R_3$ |
|---|---|---|---|
| $C_6H_5-$ | $-CH_2-$ | $-(CH_2)_3-$ | $C_6H_5-$ |
| $C_6H_5-$ | $-CH_2-$ | $-(CH_2)_5-$ | $m-FC_6H_4CH_2-$ |
| $C_6H_5-$ | $CH_3CH_2CH-$ | $-(CH_2)_4-$ | $o-BrC_6H_4-$ |
| $C_6H_5-$ | $(CH_3)_2C-$ | $-(CH_2)_4-$ | $\alpha-C_4H_3S-$ |
| $C_6H_5-$ | $-CH_2CH(CH_3)-$ | $-(CH_2)_3-$ | $\beta-C_4H_3O-$ |
| $4-HOC_6H_4-$ | $-CH_2-$ | $-(CH_2)_3-$ | $C_6H_5-$ |
| $4-HOC_6H_4-$ | $-CH_2-$ | $-(CH_2)_5-$ | $m-FC_6H_4CH_2-$ |
| $4-HOC_6H_4-$ | $CH_3CH_2CH-$ | $-(CH_2)_5-$ | $m-CH_3OC_6H_4CH_2-$ |
| $4-HOC_6H_4-$ | $-CH_2CH(CH_3)-$ | $-(CH_2)_6-$ | $3-C_5H_4N-$ |
| $2-C_4H_3S-$ | $-CH_2-$ | $-(CH_2)_5-$ | $m-FC_6H_4CH_2-$ |
| $2-C_4H_3S-$ | $-CH_2-$ | $-(CH_2)_4-$ | $\beta-C_{10}H_7-$ |
| $2-C_4H_3S-$ | $-CH_2-$ | $-(CH_2)_5-$ | $p-BrC_6H_4-$ |
| $2-C_4H_3S-$ | $-(CH_2)_2-$ | $-(CH_2)_6-$ | $p-CF_3C_6H_4-$ |
| $2-C_4H_3S-$ | $-CH_2CH(CH_3)-$ | $-(CH_2)_3-$ | $\beta-C_4H_3O-$ |
| $C_6H_5-$ | $-CH_2-$ | $-(CH_2)_5-$ | $CH_3-$ |
| $C_6H_5-$ | $-(CH_2)_2-$ | $-(CH_2)_4-$ | $n-C_3H_7-$ |
| $4-HOC_6H_4-$ | $-CH_2-$ | $-(CH_2)_5-$ | $H-$ |
| $3-C_4H_3S-$ | $-CH_2-$ | $-(CH_2)_5-$ | $m-FC_6H_4CH_2-$ |
| $3-C_4H_3S-$ | $-CH_2-$ | $-(CH_2)_5-$ | $p-BrC_6H_4-$ |
| $3-C_4H_3S-$ | $-CH_2-$ | $-(CH_2)_3-$ | $C_6H_5-$ |
| $3-C_4H_3S-$ | $CH_3CH_2CH-$ | $-(CH_2)_4-$ | $o-BrC_6H_4-$ |
| $3-C_4H_3S-$ | $CH_3CH_2CH-$ | $-(CH_2)_5-$ | $m-CH_3OC_6H_4CH_2-$ |
| $3-C_4H_3S-$ | $-CH(CH_3)CH_2-$ | $-(CH_2)_5-$ | $2-C_5H_4N-$ |
| $3-C_4H_3S-$ | $-(CH_2)_2-$ | $-(CH_2)_4-$ | $\alpha-C_{10}H_7-$ |
| $3-C_4H_3S-$ | $-(CH_2)_2-$ | $-(CH_2)_4-$ | $n-C_3H_7-$ |

-continued

| Ar | A | $R_1$ | $R_2$ | $R_3$ |
|---|---|---|---|---|
| 3-$C_4H_3S$— | —$CH_2$— | | —$(CH_2)_5$— | $CH_3$— |
| 3-$C_4H_3S$— | —$CH_2$— | | —$(CH_2)_5$— | H— |

EXAMPLE 23

6-[D-2-Phenyl-2-({N-methyl-3,4-dichlorobenzimidoyl} aminoacetamido)acetamido]penicillanic acid (Ar = $C_6H_5$; A = —$CH_2$—; $R_1$ = H; $R_2$ = $CH_3$ and $R_5$ = 3,4-$Cl_2C_6H_3$—)

To a solution of 7.6 g. (15 m moles) of 6-[2-phenyl-2-(aminoacetamido)acetamido]penicillanic acid in 70 ml. of dimethylformamide is added 4.17 g. (18 m moles) of ethyl 3,4-dichloro-N-methylbenzimidate in 10 ml. of the same solvent. The resulting reaction mixture is allowed to stir at room temperature for 3 hrs., and is then added to 1 l. of chloroform. The precipitate is filtered, and the filtrate added to 1.5 l. of hexane. The resulting solids are filtered, dried (2.6 g.) and added to 50 ml. of methylene chloride to which is added 2.0 g. of triethylamine. The mixture is concentrated to dryness, dissolved in 25 ml. of dimethylformamide and, subsequently, treated with 400 ml. of chloroform and 600 ml. of hexane. The precipitate is filtered, washed with ether and then triturated with methylene chloride. Filtration and drying gave 1.76 g. (22% yield) of the desired product.

Nuclear magnetic resonance spectrum peaks (PPM; DMSO-$D_6$): 1.5 (d,6H), 2.9 (s,3H), 4.0(s,3H), 5.3 (m,2H), 5.65 (d,1H), 7.0–7.7 (d,13H) and 9.1 (t,2H).

EXAMPLE 24

Starting with the requisite imino ether and appropriate D-6-[2-phenyl-2-(aminoalkanoylamino)acetamido]penicillanic acid and employing the procedure of Example 23, the following congeners are prepared:

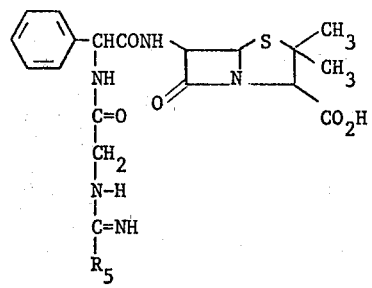

| $R_5$ | yield,% | NMR+ |
|---|---|---|
| p-$C_6H_5C_6H_4$— | 9.2 | 1.5(d,6H), 4.0(s,1H), 4.3(s, 2H), 5.3(m,2H), 5.8(d,1H), 6.0–8.0(m,17H), and 9.0(d,2H). |
| p-NC$C_6H_4$— | 35 | 1.5(d,6H), 4.0(s,1H), 4.15(s, 2H), 5.4(m,2H), 5.8(d,1H), 7.4(s,5H), 8.0(s,4H), and 9.05(m,5H). |
| o-Cl$C_6H_4$— | 11 | 1.4(d,6H), 3.9(s,1H), 4.1(s, 2H), 5.3(m,2H), 5.7(d,1H), 6.9–8.0(m,12H), and 9.0(s,2H). |
| p-I$C_6H_4$— | 16.5 | 1.5(d,6H), 3.9(s,3H), 4.4–5.8 (s,5H), 5.4(m,2H), 5.8(d,1H), 7.3(s,5H), 7.55(d,2H), 7.8(d, 2H), and 9.0(t,2H). |
| 3,5-$Cl_2C_6H_3$— | 13 | 1.5(d,6H), 3.9(s,3H), 4.8–5.9 (m,9H), 7.4(s,5H), 7.65(s,1H), 7.9(s,2H), 8.8(d,1H), and 9.0 (d,1H). |
| m-NC$C_6H_4$— | 56 | 1.5(d,6H), 3.95(s,1H), 4.2(b, 2H), 5.4(b,2H), 5.8(s,1H), and 7.2–8.4(m,9H). |
| 3,5-$F_2C_6H_3$— | — | 1.4(d,6H), 4.0(s,1H), 4.2(s, 2H), 5.0–6.2(m,14H), 7.2–7.8 (m,8H), and 9.05(t,2H). |
| 3-CN-5-Cl$C_6H_3$— | 32 | 1.5(d,6H), 4.0(b,3H), 5.4(b, 2H), 5.8(s,1H), 7.5(b,5H), and 8.25(b,3H). |
| 3-CN-5-Br$C_6H_3$— | 33 | 1.5(d,6H), 3.95(b,3H), 5.4(b, 2H), 5.8(s,1H), 7.5(b,5H), and 8.3(b,3H). |
| 3,4-$Br_2C_6H_3$— | 20 | 1.5(d,6H), 4.0(s,1H), 4.1(s, 2H), 5.4(m,2H), 5.8(d,1H), 6.0–7.4(s,8H), 7.4(s,5H), 7.7–8.3(m,3H), and 9.15(t,2H). |
| 3,5-$Br_2C_6H_3$— | 24 | 1.5(d,6H), 4.1(s,3H), 5.4(m, 2H), 5.8(d,1H), 7.4(s,5H), 8.0 (s,3H), 8.0–9.1(s,5H), and 9.15 (t,2H). |
| 3,5-$I_2C_6H_3$— | 64 | 1.5(d,6H), 4.0(s,3H), 5.4(m, 2H), 5.8(d,1H), 5.9–7.0(s,3–4 H), 7.4(s,5H), 8.25(s,3H), 8.8 (d,1H), and 9.2(d,1H). |
| 3,4,5-$Cl_3C_6H_2$— | 45 | 1.5(d,6H), 4.0(s,3H), 5.4(m, 2H), 5.9(m,8–9H), 7.4(s,5H), 8.05(s,2H), and 9.0(q,2H). |
| 3,4,5-$Br_3C_6H_2$— | 37 | 1.5(d,6H), 4.05(s,3H), 5.4(m, 2H), 5.8(d,1H), 6.0–7.4(s,6H), 7.4(s,5H), 8.2(s,2H), 8.9(d, 1H), and 9.15(d,1H). |

-continued

| $R_5$ | yield,% | NMR⁺ |
|---|---|---|
| 3,5-Cl₂-4-BrC₆H₂— | 34 | 1.5(d,6H), 4.05(s,3H), 5.3(m, 2H), 5.8(d,1H), 7.0-8.0(s, 14H), 8.05(s,2H), and 8.7-9.3(q,2H). |
| 3,5-Br₂-4-FC₆H₂— | 40 | 1.5(d,6H), 4.1(s,1H), 4.25(s, 2H), 4.6-6.0(m,16-17H), 7.4 (s,5H), 8.2(t,2H), and 9.16 (t,2H). |
| 3,5-Br₂-4-ClC₆H₂— | 28 | 1.5(d,6H), 4.1(s,3H), 5.45(m, 2H), 5.9(d,1H), 6.4-8.0(s,7H), 7.5(s,5H), 8.4(s,2H), and 8.7-9.45(q,2H). |
| 3,5-Br₂-4-(C₂H₅)HNC₆H₂— | 12 | 1.5(d,6H), 4.18(s,1H), 4.32(s, 2H), 5.0-6.8(m,9-10H), 7.5(s, 7H), 8.1(s,2H), and 9.3(t,2H). |
| m-CF₃C₆H₄— | 40 | 1.5(d,6H), 4.0(s,1H), 4.25(s, 2H), 5.4(m,2H), 5.8(d,2H), 7.4(s,5H), 7.7-8.3(m,4H), 8.0-9.7(s,4H), and 9.1(t,2H). |
| p-CF₃C₆H₄— | 6.8 | 1.5(d,6H), 4(s,1H), 4.2(s,2H), 5.4(m,2H), 6.4-8.2(m,16H), and 9.0(q,2H). |
| 3,5-(CF₃)₂C₆H₃— | 40 | 1.5(d,6H), 4.0(s,3H), 5.35(m, 2H), 5.8(d,1H), 7.4(s,5H), 8.0-9.35(m,8H), and 8.85-9.35(q,2H). |
| 3,5-(NC)₂C₆H₃— | 32 | 1.5(d,6H), 4.0(b,3H), 5.4(b,2H), 5.8(s,1H), 7.5(b,5H), and 8.25 (b,3H). |
| p-CF₃SC₆H₄— | 37 | 1.5(d,6H), 4.05(s,1H), 4.4(s, 2H), 5.2-5.6(m,2H), 5.9(d,1H), 7.5(s,10H), 8.0(s,4H), and 9.15(s,2H). |
| p-H₂NCOC₆H₄— | 73 | 1.5(d,6H), 4.0(s,1H), 4.4(b, 2H), 5.45(m,2H), 5.8(s,1H), and 7.35-8.0(m,9H). |
| p-H₂NCONHC₆H₄— | 91 | 1.5(d,6H), 3.95(s,1H), 4.35(b, 2H), 5.35(m,2H), 5.75(s,1H), and 7.35-7.65(m,9H). |
| p-CH₃CONHC₆H₄— | 68 | 1.5(d,6H), 2.1(s,3H), 3.95(s, 1H), 4.25(s,2H), 5.3(m,2H), 5.7(s,1H), 7.2-7.65(s,9H). |
| p-CH₃COC₆H₄— | 83 | 1.5(d,6H), 2.6(s,3H), 4.0(s, 1H), 4.2(b,2H), 5.4(m,2H), 5.8 (s,1H), 7.35(b,5H), and 8.0 (s,4H). |
| p-H₂NC(=NH)—C₆H₄ | 54 | 1.5(d,6H), 4.0(s,1H), 4.2(b, 2H), 5.4(m,2H), 5.8(s,1H), 7.4 (b,5H), and 8.0(b,4H). |
| p-HOC₆H₄— | 75 | 1.5(d,6H), 3.95(s,1H), 4.2(b, 2H), 5.35(m,2H), 5.75(s,1H), and 7.4(m,9H). |
| m-HOC₆H₄— | 57 | 1.5(d,6H), 4.0(s,1H), 4.24(b, 2H), 5.4(m,2H), 5.8(s,1H), and 7.45(b,9H). |
| m-O₂NC₆H₄— | 72 | 1.5(d,6H), 3.95(s)+4.1(b,3H), 5.4(m,2H), 5.8(s,1H), 7.35(b, 5H), 7.9(m,1H), and 8.35(m,3H). |
| p-O₂NC₆H₄— | 72 | 1.45(d,6H), 3.95(s)+4.1(b,3H), 5.35(m,2H), 5.8(s,1H), 7.3(b, 5H), and 8.15(q,4H). |
| p-H₂NSO₂C₆H₄— | 64 | 1.5(d,6H), 3.95(s,1H), 4.2(b, 2H), 5.35(m,2H), 5.8(s,1H), 7.35(b,9H), and 7.95(s,4H). |
| C₆H₅CH₂— | 81 | 1.45(d,6H), 3.94-4.2(b,5H), 5.35 (m,2H), 5.75(s,1H), and 7.35 (b,10H). |
| 2,6-Cl₂C₆H₃CH₂— | 67 | 1.5(d,6H), 4.0(b,3H), 4.2(b, 2H), 5.4(m,2H), 5.7(s,1H), and 7.4(b,8H). |
| m-ClC₆H₄CH₂— | 68 | 1.5(d,6H), 3.95(s)+4.25(b, 5H), 5.4(m,2H), 5.8(s,1H), and 7.5(m,9H). |
| p-CH₃OC₆H₄CH₂— | 72 | 1.5(d,6H), 3.75(b)+3.95(s)+4.2 (b,8H), 5.4(m,2H), 5.8(s,1H), 6.9(d,2H), and 7.4(b,9H). |
| p-HOC₆H₄CH₂— | 78 | 1.5(d,6H), 3.75(b)+3.95(s)+4.2 (b,5H), 5.35(m,2H), 5.8(s,1H), 6.75(d,2H), and 7.4(b,9H). |
| p-FC₆H₄CH₂— | 77 | 1.5(d,6H), 3.95(b,3H), 4.2(b, 2H), 5.4(m,2H), 5.75(s,1H), and 7.4(m,9H). |
| p-C₂H₅O₂CC₆H₄— | 80 | 1.5(m), 4.0(s), 4.2(m), 5.2(m), 5.8(m), 7.4(s), and 8.1(s). |
| 3,5-(C₂H₅O₂C)₂—C₆H₃— | 59 | 1.4(t), 1.5(m), 4.0(s), 4.4(q), 5.2-6.7(m) and 7.4(s). |
| m-C₂H₅O₂CC₆H₄— | 62 | 1.4(m), 4.0(s), 4.3(q), 5.3(m), 5.8(m), 7.3(s), and 7.6-8.5(m). |
| 3,5-(i-C₄H₉O)₂—C₆H₃— | 51 | 0.8(t), 1.2(d), 1.4(m), 4.3(m), 5.0-6.0(m), 6.7(d), and 7.2(m). |
| 3,4-(i-C₄H₉O)₂— | 51 | 0.7-1.9(e), 3.8-4.8(e), 4.8- |

| $R_5$ | yield,% | NMR+ |
|---|---|---|
| $C_6H_3-$ | | 6.2(e) and 7.3(s). |
| 3,5-(i-$C_3H_7O)_2-$<br>$C_6H_3-$ | 72 | 1.4(t), 4.0(s), 4.6(m), 5.4(m), 5.8(s), and 7.5(s). |
| 3,4-$(CH_2=CHCH_2O)_2-$<br>$C_6H_3-$ | 77 | 1.5(d), 4.0(s), 4.7(m), 5.2–6.2(m), and 7.0–7.7(c). |
| 3,5-(i-$C_3H_7O)_2-$<br>$C_6H_3-$ | 65 | 1.0–1.7(m), 3.9(s), 4.2–5.0 (m), 5.3(m), 5.8(m), 6.8(d) and 7.4(s). |
| 3,4-$(CH_3CO_2)_2-$<br>$C_6H_3-$ | 69 | 1.2–1.6(e), 2.3(s), 2.5(s), 3.6–4.6(m), 5.3(s), 5.7(m), and 7.4(s). |
| 3-$CH_3$S-4-$CH_3-$<br>$OC_6H_3-$ | 63 | 1.0–2.0(e), 2.5(s), 3.9(s), 4.4(m), 5.3(m), 5.8(m), and 7.0–7.9(e). |
| p-$CH_3SC_6H_4-$ | 65 | 1.6(d), 2.5(s), 4.0(s), 4.4 (m), 5.3(m), 5.8(m), 7.4(s), and 7.8(m). |
| 3,5-$(CH_3S)_2-$<br>$C_6H_3-$ | 80 | 1.6(d), 2.6(s), 4.0(s), 4.5 (m), 5.0–6.0(m) and 7.4(s). |
| m-$CH_3SC_6H_4-$ | 72 | 1.5(m), 2.5(s), 3.9(s), 4.3 (m), 5.3(m), 5.8(m), and 7.5(d). |
| m-(i-$C_3H_7$S)–<br>$C_6H_4-$ | 70 | 1.3(d), 1.5(d), 3.6(m), 4.0 (s), 4.4(m), 5.3(m), 5.8(m), and 7.5(m). |
| 3,4,5-$(CH_3O)_3-$<br>$C_6H_2-$ | 79 | 1.0–2.0(e), 3.8(s), 5.0–6.0 (e) and 7.2(s). |
| m-$CH_3SO_2C_6H_4-$ | 78 | 1.6(d), 3.3(s), 4.0(s), 4.3 (m), 5.3–6.7(e), 7.3(s) and 7.6–8.4(m). |
| p-$CH_3SO_2C_6H_4-$ | 82 | 1.6(d), 3.4(s), 4.0(s), 4.4 (m), 5.2–6.0(e), 7.5(s), and 8.2(s). |
| 3-$CH_3SO_2$-4-$CH_3-$<br>$OC_6H_3-$ | — | 1.4(d), 3.3(s), 4.0(s), 4.4 (m), 4.8–6.0(e), 7.4(s), and 8.3(s). |
| 3,5-$(CH_3SO_2)_2-$<br>$C_6H_3-$ | 73 | 1.5(d), 3.5(s), 4.0(s), 4.3 (m), 5.4(m), 5.6–6.8(e), 7.4 (s), and 8.4–9.7(m). |
| p-$(CH_3)_3CCONHC_6H_4-$ | 58 | 1.2(s), 1.5(d), 3.9(s), 4.4 (m), 5.3(m), 5.8(m), 7.3(s), and 7.8(s). |
| p-$(CH_3)_2NC_6H_4-$ | 74 | 1.6(d), 3.1(s), 4.0(s), 4.5 (m), 5.3(m), 5.8(m), 6.8(m), and 7.2–8.0(e). |
| 2-$C_{10}H_7-$ | 74 | 1.5(d), 4.0(s), 4.5(m), 5.3 (m), 5.8(m), 7.2–7.8(m), 8.0 (m), and 8.5(s). |
| m-$H_2NSO_2C_6H_4-$ | — | 1.4(s,3H), 1.65(s,3H), 4.05 (b,1H), 4.1(s,2H), 5.15(s, 1H), 5.2–5.35(m,1H), 5.6–5.8 (m,1H), 7.4(s,5H), and 7.6–8.4(m,4H). |
| p-$CH_3NHSO_2C_6H_4-$ | 20 | 1.5(d,6H), 2.58(s,3H), 4.05 (s,1H), 4.25(d,2H), 7.25(s, 5H), and 8.0(s,4H). |
| p-$(CH_3)_2NSO_2-$<br>$C_6H_4-$ | 20 | 1.5(d,6H), 2.74(s,6H), 4.05 (s,1H), 4.28(d,2H), 7.35(s, 5H), and 7.85(s,4H). |
| m-$(CH_3)_2NSO_2-$<br>$C_6H_4-$ | 89 | 1.5(d,6H), 2.74(s,6H), 4.25 (d,2H), 4.12(s,1H), 7.30(s, 5H), and 8.0–8.4(m,4H). |
| 3,5-$[(CH_3)_2-$<br>$NSO_2]_2-$<br>$C_6H_3-$ | 30 | 1.5(d,6H), 2.60(s,12H), 4.3 (d,2H), 4.15(s,1H), 7.25(s, 5H), and 8.0–8.4(m,3H). |
| 3-$(CH_3)_2NSO_2$-4-<br>$ClC_6H_3-$ | 30 | 1.5(d,6H), 2.9(s,6H), 4.2 (s,1H), 4.4(d,2H), 7.4(s, 5H), and 7.8–8.6(m,3H). |
| 3-$(CH_3)_2NSO_2$-4-<br>$BrC_6H_3-$ | — | 1.5(d,6H), 3.0(s,6H), 4.4 (d,2H), 4.1(s,1H), 7.5(m, 5H), and 7.8–8.6(m,3H). |
| 2-F-5-$ClC_6H_3-$ | 38 | 1.45(d,6H), 3.95(s,1H), 4.3 (b,2H), 5.4(b,2H), 5.8(s, 1H), and 7.2–8.0(c,8H). |
| 3,5-$(H_2NSO_2)_2-$<br>$C_6H_3-$ | 25 | 1.5(d,6H), 3.9(s,1H), 4.25 (b,2H), 5.4(b,2H), 5.8(s, 1H), 7.4(b,5H), and 8.5(c, 3H). |
| m-$CH_3COC_6H_4-$ | 83 | 1.5(d,6H), 2.65(s,3H), 4.05 (b,3H), 5.4(b,2H), 5.75(s,1H), 7.5(b,5H), and 7.65–8.6(c,4H). |
| o-$FC_6H_4-$ | 36 | 1.5(d,6H), 3.9(s,1H), 4.3(b, 2H), 5.4(b,2H), 5.8(s,1H), and 7.2–8.0(c,9H). |
| 3,4,5-$I_3C_6H_2-$ | 10 | 1.5(d,6H), 4.1(s,3H), 4.4–5.6 (b,1H), 5.45(m,2H), 5.9(d,1H), 7.4(s,5H), 8.25(s,2H), and 9.2 (t,2H). |
| m-$H_2NCOC_6H_4-$ | 60 | 1.5(d,6H), 4.0(s,1H), 4.3(b, 2H), 5.4(b,2H), 5.8(s,1H), and 7.1–8.4(c,9H). |
| 3,5-$(CH_3O_2C)_2-$ | 33 | 1.5(d,6H), 4.0(b,9H), 5.4(b, |

| $R_3$ | yield,% | NMR+ |
|---|---|---|
| $C_6H_3-$ | | 2H), 5.8(s,1H), 7.45(b,5H), 8.6(s,2H), and 8.7(s,1H). |

+Nuclear magnetic resonance spectrum peaks - PPM; DMSO-$D_6$.
*Not scanned beyond 500 Hz.

EXAMPLE 25

The procedures of Example 23 is again repeated, starting with the requisite reagents, to provide the following analogs:

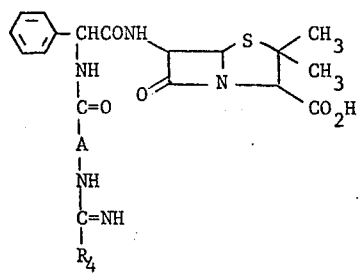

| $R_4$ | A | NMR+* |
|---|---|---|
| 3,5-$Br_2C_6H_3-$ | $-(CH_2)_2-$ | 1.4(d,6H), 2.7(t,2H), 3.7 (5,2H), 4.0(s,1H), 5.4(m, 3H), 7.4(s,5H), 7.9(s,2H), and 8.1(s,1H). |
| 3,5-$(CF_3)_2C_6H_3-$ | $-(CH_2)_2-$ | 1.4(d,6H), 2.7(t,2H), 3.7 (t,2H), 4.0(s,1H), 5.5(m, 3H), 7.4(s,5H), and 8.4 (s,3H). |
| 3,5-$Cl_2C_6H_3-$ | $-(CH_2)_2-$ | 1.5(d,6H), 2.7(t,2H), 3.7 (t,2H), 4.0(s,1H), 5.4(m, 3H, 7.4(s,5H), 7.8(s,2H), and 7.9(s,1H). |
| 3,5-$Br_2C_6H_3-$ | $CH_3\overset{\|}{C}H-$ | 1.6(m,9H), 4.0(s,1H), 4.2 (m,1H), 5.6(m,3H), 7.4(s, 6H), 8.0(s,2H), and 9.1 (m,2H). |
| 3,5-$(CF_3)_2C_6H_3-$ | $CH_3\overset{\|}{C}H-$ | 1.5(m,9H), 5.3(m,3H), 7.4 (s,6H), and 8.4(s,2H). |
| 3,5-$Cl_2C_6H_3-$ | $CH_3\overset{\|}{C}H-$ | 1.5(m,9H), 5.4(m,3H), 7.4 (s,6H), and 7.9(s,2H). |
| p-$ClC_6H_4CH_2-$ | $-(CH_2)_2-$ | 1.3(s,3H), 1.4(s,3H), 2.3 (t,2H), 3.2(m,2H), 3.9(s, 2H), 4.15(s,1H), 5.4-5.7 (m,3H), and 7.4(m,9H). |
| p-$ClC_6H_4CH_2-$ | $(CH_3)_2CH\overset{\|}{C}H-$ | 0.9(d,6H), 1.42(s,3H), 1.5(s,3H), 1.2(m,1H), 3.8 (m,3H), 4.15(s,1H), 5.4 (m,3H), and 7.3(m,9H). |
| 3,4-$Cl_2C_6H_3-$ | $-(CH_2)_2-$ | 1.3(s,3H), 1.4(s,3H), 2.3 (t,2H), 3.2(m,2H), 4.1(s, 1H), 5.3-5.8(m,3H), and 7.3(m,8H). |

+Nuclear magnetic resonance spectrum peaks-PPM-DMSO-$D_6$
*Not scanned beyond 500 Hz

EXAMPLE 26

Starting with the appropriate imino ether and requisite D-6-[2aryl - 2-(aminoalkanoylamino)acetamido]-penicillanic acid and employing the procedure of Example 23, the following penicillins are prepared:

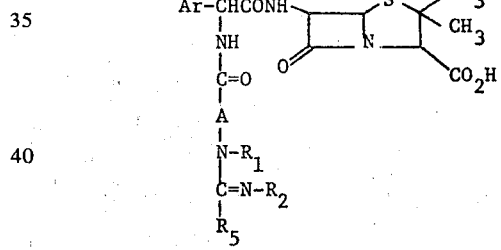

| Ar | A | $R_1$ | $R_2$ | $R_5$ |
|---|---|---|---|---|
| $C_6H_5-$ | $-CH_2-$ | $CH_3-$ | $H-$ | p-$CH_3COC_6H_4-$ |
| $C_6H_5-$ | $-CH_2-$ | $H-$ | $H-$ | m-$CH_3COC_6H_4-$ |
| $C_6H_5-$ | $CH_3CH_2\overset{\|}{C}H-$ | $H-$ | $H-$ | m-$CH_3COC_6H_4-$ |
| $C_6H_5-$ | $-CH_2-$ | $H-$ | $CH_3-$ | m-$(CH_3)_2NC_6H_4-$ |
| $C_6H_5-$ | $CH_3\overset{\|}{C}H-$ | $CH_3-$ | $CH_3-$ | p-$(CH_3)_2NC_6H_4-$ |
| $C_6H_5-$ | $CH_3\overset{\|}{C}H-$ | $H-$ | $H-$ | p-$\phi C_6H_4-$ |
| $C_6H_5-$ | $-CH_2-$ | $H-$ | $CH_3-$ | m-$\phi C_6H_4-$ |
| $C_6H_5-$ | $-CH_2-$ | $H-$ | $n-C_3H_7-$ | m-$NCC_6H_4-$ |
| $C_6H_5-$ | $-CH_2-$ | $C_2H_5-$ | $H-$ | m-$NCC_6H_4-$ |
| $C_6H_5-$ | $-CH_2-$ | $H-$ | $H-$ | o-$HOC_6H_4-$ |
| $C_6H_5-$ | $CH_3CH_2\overset{\|}{C}H-$ | $H-$ | $CH_3-$ | p-$HOC_6H_4-$ |
| $C_6H_5-$ | $-CH_2-$ | $i-C_3H_7-$ | $H-$ | p-$HOC_6H_4-$ |
| $C_6H_5-$ | $CH_3\overset{\|}{C}H-$ | $H-$ | $H-$ | p-$CH_3CONHC_6H_4-$ |
| $C_6H_5-$ | $-CH_2-$ | $CH_3-$ | $CH_3-$ | p-$CH_3CONHC_6H_4-$ |
| $C_6H_5-$ | $-CH_2-$ | $H-$ | $H-$ | p-$C_2H_5CONHC_6H_4-$ |
| $C_6H_5-$ | $CH_3\overset{\|}{C}H-$ | $CH_3-$ | $C_2H_5-$ | p-$CH_3SC_6H_4-$ |
| $C_6H_5-$ | $CH_3\overset{\|}{C}H-$ | $CH_3-$ | $C_2H_5-$ | p-$CH_3SO_2C_6H_4-$ |
| $C_6H_5-$ | $CH_3CH_2\overset{\|}{C}H-$ | $CH_3-$ | $H-$ | m-$H_2NSO_2C_6H_4-$ |
| $C_6H_5-$ | $-CH_2-$ | $CH_3-$ | $CH_3-$ | p-$CH_3NHSO_2C_6H_4-$ |
| $C_6H_5-$ | $-CH_2-$ | $n-C_3H_7-$ | $H-$ | m-$(CH_3)_2NSO_2C_6H_4-$ |
| 4-$HOC_6H_4-$ | $-CH_2-$ | $C_2H_5-$ | $H-$ | p-$CH_3COC_6H_4-$ |
| 4-$HOC_6H_4-$ | $-CH_2-$ | $H-$ | $H-$ | m-$CH_3COC_6H_4-$ |

-continued

| Ar | A | $R_1$ | $R_2$ | $R_5$ |
|---|---|---|---|---|
| 4-$HOC_6H_4$— | $CH_3CH_2CH$— | H— | H— | m-$CH_3COC_6H_4$— |
| 4-$HOC_6H_4$— | —$CH_2$— | $CH_3$— | $CH_3$— | p-$(CH_3)_2NC_6H_4$— |
| 4-$HOC_6H_4$— | $CH_3CH$— | H— | H— | p-$\phi C_6H_4$— |
| 4-$HOC_6H_4$— | $CH_3CH$— | H— | n-$C_3H_7$— | m-$NCC_6H_4$— |
| 4-$HOC_6H_4$— | $CH_3CH_2CH$— | H— | $CH_3$— | p-$HOC_6H_4$— |
| 4-$HOC_6H_4$— | —$CH_2$— | H— | H— | p-$CH_3CONHC_6H_4$— |
| 4-$HOC_6H_4$— | $CH_3CH$— | $CH_3$— | $C_2H_5$— | p-$CH_3SO_2C_6H_4$— |
| 4-$HOC_6H_4$— | $CH_3CH$— | $CH_3$— | H— | m-$H_2NSO_2C_6H_4$— |
| 2-$C_4H_3S$— | —$CH_2$— | H— | H— | p-$CH_3COC_6H_4$— |
| 2-$C_4H_3S$— | $CH_3CH$— | H— | H— | p-$CH_3COC_6H_4$— |
| 2-$C_4H_3S$— | $CH_3CH$— | $CH_3$— | $CH_3$— | p-$(CH_3)_2NC_6H_4$— |
| 2-$C_4H_3S$— | $CH_3CH_2CH$— | H— | $CH_3$— | m-$\phi C_6H_4$— |
| 2-$C_4H_3S$— | —$CH_2$— | H— | n-$C_3H_7$— | m-$NCC_6H_4$— |
| 2-$C_4H_3S$— | —$CH_2$— | H— | H— | o-$HOC_6H_4$— |
| 2-$C_4H_3S$— | —$CH_2$— | $CH_3$— | $C_2H_5$— | p-$CH_3SC_6H_4$— |
| 2-$C_4H_3S$— | —$CH_2$— | $C_2H_5$— | H— | m-$H_2NSO_2C_6H_4$— |
| 2-$C_4H_3S$— | —$CH_2$— | H— | $CH_3$— | p-$CH_3NHSO_2C_6H_4$— |
| 2-$C_4H_3S$— | $CH_3CH$— | H— | H— | p-$C_2H_5CONHC_6H_4$— |
| 3-$C_4H_3S$— | —$CH_2$— | $CH_3$— | $CH_3$— | m-$(CH_3)_2NC_6H_4$— |
| 3-$C_4H_3S$— | $CH_3CH$— | $CH_3$— | H— | p-$\phi C_6H_4$— |
| 3-$C_4H_3S$— | $CH_3CH$— | $CH_3$— | H— | p-$CH_3COC_6H_4$— |
| 3-$C_4H_3S$— | $CH_3CH$— | $CH_3$— | $CH_3$— | p-$CH_3CONHC_6H_4$— |
| 3-$C_4H_3S$— | —$CH_2$— | H— | H— | m-$CH_3SC_6H_4$— |
| 3-$C_4H_3S$— | $CH_3CH_2CH$— | H— | $CH_3$— | m-$(CH_3)_2NC_6H_4$— |
| 3-$C_4H_3S$— | $CH_3CH_2CH$— | H— | $CH_3$— | p-$HOC_6H_4$— |
| 3-$C_4H_3S$— | $CH_3CH_2CH$— | H— | $C_2H_5$— | p-$CH_3SC_6H_4$— |
| 3-$C_4H_3S$— | $CH_3CH$— | H— | n-$C_3H_7$— | m-$NCC_6H_4$— |
| 3-$C_4H_3S$— | $CH_3CH$— | H— | $C_2H_5$— | p-$CH_3SO_2C_6H_4$— |
| 3-$C_4H_3S$— | $CH_3CH$— | H— | H— | m-$H_2NSO_2C_6H_4$— |
| 3-$C_4H_3S$— | —$CH_2$— | $C_2H_5$— | H— | m-$H_2NSO_2C_6H_4$— |
| 3-$C_4H_3S$— | —$CH_2$— | $C_2H_5$— | H— | m-$CH_3SC_6H_4$— |

EXAMPLE 27

The procedure of Example 23 is again repeated, starting with the appropriate D-6-[2-aryl-2-(aminoalkanoylamino)acetamido]penicillanic acid and imino ether, to give the following derivatives:

| Ar | A | $R_1$ | $R_2$ | $R_5$ |
|---|---|---|---|---|
| $C_6H_5$— | —$CH_2$— | H— | $CH_3$— | 3,5-$Cl_2C_6H_3$— |
| $C_6H_5$— | —$CH_2$— | $CH_3$— | $C_2H_5$— | 3,5-$F_2C_6H_3$— |
| $C_6H_5$— | $CH_3CH$— | H— | n-$C_3H_7$— | 2-F-5-$ClC_6H_3$— |
| $C_6H_5$— | $CH_3CH$— | H— | $CH_3$— | 3,5-$Cl_2C_6H_3$— |
| $C_6H_5$— | $CH_3CH$— | H— | $CH_3$— | 3-NC-5-$BrC_6H_3$— |
| $C_6H_5$— | $CH_3CH_2CH$— | H— | $CH_3$— | 3,5-$(CH_3S)_2C_6H_3$— |
| $C_6H_5$— | $CH_3CH_2CH$— | H— | $CH_3$— | 3,5-$Br_2C_6H_3$— |
| $C_6H_5$— | $CH_3CH$— | $CH_3$— | $CH_3$— | 3-$CH_3S$-4-$CH_3OC_6H_3$— |
| $C_6H_5$— | —$CH_2$— | i-$C_3H_7$— | H— | 3,5-$Cl_2C_6H_3$— |
| $C_6H_5$— | —$CH_2$— | i-$C_3H_7$— | H— | 3,4-$Cl_2C_6H_3$— |
| $C_6H_5$— | $CH_3CH_2CH$— | $CH_3$— | $CH_3$— | 3,5-$(CF_3)_2C_6H_3$— |
| 4-$HOC_6H_4$— | —$CH_2$— | H— | $CH_3$— | 3,5-$Cl_2C_6H_3$— |
| 4-$HOC_6H_4$— | —$CH_2$— | H— | $CH_3$— | 3,4-$F_2C_6H_3$— |
| 4-$HOC_6H_4$— | —$CH_2$— | H— | $C_2H_5$— | 3,4-$(CH_3O)_2C_6H_3$— |
| 4-$HOC_6H_4$— | —$CH_2$— | $CH_3$— | $CH_3$— | 3-NC-5-$BrC_6H_3$— |
| 4-$HOC_6H_4$— | —$CH_2$— | $CH_3$— | $CH_3$— | 3-Cl-4-$BrC_6H_3$— |
| 4-$HOC_6H_4$— | $CH_3CH$— | H— | $CH_3$— | 3-Cl-4-$BrC_6H_3$— |
| 4-$HOC_6H_4$— | $CH_3CH$— | H— | $CH_3$— | 3,5-$(CH_3S)_2C_6H_3$— |
| $HOC_6H_4$— | $CH_3CH$— | $CH_3$— | n-$C_3H_7$— | 2-F-5-$ClC_6H$— |
| 4-$HOC_6H_4$— | $CH_3CH_2CH$— | H— | $CH_3$— | 3,5-$Br_2C_6H_3$— |

| Ar | A | R₁ | R₂ | R₅ |
|---|---|---|---|---|
| 4-HOC₆H₄— | CH₃CH₂CH— | H— | C₂H₅— | 3,5-Br₂C₆H₃— |
| 4-HOC₆H₄— | CH₃CH₂CH— | CH₃— | CH₃— | 3-CH₃S-4-CH₃OC₆H₃— |
| 2-C₄H₃S— | —CH₂— | H— | H— | 3,5-Cl₂C₆H₃— |
| 2-C₄H₃S— | —CH₂— | H— | CH₃— | 3,4-F₂C₆H₃— |
| 2-C₄H₃S— | —CH₂— | H— | CH₃— | 3,5-Cl₂C₆H₃— |
| 2-C₄H₃S— | —CH₂— | CH₃— | CH₃— | 3-(CH₃)₂NSO₂—4-ClC₆H₃— |
| 2-C₄H₃S— | —CH₂— | C₂H₅— | CH₃— | 3,5-(i-C₃H₇O)₂—C₆H₃— |
| 2-C₄H₃S— | CH₃CH— | H— | n-C₃H₇— | 2-F-5-ClC₆H₃— |
| 2-C₄H₃S— | CH₃CH— | CH₃— | CH₃— | 3,5-(CH₃S)₂C₆H₃— |
| 2-C₄H₃S— | CH₃CH— | CH₃— | C₂H₅— | 3,4-(CH₃O)₂C₆H₃— |
| 2-C₄H₃S— | CH₃CH₂CH— | H— | CH₃— | 3,5-(CF₃)₂C₆H₃— |
| 2-C₄H₃S— | CH₃CH₂CH— | H— | CH₃— | 3,5-(C₂H₅O₂C)₂—C₆H₃— |
| 3-C₄H₃S— | —CH₂— | H— | CH₃— | 3,5-(C₂H₅O₂C)₂—C₆H₃— |
| 3-C₄H₃S— | —CH₂— | H— | CH₃— | 3-NC-5-BrC₆H₃— |
| 3-C₄H₃S— | —CH₂— | CH₃— | H— | 3-NC-5-BrC₆H₃— |
| 3-C₄H₃S— | CH₃CH— | CH₃— | C₂H₅— | 3,5-F₂C₆H₃— |
| 3-C₄H₃S— | CH₃CH— | CH₃— | C₂H₅— | 3,4-(CH₃O)₂C₆H₃— |
| 3-C₄H₃S— | —CH₂— | C₂H₅— | H— | 3,4-(CH₃O)₂C₆H₃— |
| 3-C₄H₃S— | CH₃CH₂CH— | H— | H— | 2-Cl-6-FC₆H₃— |
| 3-C₄H₃S— | CH₃CH₂CH— | H— | H— | 3,5-[(CH₃)₂NSO₂]—C₆H₃— |

EXAMPLE 28

6-[D-2-Phenyl-2-(3-amino-4-hydroxybenzimidoylaminoacetamido)acetamido]penicillanic acid sodium salt (Ar = C₆H₅; A = —CH₂—; R₁, R₂ = H; R₅ = 3—H₂N—4—HOC₆H₃)

To a suspension of 2.4 g. (6 m moles) of 6-[D-2-phenyl-2-(aminoacetamido)acetamido]penicillanic acid in 50 ml. of dimethylformamide is added 1.6 g. of ethyl 3-nitro-4-hydroxybenzimidate and 0.9 ml. of triethyl amine, and the mixture allowed to stir at room temperature for 4 hrs. The reaction mixture is filtered and the filtrate added dropwise to 800 ml. of diethyl ether. The resulting precipitate is filtered, washed with ether and triturated with chloroform to give 1.7 g. of 6-[D-2-phenyl-2-(3-nitro-4-hydroxybenzimidoylaminoacetamido)acetamido]penicillanic acid.

To 110 mg. (2.5 m moles) of sodium bicarbonate in 30 ml. of water is added 1.4 g. (2.5 m moles) of the above nitro compound, followed by 1.4 g. of 10% palladium on charcoal. The resulting mixture is shaken in a hydrogen atmosphere at room temperature at an initial pressure of 50 p.s.i. until the up-take of hydrogen ceases. The spent catalyst is filtered and the filtrate freeze dried to give 650 mg. of the desired penicillin as the sodium salt.

Nuclear magnetic resonance spectrum peaks (PPM; DMSO-D₆): 1.5(d,6H), 4.0(s,1H), 4.4(b,2H), 5.4(b,2H), 5.8(s,1H), and 6.8–7.8(m,8H).

EXAMPLE 29

Starting with the requisite imino ether and 6-[D-2-phenyl-2-(aminoalkanoylamino)acetamido]penicillanic acid, and employing the procedures of Example 28, the following compounds are prepared:

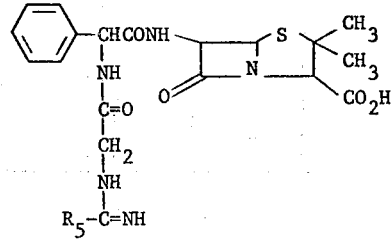

| R₅ | NMR⁺* |
|---|---|
| p-H₂NC₆H₄— | 1.45(d,6H), 3.95(s,1H), 4.25(b,2H), 5.35 (m,2H), 5.75(s,1H), and 7.3(b,9H). |
| m-H₂NC₆H₄— | 1.45(d,6H), 3.95(s,1H), 4.25(b,2H), 5.35 (m,2H), 5.75(s,1H), and 7.35(b,9H). |

⁺Nuclear magnetic resonance spectrum peaks - PPM; DMSO-D₆
*Not scanned about 500 Hz.

EXAMPLE 30

6-[D-2-Phenyl-2-(3-thenoimidoylaminoacetamido)acetamido]penicillanic acid sodium salt (Ar = C₆H₅; A = —CH₂—; R₆ = 3—C₄H₃S)

To 740 mg. (4.8 m moles) of ethyl 3-thenimidate in 7 ml. of dimethylformamide is added 1.6 g. (3.8 m moles) of 6-[D-2-phenyl-2-(aminoacetamido)acetamido]penicillanic acid sodium salt, and the mixture allowed to stir at room temperature for 1 hour. An additional 214 mg. of the penicillanic acid derivative is added and the stirring continued to an additional 2–3 hrs. The reaction mixture is filtered and the filtrate added dropwise to 75 ml. of diethyl ether with stirring. The product is filtered and dried in vacuo, 2.1g.

Nuclear magnetic resonance spectrum peaks (PPM; DMSO-D₆): 1.48(d,6H), 3.84(m,3H), 5.35(m,2H), and 7.33(m,8H).

The free acid is liberated by carefully adding dilute hydrochloric acid to a cooled aqueous solution of the above sodium salt to pH 6. The precipitate, zwitterionic form of the product is filtered and dried in vacuo.

EXAMPLE 31

Starting with the appropriate materials and employing the procedure of Example 30, the following penicillins or sodium salts thereof are synthesized:

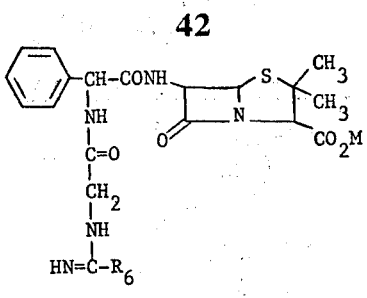

| $R_6$ | M | % Yield | NMR** |
|---|---|---|---|
| furyl (3-) | Na | 57 | 1.48(d,6H), 4.04(s,1H), 4.38 (m,2H), 5.37(m,2H), 7.33(m, 6H), and 7.90(m,2H). |
| isothiazolyl | Na | 79 | 1.48(d,6H), 3.67(m,2H), 4.19 (s,1H), 5.39(m,2H), 7.33(m, 5H), and 8.04(s,1H). |
| thiadiazolyl | Na | 65 | 1.50(d,6H), 3.30(m,2H), 4.30 (m,1H) 5.46(m,2H), 5.69(s, 1H), 7.43(m,5H), and 7.97 (m,1H). |
| isothiazolyl | Na | 85 | — |
| Br-thienyl | Na | 60 | — |
| Br-furyl | Na | 56 | *1.50(d,6H), 4.15(s,1H), 4.35 (m,2H), 5.44(m,2H), 5.65(s, 1H), and 7.39(m,7H). |
| Br-furyl | Na | 35 | 1.46(d,6H), 4.13(m,3H), 5.34 (m,2H), 6.86(d,1H), and 7.36 (m,6H). |
| Br-thienyl | Na | 76 | *1.51(d,6H), 4.17(s,1H), 4.34 (m,2H), 5.48(m,2H), 5.69(s, 1H), and 7.37(m,7H). |
| CH₃-thienyl | Na | 71 | *1.50(d,6H), 4.15(s,1H), 4.34 (m,2H), 5.46(m,2H), 5.67 (s, 1H), and 7.39(m,7H). |
| CH₃-thiazolyl | Na | 84 | 1.48(d,6H), 2.72(s,3H), 4.0 (s,1H), 4.38(m,2H), 5.37(m, 2H), 7.37(m,5H), and 7.97 (m,1H). |
| CH₃-isoxazolyl | Na | 67 | 1.48(d,6H), 2.35(s,3H), 4.35 m,3H), and 7.38(m,6H). |
| CH₃-isothiazolyl | Na | 85 | 1.46(d,6H), 3.76(m,2H), 4.0 (s,1H), and 7.34(m,6H). |
| CH₃-thienyl | Na | 77 | 1.46(d,6H), 2.21(s,3H), 4.0 (m,3H), 7.3(m,5H), and 7.79 (m,2H). |
| Cl-thienyl | Na | 88 | 1.47(d,6H), 3.76(m,2H), 4.09 (s,1H), 5.35(m,2H), and 7.33 (m,7H). |

-continued
| R₆ | M | % Yield | NMR** |
|---|---|---|---|
| 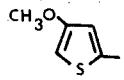 | Na | 85 | 1.48(d,6H), 3.78(s,5H), 4.06 (s,1H), 5.37(m,2H), 7.37(m, 6H), and 7.97(s,1H). |
| 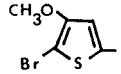 | Na | 74 | 1.48(d,6H), 3.88(s,5H), 4.12 (s,1H), 5.39(m,2H), 7.39)m, 5H), and 7.95(d,1H). |
| 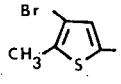 | Na | 79 | 1.48(d,6H), 2.40(s,3H), 3.94 (m,2H), 4.1(s,1H), 5.39(m, 2H), 7.39(m,5H), and 7.8)s, 1H). |
| 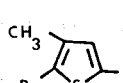 | Na | 79 | 1.46(d,6H), 2.14(s,3H), 3.98 (m,2H), 4.05(s,1H), 5.41(m, 2H), 7.34(m,5H), and 7.68 (s,1H). |
| 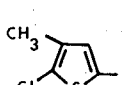 | Na | 82 | 1.48(d,6H), 2.16(s,3H), 4.0 (m,2H), 4.08(s,1H), 5.39)m, 2H), 7.3(m,5H), and 7.7(s, 1H). |
| 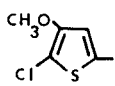 | Na | 86 | 1.48(d,6H), 3.88(s,5H), 4.09 (s,1H), 5.39(m,2H), 7.35(m, 5H), and 8.02(s,1H). |
| 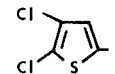 | Na | 76 | 1.5(d,6H), 3.84(m,2H), 4.15 (s,1H), 5.4(m,2H), 7.37(m, 5H), and 7.86(s,1H). |
| 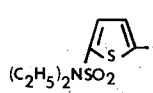 | Na | 74 | 1.07(t,6H), 1.48(d6H), 3.18 (q,4H), 3.92(m,2H), 4.06(s, 1H), 5.0(s,1H), 5.35(m,2H) 7.3(m,5H), and 8.2(q,2H). |
| 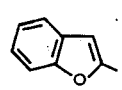 | Na | 97 | 1.48(d,6H), 4.05(m,1H), 4.3 (m,2H), 5.35(m,2H), 7.3(m, 9H), and 8.15(s,1H). |
| 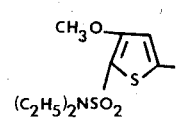 | Na | 78 | 1.08(t,6H), 1.48(d,6H), 3.26 (m,4H), 3.94(s,5H), 4.1(s, 1H), 5.39(m,2H), 7.33(m,5H), and 8.02(d,1H). |
| 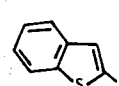 | Na | 91 | 1.46(d,6H), 2.14(s,3H), 3.98 (m,2H), 4.05(s,1H), 5.41(m, 2H), 7.34(m,5H), and 7,68(s, 1H). |
| 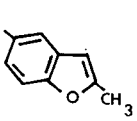 | H | 61 | 1.5(d,6H), 2.5(s,3H), 3.95(s, 1H), 4.35(b,2H), 5.4(m,2H), 5.8(s,1H), 6.8(s,1H), 7.45(b, 5H), 7.7(s,1H), and 8.0(s,1H). |
| 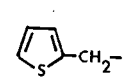 | H | 72 | 1.45(d,6H), 3.95(s,1H), 4.15 (b,4H), 5.35(m,2H), 5.75(s, 1H), and 7.4(b,8H). |
|  | H | 75 | 1.45(d,6H), 2.9(m,2H), 3.6(m, 4H), 3.95(s,1H), 4.2(b,2H), 5.4(m,2H), 5.75(s,1H), and 7.4(b,5H). |
| 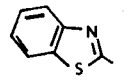 | H | 32 | 1.5(d,6H), 4.1(s,1H), 4.4(b, 2H), 5.5(b,2H), 5.8(s,1H), |

| $R_8$ | M | % Yield | NMR |
|---|---|---|---|
| | | | 7.3–7.9(b,7H), and 8.25(b, 2H). |
| 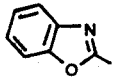 | H | 36 | 1.5(d,6H), 4.0(s,1H), 4.3(b, 2H), 5.45(b,2H), 5.8(s,1H), and 7.15–8.1(m,9H). |
|  | H | 47 | 1.5(d,6H), 3.9(s,1H), 4.2(b, 2H), 5.4(b,2H), 5.8(s,1H), 7.5(b,5H), and 7.9(s,1H). |
|  | Na | 49 | 1.48(d,6H), 3.83(m,2H), 3.97 (s,1H), 5.37(m,2H), 7.35(m, 5H), and 7.97(s,1H). |
|  | Na | 70 | 1.45(d,6H), 3.93(b,2H), 5.18 (m,2H), 7.33(m,5H), and 7.95 (m,2H). |
| 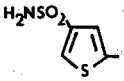 | Na | 73 | 1.45(d,6H), 4.08(b,2H), 4.22 (s,1H), 5.38(m,2H), 7.35(m, 5H), and 8.0(m,2H). |
| 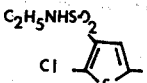 | Na | 69 | 1.02(t,3H), 1.47(d,6H), 3.73 (b,2H), 3.95(m,3H), 5.35(m, 2H), 7.33(m,5H), and 7.95(b, 1H). |
| 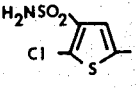 | Na | 92 | 1.45(d,6H), 3.73(b,2H), 3.98 (s,1H), 5.33(m,2H), 7.33(m, 5H), and 7.93(s,1H). |
|  | H | 16 | 1.5(d,6H), 3.8(s,2H), 4.1(s, 1H), 5.0–6.0(m,14H), and 6.9–8.2(m,12H). |
| 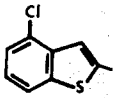 | Na | 68 | 1.50(d,6H), 4.02(s,1H), 5.4 (m,2H), 7.4(m,7H), 7.98(s, 1H), and 8.22(s,1H). |
| 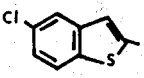 | Na | 60 | 1.50(d,6H), 4.0(s,1H), 5.75 (m,2H), 7.33(m,8H), and 7.95(s,1H). |
| 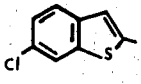 | Na | 77 | 1.50(d,6H), 3.83(m,2H), 4.0 (s,1H), 5.38(m,2H), 7.81(bs, 1H), 7.97(bs,1H), and 8.12 (bd,2H). |
| 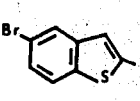 | Na | 68 | 1.48(d,6H), 5.37(m,2H), 7.35 (m,5H), and 7.98(m,4H). |
| 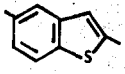 | Na | 66 | 1.50(d,6H), 5.37(m,2H), 7.37 (m,5H), and 8.0(m,4H). |
| 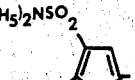 | Na | 69 | 1.1(t,6H), 1.5(d,6H), 3.95 (b,2H), 4.18(b,1H), 5.35(m, 2H), 7.35(m,5H), and 7.95 (s,1H). |

| $R_6$ | M | % Yield | NMR+* |
|---|---|---|---|
|  | Na | 96 | 1.47(d,6H), 4.0(m,2H), 4.12 (s,1H), 5.35(m,2H), 7.33(m, 5H), and 7.87(m,2H). |
|  | H | 32 | 1.5(d,6H), 3.7(s,2H), 4.1(s, 1H), 5.8(m,3H), 7.4(m,5H), and 7.7(s,1H). |

+Nuclear magnetic resonance spectrum peaks - PPM; DMSO-D$_6$; not scanned beyond 500 Hz.
*Solvent CD$_3$OD.

EXAMPLE 32

6-[D-2-Phenyl-2-(2-{2-thenoimidoyl}aminopropionamido)acetamido]penicillanic acid (Ar = C$_6$H$_5$; A = CH$_3$CH—; R$_6$ = 2-C$_4$H$_3$S)

A mixture of 4.2 g. (0.01 mole) of 6-[D-2-phenyl-2-(2-aminopropionamido)acetamido]penicillanic acid and 1.41 g. (0.01 mole) of methyl 2-thenimidate in 15 ml. of dimethylformamide is allowed to stir at room temperature for 2 hrs. Triethylamine (2.4 ml.) is added, and the mixture added slowly to 150 ml. of chloroform with rapid stirring. The solids are filtered and the filtrate diluted with an equal volume of hexane. The product is filtered, washed successively with methylene chloride-hexane, methylene chloride and ether, and dried in vacuo, 1.62 g.

Nuclear magnetic resonance spectrum peaks (PPM; DMSO-D$_6$ and D$_2$O) 1.5(m9H), 5.5(m,3H), 7.4(s,7H), and 8.0(s,1H).

EXAMPLE 33

Employing the procedure of Example 32 and starting with the appropriate reagents, the following penicillins are synthesized:

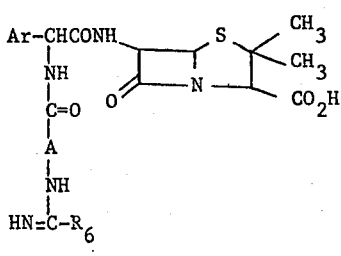

| Ar | A | R$_6$ |
|---|---|---|
| C$_6$H$_5$— | CH$_3$CH— | 2-furyl |
| C$_6$H$_5$— | CH$_3$CH— | 4,5-dibromo-2-thienyl |
| C$_6$H$_5$— | CH$_3$CH— | 5-bromo-2-thienyl |
| C$_6$H$_5$— | CH$_3$CH— | 5-bromo-3-furyl |
| C$_6$H$_5$— | CH$_3$CH$_2$CH— | 2-thienyl |
| C$_6$H$_5$— | CH$_3$CH$_2$CH— | 2-furyl |
| C$_6$H$_5$— | CH$_3$CH$_2$CH— | 5-bromo-4-methyl-2-furyl |
| 4-HOC$_6$H$_4$— | CH$_3$CH— | 5-chloro-4-methyl-2-thienyl |
| 4-HOC$_6$H$_4$— | CH$_3$CH— | 2-furyl |
| 4-HOC$_6$H$_4$— | CH$_3$CH— | 5-bromo-2-thienyl |
| 4-HOC$_6$H$_4$— | CH$_3$CH— | 2-thienyl |
| 4-HOC$_6$H$_4$— | CH$_3$CH— | 4-methoxy-2-thienyl |
| 4-HOC$_6$H$_4$— | CH$_3$CH$_2$CH— | 5-diethylsulfamoyl-2-thienyl |
| 4-HOC$_6$H$_4$— | CH$_3$CH$_2$CH— | 5-chloro-4-sulfamoyl-2-thienyl |
| 4-HOC$_6$H$_4$— | CH$_3$CH$_2$CH— | 2-thenyl |
| 4-HOC$_6$H$_4$— | CH$_3$CH$_2$CH— | 2-thienyl |
| 2-C$_4$H$_3$S— | CH$_3$CH— | 2-thienyl |
| 2-C$_4$H$_3$S— | CH$_3$CH— | 5-diethylsulfamoyl-2-thienyl |
| 2-C$_4$H$_3$S— | CH$_3$CH— | 4,5-dichloro-2-thienyl |
| 2-C$_4$H$_3$S— | CH$_3$CH— | 4-chloro-2-thienyl |
| 2-C$_4$H$_3$S— | CH$_3$CH$_2$CH— | 5-isothiazolyl |
| 2-C$_4$H$_3$S— | CH$_3$CH$_2$CH— | 2-methyl-4-thiazolyl |
| 2-C$_4$H$_3$S— | CH$_3$CH$_2$CH— | 4-methyl-2-thiazolyl |
| 2-C$_4$H$_3$S— | CH$_3$CH$_2$CH— | 4-methyl-2-thienyl |
| 3-C$_4$H$_3$S— | CH$_3$CH— | 5-bromo-2-thienyl |
| 3-C$_4$H$_3$S— | CH$_3$CH— | 2-thienyl |
| 3-C$_4$H$_3$S— | CH$_3$CH— | 2-furyl |
| 3-C$_4$H$_3$S— | CH$_3$CH— | 5-chloro-3-sulfamoyl-2-thienyl |
| 3-C$_4$H$_3$S— | CH$_3$CH— | 3-thenyl |
| 3-C$_4$H$_3$S— | CH$_3$CH$_2$CH— | 3-thenyl |
| 3-C$_4$H$_3$S— | CH$_3$CH$_2$CH— | 2-furyl |
| 3-C$_4$H$_3$S— | CH$_3$CH$_2$CH— | 4-(1,2,3-thiadiazolyl) |
| 3-C$_4$H$_3$S— | CH$_3$CH$_2$CH— | 4-isoxazolyl |

EXAMPLE 34

6-[D-2-Phenyl-2-(2-{3-pyridoimidoyl}aminopropionamido)acetamido]penicillanic acid (Ar = C$_6$H$_5$; A = CH$_3$CH—; R$_6$ = 3-C$_5$H$_4$N)

To a solution of 4.20 g. (0.01 mole) of 6-[D-2-phenyl-2-(2-aminopropionamido)acetamido]penicillanic acid in 15 ml. of dimethylformamide is added 2.2 g. of methyl 3-pyridoimidate and the resulting reaction mixture allowed to stir for 2.5 hrs. Triethylamine (2.4 ml.) is added, and the solution added to 150 ml. of chloroform with rapid stirring. The mixture is filtered and the filtrate added to an equal volume of hexane. The precipitate is filtered, washed with methylene chloride-hexane, methylene chloride and diethyl ether and, finally, dried in vacuo.

Nuclear magnetic resonance spectrum peaks (PPM; DMSO-$D_6$ and $D_2O$): 1.55(d,6H), 1.6(d,3H), 5.5(m,3H), 7.4(s,6H), 8.1(m,1H), and 8.9(m,2H).

EXAMPLE 35

6-[D-2-Phenyl-2-(2-{4-pyridoimidoyl}aminopropionamido)-acetamido]penicillanic acid $(Ar = C_6H_5; A = CH_3CH-; R_9 = 4-C_5H_4N)$.

In a manner similar to that of Example 34, using the requisite starting reagents, the desired product is prepared.

Nuclear magnetic resonance spectrum peaks (PPM; $D_2O$) 1.45(d,6H), 1.65(d,3H), 4.0(m,1H), 4.2(s,1H), 5.5(m,3H), 7.4(s,5H), 7.7(d,2H), and 8.8 (d,2H).

EXAMPLE 36

6-[D-2-Phenyl-2-(4-pyridoimidoylaminoacetamido)-acetamido]penicillanic acid (Ar = $C_6H_5$; A = —$CH_2$—; $R_9 = 4$—$C_5H_4N$)

To a cooled mixture of 114.3 g. (0.281 mole) of 6-[D-2-phenyl-2-(aminoacetamido)acetamido]penicillanic acid in 200 ml. of dimethylformamide is added 42.16 g. (0.31 mole) of methyl 4-pyridyimidate, and the resulting mixture allowed to stir in the cold for 15 min. The resulting solution is allowed to warm to room temperature and is stirred for 1 hr. 45 min. Triethylamine (48.5 g.) is added, and, after stirring for 10 min., the solution is added dropwise to 4 l. of chloroform.

The precipitated solids are removed and the filtrate added to 6 l. of hexane. The solids formed are filtered, washed successively with chloroform and ether and dried under reduced pressure to give 61 g. of the desired product.

To further purify the product, it is dissolved in 200 ml. of dimethylformamide containing 12.1 g. of triethylamine, which is then filtered and added dropwise into 2 l. of chloroform. A small amount of solids are removed and the chloroform-dimethylformamide filtrates added to 6 l. of hexane. The product is filtered, dried (41.3 g.) and dissolved in 200 ml. of dimethylformamide. The resulting solution is added to 2.5 l. of chloroform and the precipitated product filtered, triturated with 3 × 500 ml. of methylene chloride and dried, 36.2 g.

Nuclear magnetic resonance spectrum peaks (PPM; DMSO-$D_6$) 1.5(d,6H), 4.2(s,3H), 5.2–5.6(m,2H), 5.85(d,1H), 7.4(s,5H), 7.8(d,2H), 8.35(s,4H), 8.9 (d,2H), and 9.15(t,2H).

EXAMPLE 37

The procedure of Example 36 is repeated, starting with the appropriate reagents, to provide the following compounds:

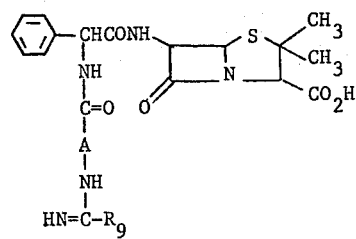

| $R_9$ | A | NMR** |
|---|---|---|
| 2-pyridyl | —$CH_2$— | 1.5(d,6H), 3.9(s,3H), 4.0–6.0(s,6H), 5.35(m,2H), 5.8 (d,1H), 7.35(s,6H), 7.7–8.4 (m,2H), 8.65(d,1H), 8.9(d, 1H), and 9.15(d,1H). |
| 3-pyridyl | —$CH_2$— | 1.5(d,6H), 3.95(s,1H), 4.2 (s,2H), 5.35(m,2H), 5.75(d, 1H), 7–7.6(m,6H), 8–8.2(m, 1H), and 8.65–9.3(m,7H). |
| 4-pyridyl N-oxide | —$CH_2$— | 1.5(d,6H), 4.2(s,3H), 5.45 (m,2H), 5.9(d,1H), 7.45(s, 5H), 7.9(d,5H), 8.45(d,2H), and 9.45(q,2H). |
| 4-pyridyl | —$(CH_2)_2$— | 1.4(d,6H), 2.7(t,2H), 3.7 (t,2H), 4.0(s,1H), 5.4(m, 3H), 7.4(s,5H), 7.7(d,2H), and 8.8(d,2H). |
| 4-pyridyl N-oxide | —$CH_3CH$— | 1.3(m,9H), 5.3(m,3H), 7.2 (s,5H), 7.6(d,2H), and 8.2 (d,2H). |

| $R_9$ | A | -continued NMR** |
|---|---|---|
|  | $(CH_3)_2CHCH-$ | 1.0(d,6H), 1.5(d,6H), 5.5 (m,3H), 7.4(s,5H), 7.7(d, 2H), and 8.8(d,2H). |
|  | —CH₂— | 1.45(d,6H), 4.32(m,3H), and 7.60(m,8H). |
|  | —CH₂— | 1.46(d,6H), 4.05(m,3H), 5.34 (m,2H), 7.34(m,5H), 8.45(s, 1H), and 8.95(d,2H). |
|  | —CH₂— | 1.46(d,6H), 4.02(s,1H), 4.27 (m,2H), 7.30(m,5H), 8.14(m, 1H), and 8.85(m,2H). |
|  | —CH₂— | 1.45(d,6H), 3.95(b,3H), 4.2 (b,1H), 5.35(m,2H), 5.75(s, 1H), 7.35(b,6H), 8.0(m,1H), and 8.5(m,2H). |
|  | —CH₂— | 1.5(d,6H), 3.95(s,1H), 4.25 (b,2H), 5.4(b,2H), 5.8(s,1H), 6.25(b,1H), and 7.25(b,7H). |
|  | —CH₂— | 1.5(d,6H), 4.0(s,1H), 4.4 (b,2H), 5.4(b,2H), 5.7(s, 1H), 7.5(b,5H), 8.1(m,1H), and 9.6(m,2H). |
|  | —CH₂— | 1.5(d,6H), 4.0(s,1H), 4.4 (b,2H), 5.4(b,2H), 5.75(s, 1H), 7.45(b,5H), 8.0(m,1H), 8.45(m,1H), amd 9.5(m,1H). |
|  | —CH₂— | 1.5(d,6H), 4.2(s,1H), 4.5 (b,2H), 5.5(s,2H), 5.6(s, 1H), 7.45(s,7H), 9.0(m,2H), and 9.35(s,1H). |
| 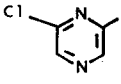 | —CH₂— | 1.5(d,6H), 3.9(s,1H), 4.2 (b,2H), 5.45(b,2H), 5.8(s, 1H), 7.5(b,5H), 9.1(s,1H), and 9.35(s,1H). |
|  | —CH₂— | 1.5(d,6H), 4.2(s,1H), 4.6 (b,2H), 5.45(s,2H), 5.6(s, 1H), 7.4(s,5H), 7.75(m,2H), and 8.8(d,2H). |
|  | —CH₂— | 1.4(d,6H), 4.2(s,3H), 5.5 (m,2H), 5.9(d,1H), 6.4–7.2 (s,6H), 7.3–7.8(s,5H), 9.2 (t,2H), 9.3(s,2H), and 9.5 (s,1H). |
|  | —CH₂— | 1.5(d,6H), 4.1(s,1H), 5.6 (m,3H), 7.5(s,5H), 8.3(d, 1H), 9.1(d,1H), and 9.4(s, 1H). |
| 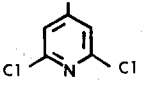 | —CH₂— | 1.5(d,6H), 3.9(s,2H), 4.1 (s,1H), 5.4(m,2H), 5.8(d, 1H), 7.0–7.9(s,13H), 7.95 (s,2H), 8.85(d,1H), and 9.25(d,1H). |

| R₉ | A | NMR⁺* |
|---|---|---|
| 2-benzimidazolyl | —CH₂— | 1.5(d,6H), 4.1(s,1H), 4.25 (b,2H), 5.45(m,2H), 5.8(s, 1H), 7.5–7.75(b,9H). |
| 2-(1-pyrrolinyl) | —CH₂— | 1.45(d,6H), 2.2(s,4H), 3.6 (b,2H), 3.9(s,1H), 4.2(b, 2H), 5.35(m,2H), 5.7(s,1H), and 7.35(b,5H). |
| 5-methyl-2-methylbenzimidazolyl | —CH₂— | 1.5(d,6H), 2.6(s,3H), 3.7 (s,1H), 4.35(b,2H), 5.45(s, 2H), 5.7(s,1H), and 7.5–8.1 (m,10H). |
| 2-imidazo[1,2-a]pyridyl | —CH₂— | 1.5(d,6H), 4.0(s,1H), 4.45 (b,2H), 5.45(s,2H), 5.8(s, 1H), 7.45(m,8H), and 8.65 (b,2H). |
| 2-quinoxalinyl | —CH₂— | 1.5(d,6H), 4.0(s,1H), 4.4 (b,2H), 5.5(b,2H), 5.75 (s,1H), 7.5(b,5H), 8.2(b, 4H), and 9.4(s,1H). |
| methylquinoxalinyl | —CH₂— | 1.5(d,6H), 4.0(s,1H). 4.3 (b,2H), 5.45(b,2H), 5.8(s, 1H), 7.5(b,5H), 8.3(b,2H), 8.6(b,1H), and 9.2(b,2H). |
| 4-imidazolyl | —CH₂— | 1.5(d,6H), 3.95(s,1H), 4.3 (b,2H), 5.45(b,2H), 5.8(s, 1H), 7.5(b,5H), 8.0(s,1H), and 8.35(b,2H). |
| 5-chloro-2-benzimidazolyl | —CH₂— | 1.5(d,6H), 4.0(s,1H), 4.2 (b,2H). 5.4(b,2H), 5.8(s, 1H), and 7.2–7.9(m,8H). |
| 5-bromo-2-benzimidazolyl | —CH₂— | 1.5(d,6H), 4.0(s,1H), 4.3 (b,2H), 5.4(b,2H), 5.75(s, 1H), and 7.1–8.1(m,8H). |
| 4-methylisoquinolinyl | —CH₂— | 1.5(d,6H), 3.7(s,2H), 4.1 (s,1H), 5.2–6.5(m,13–14H), 7.5(s,1H), and 7.8–9.7(m,8H). |
| 3-methylquinolinyl | —CH₂— | 1.3(s,6H), 3.6(s,2H), 4.0 (s,1H), 4.8–6.2(m,22H), 7.0– 7.8(s,6H), 7.8–8.7(m,5H), and 9.05(s,2H). |
| 4-methylquinolinyl | —CH₂— | 1.2(d,6H), 3.4(s,2H), 3.8 (s,1H), 5.0–5.3(s,11H), 5.5 (s,1H), 6.8–8.2(m,11H), and 8.7(s,2H). |
| 6-methylquinolinyl | —CH₂— | 1.4(d), 4.0(s), 4.4(m), 5.0– 6.2(b), 7.4(s), 8.2(s), and 8.6(m). |

⁺Nuclear magnetic resonance spectrum peaks; PPM-DMSO-D₆
*Not scanned above 500 Hz

EXAMPLE 38

The synthetic procedure of Example 36 is again repeated, starting with the appropriate imino ether and 6-[D-2-aryl-2-(aminoalkanoylamino)acetamido]-penicillanic acid, to provide the following penicillins:

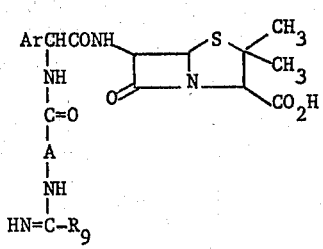

| Ar | A | $R_9$ |
|---|---|---|
| $C_6H_5-$ | $-CH_2-$ | 2-pyrryl |
| $C_6H_5-$ | $-CH_2-$ | 3-pyrryl |
| $C_6H_5-$ | $-CH_2-$ | 2-chloro-4-pyridyl |
| $C_6H_5-$ | $-CH_2-$ | 3-pyridyl-N-oxide |
| $C_6H_5-$ | $CH_3\overset{\mid}{C}H-$ | 2-fluoro-4-pyridyl |
| $C_6H_5-$ | $CH_3\overset{\mid}{C}H-$ | 2-pyrimidyl |
| $C_6H_5-$ | $CH_3\overset{\mid}{C}H-$ | 4-picolyl |
| $C_6H_5-$ | $CH_3CH_2\overset{\mid}{C}H-$ | 4-picolyl |
| $C_6H_5-$ | $CH_3CH_2\overset{\mid}{C}H-$ | 2-benzimidazolyl |
| $4\text{-}HOC_6H_4-$ | $-CH_2-$ | 4-pyridyl |
| $4\text{-}HOC_6H_4-$ | $-CH_2-$ | 3-pyridyl |
| $4\text{-}HOC_6H_4-$ | $-CH_2-$ | 2-benzimidazolyl |
| $4\text{-}HOC_6H_4-$ | $CH_3\overset{\mid}{C}H-$ | 2-fluoro-4-pyridyl |
| $4\text{-}HOC_6H_4-$ | $CH_3\overset{\mid}{C}H-$ | 3-pyrryl |
| $4\text{-}HOC_6H_4-$ | $CH_3\overset{\mid}{C}H-$ | 2,6-dichloro-4-pyridyl |
| $4\text{-}HOC_6H_4-$ | $CH_3\overset{\mid}{C}H-$ | 3-pyridyl-N-oxide |
| $4\text{-}HOC_6H_4-$ | $CH_3\overset{\mid}{C}H-$ | 4-pyridyl-N-oxide |
| $4\text{-}HOC_6H_4-$ | $CH_3CH_2\overset{\mid}{C}H-$ | 4-picolyl |
| $4\text{-}HOC_6H_4-$ | $CH_3CH_2\overset{\mid}{C}H-$ | 3-pyrryl |
| $2\text{-}C_4H_3S-$ | $-CH_2-$ | 3-pyridyl |
| $2\text{-}C_4H_3S-$ | $-CH_2-$ | 4-pyridyl |
| $2\text{-}C_4H_3S-$ | $-CH_2-$ | 4-pyridyl-N-oxide |
| $2\text{-}C_4H_3S-$ | $-CH_2-$ | 2-benzimidazolyl |
| $2\text{-}C_4H_3S-$ | $-CH_2-$ | 2,6-dichloro-4-pyridyl |
| $2\text{-}C_4H_3S-$ | $CH_3\overset{\mid}{C}H-$ | 4-pyridyl |
| $2\text{-}C_4H_3S-$ | $CH_3\overset{\mid}{C}H-$ | 4-pyridyl-N-oxide |
| $2\text{-}C_4H_3S-$ | $CH_3\overset{\mid}{C}H-$ | 2-pyrazinyl |
| $2\text{-}C_4H_3-$ | $CH_3CH_2\overset{\mid}{C}H-$ | 2-pyrazinyl |
| $2\text{-}C_4H_3S-$ | $CH_3CH_2\overset{\mid}{C}H-$ | 4-pyridyl |
| $3\text{-}C_4H_3S-$ | $-CH_2-$ | 2-fluoro-4-pyridyl |
| $3\text{-}C_4H_3S-$ | $-CH_2-$ | 2-chloro-4-pyridyl |
| $3\text{-}C_4H_3S-$ | $-CH_2-$ | 4-pyridyl |
| $3\text{-}C_4H_3S-$ | $-CH_2-$ | 4-pyridyl-N-oxide |
| $3\text{-}C_4H_3S-$ | $-CH_2-$ | 2-benzimidazolyl |
| $3\text{-}C_4H_3S-$ | $CH_3\overset{\mid}{C}H-$ | 2-benzimidazolyl |
| $3\text{-}C_4H_3S-$ | $CH_3\overset{\mid}{C}H-$ | 2-pyrryl |
| $3\text{-}C_4H_3S-$ | $CH_3\overset{\mid}{C}H-$ | 4-picolyl |
| $3\text{-}C_4H_3S-$ | $CH_3CH_2\overset{\mid}{C}H-$ | 2,6-dichloro-4-pyridyl |
| $3\text{-}C_4H_3S-$ | $CH_3CH_2\overset{\mid}{C}H-$ | 3-pyridazinyl |
| $3\text{-}C_4H_3S-$ | $CH_3CH_2\overset{\mid}{C}H-$ | 2-pyrazinyl |

EXAMPLE 39

6-[D-2-Phenyl-2-(methoxyacetimidoylaminoacetamido)acetamido]penicillanic acid (AR = $C_6H_5$; A = $-CH_2-$; $R_{10}$ = $OCH_3$)

A mixture of 2.03 g. (5 m moles) of 6-[D-2-(aminoacetamido)acetamido]penicillanic acid, 845 mg. (5 m moles) of ethyl methoxyacetthioimidate hydrochloride and 1.4 g. (10 m moles) of triethylamine in 40 ml. of dimethylformamide is allowed to stir at room temperature for 2 hrs. The reaction mixture is filtered and the filtrate added to 1 l. of diethyl ether. The precipitated product is filtered, washed with acetone and chloroform, and dried in vacuo, 1.5 g.

Nuclear magnetic resonance spectrum peaks (PPM; DMSO-$D_6$ and $D_2O$) 1.45(d,6H), 3.35(s,3H), 3.95(s,1H), 4.3(b,4H), 5.35(m,2H), 5.7(s,1H), and 7.35 (b,5H).

EXAMPLE 40

By substituting the appropriate imino ether or thio ether for ethyl methoxyacetthioimidate and starting with 6-[D-2-phenyl-2-(aminoacetamido)acetamido]-penicillanic acid, and employing the synthetic procedure of Example 39, the following congeners are prepared:

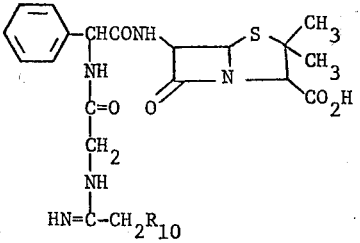

| $R_{10}$ | % Yield | NMR** |
|---|---|---|
| $CH_3S-$ | 73 | 1.45(d,6H), 2.2(s,3H), 3.6(b,2H), 3.9(s,1H), 4.2(b,2H), 5.35 (m,2H), 5.7(s,1H), and 7.35 (b,5H). |
| $CH_3SO_2-$ | 72 | 1.5(d,6H), 3.3(s,3H), 4.0(s)+ 4.1(b)+4.5(b)5H, 5.35(m,2H), 5.8(s,1H), and 7.4(b,5H). |
| $CH_3SO-$ | 76 | 1.5(d,6H), 2.2(s,3H), 3.6(b,2H), 3.95(s,1H), 4.2(b,2H), 5.4(m,2H), 5.8(s,1H), and 7.4 (b,5H). |
| $C_6H_5CH_2S-$ | 74 | 1.45(d,6H), 3.65(b,2H), 3.95 (b,3H), 4.15(b,2H), 5.35(m,7H), 5.8(s,1H), and 7.35(b,10H). |
| $p\text{-}CH_3OC_6H_4S-$ | 75 | 1.45(d,6H), 3.7(s)+3.9(b)+ 3.7(b)8H, 5.3(m,2H), 5.75(s,1H), 6.85(d,2H), and 7.3(m,9H). |
| $p\text{-}CH_3C_6H_4S-$ | 42 | 1.5(d,6H), 2.25(s,3H), 3.9 (s)+4.0(b)+4.1(b)5H, 5.35(m,2H), 5.75(s,1H), and 7.3(m,9H). |
| $p\text{-}ClC_6H_4S-$ | 74 | 1.45(d,6H), 4.15(b,5H), 5.35 (m,2H), 5.75(s,1H), and 7.35 (b,9H). |
| $p\text{-}BrC_6H_4S-$ | 69 | 1.45(d,6H), 3.95(s,1H), 4.1(b,4H), 5.35(m,2H), 5.75(s,1H), and 7.35(m,9H). |
| $3,5\text{-}Cl_2C_6H_3O-$ | 52 | 1.45(d,6H), 4.0(s,1H), 4.15 (b,2H), 5.05(b,2H), 5.4(m,2H), 5.8(s,1H), and 7.3(m,8H). |
| $p\text{-}ClC_6H_4O-$ | 59 | 1.45(d,6H), 4.01(s,1H), 4.25 (b,2H), 5.0(b,2H), 5.35(m,2H), 5.75(s,1H), and 7.25(m,9H). |
| $3,4\text{-}Cl_2C_6H_3O-$ | 18 | 1.35(d,6H), 3.84(s,1H), 4.04 (s,2H), 4.9(s,2H), 5.1+5.6(m,3H), and 7.2(m,8H). |
| $Cl-$ | 70 | 1.45(d,6H), 3.95(s)+4.05(b)3H, 4.4(b,2H), 5.35(m,2H), 5.75 (s,1H), and 7.3(b,5H). |
| $HO-$ | 82 | 1.5(d,6H), 3.9(s,1H), 4.3(b,4H), 5.3(m,2H), 5.7(s,1H), and 7.3(b,5H). |
| $F-$ | 77 | 1.5(d,6H), 3.95(s,1H), 4.15 (b,2H), 5.35(d,2H), 5.4(m,2H), 5.75(s,1H), and 7.35(b,5H). |
| $CH_3NH-$ | 76 | 1.45(d,6H), 2.25(s,3H), 3.95 (s)+4.2(b)5H, 5.35(m,2H), 5.7 (s,1H), and 7.4(b,5H). |
| $CH_3CONH-$ | 83 | 1.45(d,6H), 2.0(s,3H), 3.95 (s,1H), 4.2(b,4H), 5.35(m,2H), 5.75(s,1H), and 7.3(b,5H). |
| $C_6H_5CONH-$ | 75 | 1.45(d,6H), 3.95(s,1H), 4.25 (b,4H), 5.35(m,2H), 5.75(s,1H), 7.4(m,8H), and 7.95(m,2H). |
| $p\text{-}ClC_6H_4CONH-$ | 70 | 1.45(d,6H), 3.9(s,1H), 4.25(b,4H), 5.4(m,2H), 5.75(s,1H), 7.35(m,7H), and 8.0(d,2H). |
| $3,4\text{-}Cl_2C_6H_3-$ | 70 | 1.45(d,6H), 3.9(s,1H), 4.25(b, |

| $R_{10}$ | % Yield | NMR** |
|---|---|---|
| CONH— | | 4H), 5.35(m,2H), 5.75(s,1H), 7.35(b,5H), 7.8(m,2H), and 8.2 (s,1H). |
| $C_6H_5SO_2NH$— | 67 | 1.45(d,6H), 3.9(b,5H), 5.35(m, 2H), 5.7(s,1H), and 7.5(b,m, 10H). |
| $C_6H_5CH_2O\overset{O}{\overset{\|}{C}}NH$— | 77 | 1.45(d,6H), 3.95(s,1H), 4.1(b, 4H), 5.05(s,2H), 5.35(m,2H), 5.75(s,1H), and 7.35(b,10H). |
| $C_6H_5CO_2$— | 78 | 1.45(d,6H), 3.9(s,1H), 4.2(b, 2H), 5.3(b,4H), 5.75(s,1H), 7.4(b,8H), and 8.2(b,2H). |
| 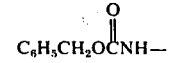CONH- | 73 | 1.45(d,6H), 3.95(s,1H), 4.2(b, 4H), 5.35(m,2H), 5.75 (s,1H), 7.3(b,6H), and 7.9(m,2H). |
| p-$ClC_6H_4NH$— | 73 | 1.45(d,6H), 3.95(s,1H), 4.2(b, 4H), 5.35(m,2H), 5.75(s,1H), 6.65(d,2H), and 7.1(d)+7.3 (b)7H. |
| 3,4,-$Cl_2C_6H_3NH$— | 57 | 1.5(d,6H), 4.0(b,3H), 4.2(b, 2H), 5.4(c,2H), 5.8(s,1H), 7.5(b,6H), and 8.0(s,2H). |
| $C_6H_5CH_2O_2CNHCH_2$—CONH— | 84 | 1.45(d,6H), 3.75(b)+3.9(s)+ 4.15(b)7H, 5.0(s,2H), 5.35 (m,2H), 5.75(s,1H), and 7.35 (b,10H). |

*Nuclear magnetic resonance spectrum peaks; PPM-DMSO-$D_6$
*Not scanned above 500 Hz

EXAMPLE 41

6-[D-2-Phenyl-2-(aminoacetimidoylaminoacetamido)- acetamido]penicillanic acid (Ar = $C_6H_5$; A = —$CH_2$—; $R_{10}$ = $H_2N$—)

A mixture of 2.5 g. (4.2 m moles) of 6-[D-2-phenyl-2-(benzyloxycar- bonylaminoacetimidoylaminoacetamido)acetamido]-penicillanic acid and 2.5 g. of 10% palladium-on-charcoal in 90 ml. of methanol-water is shaken in a hydrogen atmosphere at an initial pressure of 40 p.s.i. After 45 min. the reaction is complete, and the mixture is filtered through super cel. The filtrate is concentrated under reduced pressure until the methanol is removed. The residual solution is adjusted to pH 5 and freeze dried to give 1.1 g. of the desired product.

Nuclear magnetic resonance spectrum peaks (PPM; DMSO-$D_6$ and $D_2O$): 1.45(d,6H), 3.55(b,2H), 3.95(s,1H), 4.2(b,2H), 5.35(m,2H), 5.75(s,1H), and 7.35(b,5H).

In a similar manner, starting with the appropriate benzyloxycarbonyl derivative is prepared 6-[D-2-phenyl-2-(glycylaminoacetimidoylaminoacetamido)- acetamido]penicillanic acid (Ar = $C_6H_5$; A = —$CH_2$—; $R_{10}$ = $H_2NCH_2CONH$—) in 90% yield.

Nuclear magnetic resonance peaks (PPM; DMSO-$D_6$ and $D_2O$): 1.45(d,6H), 3.75(b,5H), 4.2(b,2H), 5.4(m,2H), 5.7(s,1H), and 7.3(b, 5H).

EXAMPLE 42

The procedure of Example 39 is employed, starting with appropriate chemical reagents, to produce the following penicillin analogs:

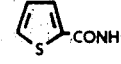

| Ar | A | $R_{10}$ |
|---|---|---|
| $C_6H_5$— | —$CH_2$— | n-$C_3H_7S$— |
| $C_6H_5$— | —$CH_2$— | i-$C_3H_7O$— |
| $C_6H_5$— | —$CH_2$— | m-$ClC_6H_4S$— |
| $C_6H_5$— | —$CH_2$— | n-$C_3H_7SO_2$— |
| $C_6H_5$— | —$CH_2$— | n-$C_3H_7NH$— |
| $C_6H_5$— | $CH_3CH$— | $C_2H_5S$— |
| $C_6H_5$— | $CH_3CH$— | $C_2H_5NH$— |
| $C_6H_5$— | $CH_3CH$— | $CH_3CH_2CONH$— |
| $C_6H_5$— | $CH_3CH$— | 3,5-$Cl_2C_6H_3O$— |
| $C_6H_5$— | $CH_3CH_2CH$— | 3,5-$Cl_2C_6H_3O$— |
| 4-$HOC_6H_4$— | —$CH_2$— | $CH_3S$— |
| 4-$HOC_6H_4$— | —$CH_2$— | $CH_3O$— |
| 4-$HOC_6H_4$— | —$CH_2$— | m-$BrC_6H_4S$— |
| 4-$HOC_6H_4$— | —$CH_2$— | m-$ClC_6H_4O$— |
| 4-$HOC_6H_4$— | —$CH_2$— | o-$CH_3C_6H_4S$— |
| 4-$HOC_6H_4$— | $CH_3CH$— | $C_2H_5S$— |
| 4-$HOC_6H_4$— | $CH_3CH$— | m-$CH_3OC_6H_4S$— |
| 4-$HOC_6H_4$— | $CH_3CH$— | m-$ClC_6H_4O$— |
| 4-$HOC_6H_4$— | $CH_3CH_2CH$— | $CH_3(CH_2)_2CONH$— |
| 4-$HOC_6H_4$— | $CH_3CH_2CH$— | m-$ClC_6H_4CONH$— |
| 2-$C_4H_3S$— | —$CH_2$— | $CH_3S$— |
| 2-$C_4H_3S$— | —$CH_2$— | i-$C_3H_7O$— |
| 2-$C_4H_3S$— | —$CH_2$— | $CH_3SO$— |
| 2-$C_4H_3S$— | —$CH_2$— | p-$ClC_6H_4S$— |
| 2-$C_4H_3S$— | $CH_3CH$— | o-$FC_6H_4S$— |
| 2-$C_4H_3S$— | $CH_3CH$— | p-$ClC_6H_4O$— |
| 2-$C_4H_3S$— | $CH_3CH$— | $C_6H_5SO_2NH$— |
| 2-$C_4H_3S$— | $CH_3CH_2CH$— | $CH_3O$— |
| 2-$C_4H_3S$— | $CH_3CH_2CH$— | m-$ClC_6H_4CONH$— |
| 2-$C_4H_3S$— | $CH_3CH_2CH$— | 3,5-$Cl_2C_6H_3CONH$— |
| 3-$C_4H_3S$— | —$CH_2$— | $CH_3S$— |
| 3-$C_4H_3S$— | —$CH_2$— | $CH_3O$— |
| 3-$C_4H_3S$— | —$CH_2$— | 3,5-$Cl_2C_6H_3S$— |
| 3-$C_4H_3S$— | —$CH_2$— | 3,5-$Cl_2C_6H_3O$— |
| 3-$C_4H_3S$— | —$CH_2$— | n-$C_3H_7NH$— |
| 3-$C_4H_3S$— | $CH_3CH$— | $CH_3O$— |
| 3-$C_4H_3S$— | $CH_3CH$— | $CH_3CONH$— |
| 3-$C_4H_3S$— | $CH_3CH$— | $C_6H_5SO_2NH$— |
| 3-$C_4H_3S$— | $CH_3CH_2CH$— | m-$ClC_6H_4CONH$— |
| 3-$C_4H_3S$— | $CH_3CH_2CH$— | 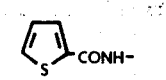CONH- |

EXAMPLE 43

6-[D-2-Phenyl-2-(2-hydroxy-2-phenylacetimidoylaminoacetamido)acetamido]- penicillanic acid (Ar = $C_6H_5$; A = —$CH_2$—; $R_{11}$ = H; $R_{12}$ = $C_6H_5$).

A mixture of 1.08 g. (5 m moles) of ethyl 2-hydroxy-2-phenyl acetimidate hydrochloride, 2.03 g. (5 m moles) of 6-[D-2-phenyl-2-(aminoacetamido)- acetamido]penicillanic acid and 1.4 ml. (10 m moles) of triethylamine in 25 ml. of dimethylformamide is allowed to stir at room temperature for 5 hrs. The mixture is filtered, and the filtrate poured into 300 ml. of dietyl ether. The precipitate is washed successively with diethyl ether, acetone and methylene chloride, and dried in vacuo to give 2.3 g. of the desired product.

Nuclear magnetic resonance spectrum peaks (PPM; DMSO-$D_6$ and $D_2O$): 1.45(d,6H), 3.9(s,1H), 4.2(b,2H), 5.2-6.0(m,4H), and 6.95-7.8(b,10H).

EXAMPLE 44

6-[D-2-Phenyl-2-(2-hydroxy-i-butyroimidoylaminoacetamido)acetamido]penicillanic acid (Ar = $C_6H_5$; A = —$CH_2$—; $R_{11}$ = $CH_3$; $R_{12}$ = $CH_3$)

In a manner similar to Example 43, the requisite starting materials provided the desired product in 80% yield.

Nuclear magnetic resonance spectrum peaks (PPM; DMSO-$D_6$ and $D_2O$): 1.45(b,12H), 3.95(s,1H), 4.2(b,2H), 5.35(m,2H), 5.75(s,1H), and 7.35(b,5H).

EXAMPLE 45

The procedure of Example 43 is again repeated, starting with the appropriate chemical reagents, to provide the following compounds:

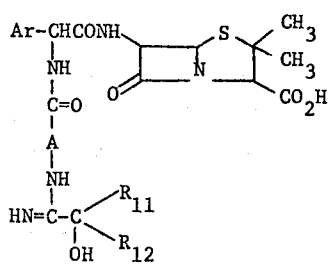

| Ar | A | $R_{11}$ | $R_{12}$ |
|---|---|---|---|
| $C_6H_5$— | —$CH_2$— | H— | $C_2H_5$— |
| $C_6H_5$— | —$CH_2$— | $C_2H_5$— | $C_6H_5$— |
| $C_6H_5$— | —$CH_2$— | H— | i-$C_3H_7$— |
| $C_6H_5$— | —$CH_2$— | n-$C_3H_7$— | $C_6H_5$— |
| $C_6H_5$— | $CH_3CH$— | $C_2H_5$— | $C_6H_5$— |
| $C_6H_5$— | $CH_3CH$— | H— | i-$C_3H_7$— |
| $C_6H_5$— | $CH_3CH$— | H— | $C_2H_5$— |
| $C_6H_5$— | $CH_3CH$— | $C_2H_5$— | $C_2H_5$— |
| $C_6H_5$— | $CH_3CH_2CH$— | H— | $C_2H_5$— |
| 4-HOC$_6H_4$— | —$CH_2$— | H— | $CH_3$— |
| 4-HOC$_6H_4$— | —$CH_2$— | $CH_3$— | $C_2H_5$— |
| 4-HOC$_6H_4$— | —$CH_2$— | $CH_3$— | $CH_3$— |
| 4-HOC$_6H_4$— | —$CH_2$— | H— | $C_6H_5$— |
| 4-HOC$_6H_4$— | $CH_3CH$— | $CH_3$— | $C_6H_5$— |
| 4-HOC$_6H_4$— | $CH_3CH$— | $CH_3$— | $CH_3$— |
| 4-HOC$_6H_4$— | $CH_3CH_2CH$— | n-$C_3H_7$— | $C_6H_5$— |
| 4-HOC$_6H_4$— | $CH_3CH_2CH$— | H— | $C_6H_5$— |
| 4-HOC$_6H_4$— | $CH_3CH_2CH$— | $CH_3$— | $CH_3$— |
| 2-$C_4H_3S$— | —$CH_2$— | H— | $C_2H_5$— |
| 2-$C_4H_3S$— | —$CH_2$— | $C_2H_5$— | $C_2H_5$— |
| 2-$C_4H_3S$— | —$CH_2$— | n-$C_3H_7$— | $C_6H_5$— |
| 2-$C_4H_3S$— | —$CH_2$— | H— | $CH_3$— |
| 2-$C_4H_3S$— | $CH_3CH$— | H— | $CH_3$— |
| 2-$C_4H_3S$— | $CH_3CH_2CH$— | $CH_3$— | $CH_3$— |
| 2-$C_4H_3S$— | $CH_3CH_2CH$— | $C_2H_5$— | $C_6H_5$— |

-continued

| Ar | A | $R_{11}$ | $R_{12}$ |
|---|---|---|---|
| 2-$C_4H_3S$— | $CH_3CH_2CH$— | H— | i-$C_3H_7$— |
| 3-$C_4H_3S$— | —$CH_2$— | n-$C_3H_7$— | $C_6H_5$— |
| 3-$C_4H_3S$— | —$CH_2$— | H— | $C_6H_5$— |
| 3-$C_4H_3S$— | —$CH_2$— | $CH_3$— | $CH_3$— |
| 3-$C_4H_3S$— | —$CH_2$— | H— | i-$C_3H_7$— |
| 3-$C_4H_3S$— | $CH_3CH$— | H— | $C_6H_5$— |
| 3-$C_4H_3S$— | $CH_3CH$— | $CH_3$— | $CH_3$— |
| 3-$C_4H_3S$— | $CH_3CH$— | H— | i-$C_3H_7$— |
| 3-$C_4H_3S$— | $CH_3CH_2CH$— | $CH_3$— | $CH_3$— |
| 3-$C_4H_3S$— | $CH_3CH_2CH$— | H— | $C_6H_5$— |

EXAMPLE 46

6-[D-2-phenyl-2-(2-thenoimidoylaminoacetamido)acetamido]penicillanic acid sodium salt To a solution of 1.0 g. (19 m moles) of 6-[D-2-phenyl-2(2-thenoimidoylaminoacetamido)acetamido]-penicillanic acid in 7 ml. of dioxane and 40 ml. of water cooled to 10° C. is added 160 mg. (19 m moles) of sodium bicarbonate dissolved in 10 ml. of water. The solution is allowed to stir for 10 min., dialyzed for 30 min., and the filtrate freeze-dried. The resulting solid is slurried in 40 ml. of chloroform, filtered and dried in vacuo, 880 mg.

In a similar manner, starting with a suitable base, the corresponding potassium, calcium, magnesium and other pharmaceutically acceptable metal salts of 6-[D-2-phenyl-2-(2-thenoimidoylaminoacetamido)acetamido]penicillanic acid and the herein described penicillins are prepared.

EXAMPLE 47

6-[D-2-Phenyl-2-(3-amidinopropionamido)acetamido]penicillanic acid triethylamine salt A slurry of 1.7 g. (3.8 m moles) of 6-[D-2-phenyl-2-(3-amidinopropionamdo)acetamido]penicillanic acid in 20 ml. of water is treated with 0.5 ml. (3.8 m moles) of triethylamine. After stirring for 5 min., a small amount of insolubles are filtered, and the filtrate is freeze-dried.

In a similar manner, the ammonium salt and pharmaceutically acceptable salts derived from organic amines for the above-described penicillin and the other herein described penicillins are prepared.

EXAMPLE 48

A tablet base is prepared by blending the following ingredients in the proportion by weight indicated.

| | |
|---|---|
| Sucrose, U.S.P. | 80.0 |
| Tapioca starch | 12.5 |
| Magnesium stearate | 7.5 |

Sufficient 6-[D-2-phenyl-2-(3-amidinopropionamido)acetamido]penicillanic acid is blended into the base to provide tablets containing 25, 100 and 250 mg. of active ingredient.

EXAMPLE 49

A suspension of 6-[D-2-phenyl-2-(amidinoacetamido)acetamido]penicillannic acid, sodium salt is prepared with the following composition:

| | | |
|---|---|---|
| penicillin compound | 31.42 | g. |
| 70% aqueous sorbitol | 714.29 | g. |
| Glycerine, U.S.P. | 185.35 | g. |
| Gum acacia (10% solution) | 100.00 | ml. |
| Polyvinyl pyrrolidone | 0.50 | g. |
| Propyl parahydroxybenzoate | 0.072 | g. |
| Distilled water to make one liter | 0.094 | g. |

Various sweetening and flavoring agents may be added to this suspension, as well as acceptable coloring. The suspension contains approximately 25 mg. of penicillin compound per milliliter.

EXAMPLE 50

Capsules containing 25, 100 and 250 mg. of active ingredient are prepared by blending sufficient 6-[D-2-phenyl-2-(p-chlorobenzimidoylaminoacetamido)acetamido]penicillanic acid in the following mixture (proportions given in parts by weight):

| | |
|---|---|
| Calcium carbonate, U.S.P. | 17.5 |
| Dicalcium phosphate | 18.9 |
| Magnesium trisilicate | 4.2 |
| Lactose, U.S.P. | 6.2 |
| Potato starch | 5.2 |
| Magnesium stearate | 1.0 |

EXAMPLE 51

A parenteral form of 6-[D-2-phenyl-2-(acetimidoylaminoacetamido)acetamido]penicillanic acid, sodium salt is prepared by dissolving an intimate mixture of the penicillin compound and sodium citrate (4% by weight) in sufficient polyethylene glycol 200 such that the final concentration of the penicillin compound is 25 mg. of active ingredient per milliliter. The resulting solution is sterilized by filtration and sterilely stoppered in vials.

In like manner, formulations of the products of this invention are made.

EXAMPLE 52

6-[D-2-Phenyl-2-(4-pyridoimidoylaminoacetamido)acetamido]penicillanic acid sodium salt To a solution of 520 mg. (6 m moles) of sodium bicarbonate in 100 ml. of water cooled to 10° C. is added over a 20 min. period 3.19 g. (6 m moles) of 6-[D-2-phenyl-2-(4-pyridoimidoylaminoacetamido)acetamido]penicillanic acid. The cooled solution is stirred for 10 min., filtered and the filtrate freeze dried. The desired product, 3.3 g., can be utilized, after reconstitution in water and sterilization by filtration, for parenteral administration.

EXAMPLE 53

6-[D-2-Phenyl-2-(4-pyridoimidoylaminoacetamido)acetamido]penicillanic acid hydrochloride To 1.53 g. (3 m moles) of 6-[D-2-phenyl-2-(4-pyridoimidoylaminoacetamido)acetamido]penicillanic acid in 25 ml. of water cooled in an ice bath is added 3 ml. of 1N hydrochloric acid (3 m moles) and the solution freeze dried. The product is triturated with acetone and filtered, 1.2 g.

EXAMPLE 54

6-[D-2-Phenyl-2-(4-pyridoimidoylaminoacetamido)acetamido]penicillanic acid citrate In a manner similar to Example 53, 1.53 g. (3 m moles) of 6-[D-2-phenyl-2-(4-pyridoimidoylaminoacetamido)acetamido]penicillanic acid in 25 ml. of water is treated with 576 mg. (3 m moles) of citric acid in one ml. of water of yield 1.7 g. of the desired product.

The penicillins of Examples 34 through 38 are converted to their pharmaceutically acceptable salts employing the procedures of Examples 53 and 54.

PREPARATION A

Amidinoalkanoic Acids 1. 3-Amidinopropionic Acid hydrochloride a. Methyl-β-carbomethoxypropionimidate hydrochloride Into a solution of 8.2 g. (0.256 mole) of anhydrous methanol and 29 g. (0.256 mole) of commercial methyl 3-cyanopropionate in 20 ml. of diethyl ether cooled to 0° C. is bubbled anhydrous hydrogen chloride gas. When the theoretical amount of gas has been taken up (~9.4 g.) the gas introduction is stopped and the closed reaction mixture placed in a cold box overnight. The resulting precipitate is filtered, washed with ether and dried in vacuo, 36.2 g. (78% yield), m.p. 80°–82° C.

b. β-Carbomethoxypropionamidine hydrochloride

To a suspension of 16.5 g. (0.09 mole) of methyl β-carbomethoxypropionimidate hydrochloride in 20 ml. of methanol at ice bath temperatures is added 12 ml. of the same solvent containing 1.7 g. of dissolved ammonia gas. The reaction mixture is allowed to stir at room temperature for 2 hrs., followed by filtration of some insoluble material and concentration of the filtrate to near dryness. The residual white solids are treated with ethanol, filtered and dried, 7.8 g. (51.5% yield), m.p. 132°–134° C.

c. 3-Amidinopropionic Acid hydrochloride

A solution of 7.8 g. (0.047 mole) of β-carbomethoxypropionamidine hydrochloride in 217 ml. of 12N hydrochloric acid is heated at steam bath temperatures for 1 hour. The solution is cooled, evaporated in vacuo to dryness, and the residual product triturated several times with ethylene dichloride and filtered, 7.1 g. (99% yield), m.p. 138°–140° C. (McElvain, et al., *J. Am. Chem. Soc.*, 71, 40 (1949) reports a melting point for crude product of 131°–137° C.).

2. Starting with the appropriate nitrile and amine or ammonia, and following the general procedure of Preparation A - 1a through 1c, the following amidinoalkanoic acid hydrochlorides are prepared as intermediates leading to the products of the present invention.

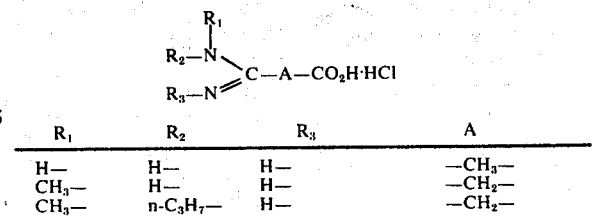

| $R_1$ | $R_2$ | $R_3$ | A |
|---|---|---|---|
| H— | H— | H— | —CH$_2$— |
| CH$_3$— | H— | H— | —CH$_2$— |
| CH$_3$— | n-C$_3$H$_7$— | H— | —CH$_2$— |

-continued

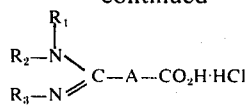

| R₁ | R₂ | R₃ | A |
|---|---|---|---|
| $C_2H_5-$ | H— | H— | $-(CH_2)_2-$ |
| n-$C_3H_7-$ | H— | H— | $-CH_2-$ |
| $CH_3-$ | H— | H— | $CH_3\overset{\mid}{C}H-$ |
| H— | H— | H— | $(CH_3)_2\overset{\mid}{C}-$ |
| $CH_3-$ | H— | H— | $(CH_3)_2\overset{\mid}{C}-$ |
| H— | H— | i-$C_3H_7-$ | $(CH_3)_2\overset{\mid}{C}-$ |
| H— | H— | $C_6H_5-$ | $-CH_2-$ |
| H— | $CH_3-$ | p-Br$C_6H_4-$ | $-(CH_2)_2-$ |
| H— | H— | p-$CH_3C_6H_4CH_2-$ | $-(CH_2)_2-$ |
| H— | H— | 2-$C_5H_4N-$ | $-(CH_2)_2-$ |
| H— | H— | m-$CH_3C_6H_4-$ | $-CH_2-$ |
| H— | H— | 4-$C_5H_4N-$ | $-CH_2-$ |
| $-(CH_2)_5-$ | | H— | $-CH_2-$ |
| $CH_3-$ | H— | H— | 1,4-$C_6H_4-$ |
| $CH_3-$ | $CH_3-$ | H— | 1,4-$C_6H_4-$ |
| i-$C_3H_7-$ | H— | H— | 1,4-$C_6H_4-$ |
| H— | n-$C_3H_7-$ | o-Cl$C_6H_4CH_2-$ | $-CH_2-$ |
| $C_2H_5-$ | H— | H— | 1,4-$C_6H_4-$ |

3. N,N′-Diethylamidinoacetic Acid Hydrochloride a. N-Ethyl-carboethoxyacetamide

To 15.0 g. (0.1 mole) of carboethoxyacetyl chloride in 150 ml. of benzene is added, with cooling, 9.9 g. (0.22 mole) of ethylamine in 50 ml. of the same solvent. The reaction mixture is allowed to stir at room temperature overnight, followed by filtration. The filtrate is washed with water, dried over sodium sulfate and concentrated to dryness. The residual product is washed several times with diisopropyl ether and dried in vacuo. The crude product is employed in the next reaction without further purification.

b. Methyl N-ethyl-carboethoxyaceimidate

To a refluxing, stirred solution of 9.54 g. (0.06 mole) of N-ethyl-carboethoxyacetamide in 20 ml. of benzene is added 5.69 ml. (0.06 mole) of dimethyl sulfate over a period of 2.5 hrs. and the resulting mixture is refluxed for 16 hrs. The cooled reaction mixture is neutralized carefully with 6N sodium hydroxide solution, and the organic phase separated and dried over sodium sulfate. Removal of the solvent under reduced pressure provides the crude product which is employed in the next reaction step without further purification.

c. N,N′-Diethyl-carboethoxyacetamidine Hydrochloride

To a solution of 3.46 g. (0.02 mole) of methyl N-ethyl-carbethoxyacetimidate in 30 ml. of diethyl ether is added 900 mg. (0.02 mole) of ethylamine and the reaction mixture allowed to stir several hours at room temperature. Anhydrous hydrogen chloride gas is slowly introduced into the reaction mixture until the formation of the amidine hydrochloride ceases. The product is filtered and dried in vacuo.

d. N,N′-Diethylamidinoacetic Acid Hydrochloride

A solution of 2.2 g. (0.01 mole) of N,N′-diethyl-carboethoxyacetamidine hydrochloride in 60 ml. of 12N hydrochloric acid is converted to the free acid in a manner similar to the procedure of Preparation A-1c.

4. Employing the procedure of Preparation A-2a through 2d, and starting with the appropriate reagents, the following intermediates employed in the synthesis of the subject compounds are prepared:

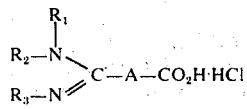

| R₁ | R₂ | R₃ | A |
|---|---|---|---|
| $CH_3-$ | $CH_3-$ | $CH_3-$ | $-(CH_2)_2-$ |
| H— | i-$C_3H_7-$ | i-$C_3H_7-$ | $-(CH_2)_2-$ |
| H— | $CH_3-$ | $CH_3-$ | $CH_3\overset{\mid}{C}H-$ |
| H— | $C_2H_5-$ | $C_2H_5-$ | $CH_3CH_2\overset{\mid}{C}H-$ |
| $CH_3-$ | $CH_3-$ | $CH_3-$ | $-CH_2-$ |
| $C_2H_5-$ | H— | m-$CF_3C_6H_4-$ | $CH_3CH_2\overset{\mid}{C}H-$ |
| $CH_3-$ | $CH_3-$ | p-F$C_6H_4-$ | $CH_3\overset{\mid}{C}H-$ |
| $CH_3-$ | $CH_3-$ | p-$CH_3OC_6H_4-$ | $-CH_2-$ |
| H— | $C_2H_5-$ | $C_2H_5-$ | 1,4-$C_6H_4-$ |
| $CH_3-$ | $CH_3-$ | $CH_3-$ | 1,4-$C_6H_4-$ |
| $-(CH_2)_3-$ | | $C_6H_5-$ | $-CH_2-$ |
| $-(CH_2)_5-$ | | m-F$C_6H_4CH_2-$ | $-CH_2-$ |
| $-(CH_2)_4-$ | | o-Br$C_6H_4-$ | $CH_3CH_2\overset{\mid}{C}H-$ |
| $-(CH_2)_4-$ | | α-$C_4H_3S-$ | $(CH_3)_2\overset{\mid}{C}-$ |
| $-(CH_2)_3-$ | | β-$C_4H_3O-$ | $-CH_2CH(CH_3)-$ |
| $-(CH_2)_5-$ | | m-$CH_3OC_6H_4-$ | $CH_3CH_2\overset{\mid}{C}H-$ |
| $-(CH_2)_6-$ | | 3-$C_5H_4N-$ | $-CH_2CH(CH_3)-$ |
| $-(CH_2)_4-$ | | β-$C_{10}H_7-$ | $-CH_2-$ |
| $-(CH_2)_5-$ | | p-Br$C_6H_4-$ | $-CH_2-$ |
| $-(CH_2)_6-$ | | p-$CF_3C_6H_4-$ | $-(CH_2)_2-$ |
| $-(CH_2)_5-$ | | 2-$C_5H_4N-$ | $-CH(CH_3)CH_2-$ |
| $-(CH_2)_4-$ | | α-$C_{10}H_7-$ | $-(CH_2)_2-$ |
| $-(CH_2)_4-$ | | n-$C_3H_7-$ | $-(CH_2)_2-$ |
| $-(CH_2)_5-$ | | $CH_3-$ | $-CH_2-$ |

5. 3-(2-Imidazolinyl)propionic Acid Hydrochloride

To a solution of 7.65 ml. (0.114 mole) of ethylenediamine in 120 ml. of anhydrous ethanol is added 21.8 g. (0.12 mole) of methyl β-carbomethoxypropionimidate hydrochloride and the resulting mixure heated to reflux overnight. The mixture is cooled, filtered and the filtrate concentrated to an oil.

Concentrated hydrochloric acid (600 ml.) is added to the residual product and the resulting solution heated at steam bath temperatures for 1.5 hrs. The solution is concentrated under reduced pressure to an oil, which on trituration with ethylenedichloride and then acetone provides the product as a white solid, 15.0 g.

6. Starting with the requisite imino ester, prepared by the herein described procedures, and the appropriate diamines, and employing the general experimental conditions of Preparation A-5, the following intermediates leading to the products of the instant invention are prepared:

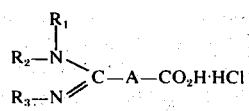

| R₁ | R₂ | R₃ | A |
|---|---|---|---|
| H— | $-(CH_2)_2-$ | | $-CH_2-$ |
| H— | $-(CH_2)_2-$ | | $CH_3\overset{\mid}{C}H-$ |
| H— | $-(CH_2)_3-$ | | $-CH_2-$ |
| $CH_3-$ | $-(CH_2)_2-$ | | $-CH_2-$ |
| n-$C_3H_7-$ | $-(CH_2)_3-$ | | $-CH(CH_3)CH_2-$ |
| H— | $-(CH_2)_4-$ | | $CH_3CH_2\overset{\mid}{C}H-$ |
| $C_2H_5-$ | $-(CH_2)_3-$ | | $-(CH_2)_2-$ |
| $CH_3-$ | $-(CH_2)_2-$ | | $(CH_3)_2\overset{\mid}{C}-$ |

-continued $$R_2-N\overset{R_1}{\underset{R_3-N}{\diagup}}C-A-CO_2H\cdot HCl$$

| $R_1$ | $R_2$ | $R_3$ | A |
|---|---|---|---|
| H— | | —(CH₂)₃— | —(CH₂)₂— |

PREPARATION B

Amidinoalkanoic Acid Chlorides 1. 3-Amidinopropionylchloride hydrochloride

A solution of 1.52 g. (0.01 mole) of 3-amidinopropionic acid hydrochloride in 18 ml. of thionyl chloride is allowed to stir at room temperature overnight. The excess solvent-reactant is then removed under reduced pressure and the product is isolated as a yellow gum, which crystallizes on standing, 1.5 g.

2. Following the above procedure and starting with the appropriate acid hydrochloride and thionyl chloride, the acid chlorides employed for the acylation of the α-aminoarylmethylpenicillins are conveniently prepared.

PREPARATION C

Imidoylaminoalkanoic Acids

1. Isobutyrimidoylaminoacetic acid hydrochloride a. Ethyl isobutyrimidate hydrochloride Hydrogen chloride gas is slowly bubbled into a solution of 34.5 g. (0.5 mole) of isobutyronitrile in 25.3 g. of absolute ethanol maintained at 0° C. in an ice-water bath. After 1.5 hrs. the addition tube is removed and the mixture allowed to remain at room temperature several days. The solvent is removed under reduced pressure and the residual clear oil treated with 400 ml. of diethyl ether. The resulting precipitate, after stirring overnight, is filtered, washed with ether and dried in vacuo, 51.8 g. (68% yield), m.p. 100°–101.5° C.

b. Isobutyrimidoylaminoacetic acid hydrochloride

To 250 ml. of a 33% potassium carbonate solution in water is added 51.0 g. (0.33 mole) of ethyl isobutyrimidate hydrochloride, and the free base extracted with 300 ml. of diethyl ether. The ether extract is dried over sodium sulfate, concentrated to an oil, and the residual base, 27.7 g., combined with 9.0 g. of glycine and 24 ml. of amyl alcohol. After heating to reflux for 2 hrs., the mixture is cooled and the precipitated product is filtered, washed with ether and dried, 16.4 g., m.p. 208°–210° C. (dec).

Eight grams (0.055 mole) of free base in 200 ml. of ether is treated with gaseous hydrogen chloride. After stirring for 30 min. the product is filtered and dried, 9.9 g., m.p. 153°–170° C. (dec).

2. The following acid hydrochlorides are synthesized as intermediates leading to the products of the present invention by repeating the above procedure of Preparation B-1a through 1b, starting with the requisite chemical reagents:

$$R_4-\overset{R_2-N}{\overset{\|}{C}}-N(R_1)-A-CO_2H\cdot HCl$$

| $R_1$ | $R_2$ | $R_4$ | A |
|---|---|---|---|
| *H— | H— | H— | —CH₂— |
| H— | H— | CH₃— | —CH₂— |

-continued $$R_4-\overset{R_2-N}{\overset{\|}{C}}-N(R_1)-A-CO_2H\cdot HCl$$

| $R_1$ | $R_2$ | $R_4$ | A |
|---|---|---|---|
| H— | H— | C₂H₅— | —CH₂— |
| H— | H— | n-C₃H₇— | —CH₂— |
| *CH₃— | H— | H— | —CH₂— |
| *i-C₃H₇— | H— | H— | —(CH₂)₂— |
| n-C₃H₇— | H— | i-C₃H₇— | CH₃CH₂CH— |
| H— | H— | CH₃— | —CH(CH₃)CH₂— |
| CH₃— | H— | C₂H₅— | —(CH₂)₂— |
| *H— | H— | H— | —CH₂CH(CH₃)— |
| *i-C₃H₇— | H— | H— | —CH₂— |
| H— | H— | p-ClC₆H₄CH₂— | —CH₂— |
| H— | H— | C₆H₅— | —CH₂— |
| H— | H— | p-CH₃OC₆H₄— | —CH₂— |
| H— | H— | p-CF₃C₆H₄— | —CH₂— |
| H— | H— | p-ClC₆H₄— | —CH₂— |
| H— | H— | 2-C₄H₃S— | —CH₂— |
| H— | H— | p-FC₆H₄— | —CH₂— |
| H— | H— | p-BrC₆H₄— | —CH₂— |
| H— | H— | p-CH₃C₆H₄— | —CH₂— |
| H— | H— | m-ClC₆H₄— | —CH₂— |
| H— | H— | 2-C₄H₃O— | —CH₂— |
| H— | H— | 3,4-Cl₂C₆H₃— | —CH₂— |
| CH₃— | H— | o-ClC₆H₄— | —CH₂— |
| H— | H— | m-CH₃OC₆H₄CH₂— | —CH₂— |
| H— | H— | o-CF₃C₆H₄— | s,33 CH₃CH— |
| H— | H— | m-CH₃OC₆H₄— | —CH₂— |
| H— | H— | o-ClC₆H₄— | CH₃CH₂CH— |

*For the synthesis of those intermediates wherein $R_2$ and $R_4$ are each H, the preferred preparation employs the condensation of formamidine with the requisite amino acid according to the procedure of Uyeda, et al., J. Biol. Chem., 240, 1701 (1965).

3. N-(N'-Methylacetimidoyl)aminoacetic Acid Hydrochloride a. Ethyl N-methylacetimidate To a solution of triethyloxonium fluoborate, prepared from 91 g. (0.64 mole) of boron trifluoride etherate and 44.4 g. (0.48 mole) of epichlorohydrin in 300 ml. of ether, employing the procedure of Meerwein, et al., J. prakt., 154, 83 (1940), dissolved in 75 ml. of methylene chloride and cooled to 10°–15° C. is added dropwise 23.6 g. (0.04 mole) of N-methylacetamide dissolved in 200 ml. of the same solvent. The resulting solution is stirred at room temperature and allowed to stand overnight. To the stirred solution is slowly added 76 g. of a 50% potassium carbonate solution. The mixture is filtered and the filtrate dried over sodium sulfate and concentrated under reduced pressure to an oil. The residual product is employed in the next reaction without further purification.

b. N-(N'-Methylacetimidoyl)aminoacetic Hydrochloride

A solution of 10.1 (0.12 mole) of ethyl N-methylacetimidate and 4.5 g. (0.06 mole) of glycine in 36 ml. of amyl alcohol is heated to reflux for 1.5 hrs. The precipitated product, which forms on cooling the reaction mixture, is filtered, washed several times with diethyl ether and dried in vacuo.

The product, suspended in 250 ml. of diethyl ether, is treated with gaseous hydrogen chloride until it is converted to the hydrochloride salt, which is then filtered and dried.

4. Starting with the appropriately substituted amine and amino acid, and repeating the procedure of Preparation C-3a through 3b, the following intermediates employed in the preparation of the final products are synthesized:

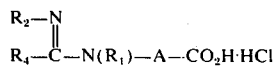

| $R_1$ | $R_2$ | $R_4$ | A |
|---|---|---|---|
| $C_2H_5-$ | $CH_3-$ | $CH_3-$ | $-CH_2-$ |
| $H-$ | $n-C_3H_7-$ | $n-C_3H_7-$ | $-(CH_2)_2-$ |
| $H-$ | $C_2H_5-$ | $C_2H_5-$ | $CH_3CH-$ |
| $H-$ | $i-C_3H_7-$ | $CH_3-$ | $-(CH_2)_2-$ |
| $H-$ | $C_2H_5-$ | $m-FC_6H_4-$ | $-CH_2-$ |
| $H-$ | $CH_3-$ | $p-CF_3C_6H_4-$ | $-CH_2-$ |
| $H-$ | $C_2H_5-$ | $m-FC_6H_4-$ | $-CH_2-$ |
| $H-$ | $CH_3-$ | $3,5-Cl_2C_6H_3-$ | $-CH_2-$ |
| $H-$ | $H-$ | $3,5-Cl_2C_6H_3-$ | $-CH_2-$ |
| $H-$ | $H-$ | $3,4-Cl_2C_6H_3-$ | $-CH_2-$ |

5. 2-N-n-Propyl-N-carboxymethyl)amino-1-azacyclohept-2-ene Hydrochloride

A solution of 14.1 g. (0.1 mole) of O-ethylcaprolactim, Benson, et al., *J. Am. Chem. Soc.*, 70, 2115 (1948), and 5.85 g. (0.05 mole) of N-n-propylglycine, Greco, et al., *J. Med. Chem.*, 5, 861 (1962), in 40 ml. of amyl alcohol is heated to reflux for 2 hrs. The reaction mixture is then cooled, and the precipitated product is filtered, washed several times with diethyl ether, and dried.

A suspension of the product in 175 ml. of diethyl ether is treated with gaseous hydrogen chloride for 1.5 hrs. The solid, after stirring at room temperature for 3 hrs., is filtered and dried in vacuo. The product is used in subsequent reactions without further purification.

6. Employing the above procedure, Preparation C-5, and starting with the requisite lactim and amino acid, the following intermediates are prepared:

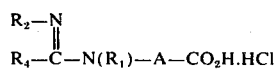

| $R_1$ | $R_2$ | $R_4$ | A |
|---|---|---|---|
| $H-$ | $-(CH_2)_3-$ | | $-CH_2-$ |
| $CH_3-$ | $-(CH_2)_3-$ | | $-CH_2-$ |
| $H-$ | $-(CH_2)_3-$ | | $-(CH_2)_2-$ |
| $H-$ | $-(CH_2)_3-$ | | $CH_3CH-$ |
| $CH_3-$ | $-(CH_2)_3-$ | | $(CH_3)_2C-$ |
| $H-$ | $-(CH_2)_3-$ | | $-CH(CH_3)CH_2-$ |
| $C_2H_5-$ | $-(CH_2)_3-$ | | $-CH_2-$ |

7. N-Carboxymethylimidazoline Hydrochloride a. N-Carbobenzyloxymethylimidazoline To a solution of 14.0 g. (0.2 mole) of imidazoline in 150 ml. of dry dimethylformamide is added dropwise with cooling 22.9 g. (0.1 mole) of benzyl bromoacetate. When the addition is complete, the reaction is warmed to 50°–60° C. for several hours, and is then cooled and diluted with water (250 ml.). The product is extracted with diethyl ether, and the extracts are combined and washed several times with a saturated brine solution. The ether phase is dried over sodium sulfate and concentrated to an oil, which is used in the next reaction without purification.

b. N-Carboxymethylimidazoline Hydrochloride

A suspension of 10.9 g. (0.05 mole) of N-carbobenzyloxymethylimidazoline and 50 mg. of 5% palladium-on-charcoal in 100 ml. of ethanol is shaken in an atmosphere of hydrogen at atmospheric pressure. When the theoretical amount of hydrogen has been absorbed, the spent catalyst is filtered and the filtrate treated with one equivalent of hydrogen chloride dissolved in ethyl acetate. The resulting solution is then concentrated to dryness in vacuo and the residual product triturated with ether and filtered.

8. Employing the alkylation and hydrogenation procedures of Preparation C-7a through 7b and starting with the appropriate chemical reagents, the following intermediates leading to the products of the instant invention are synthesized:

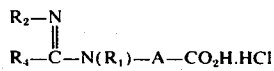

| $R_1$ | $R_2$ | $R_4$ | A |
|---|---|---|---|
| $-(CH_2)_3-$ | | $CH_3-$ | $-CH_2-$ |
| $-(CH_2)_3-$ | | $H-$ | $-(CH_2)_3-$ |
| $-(CH_2)_5-$ | | $CH_3-$ | $1,4-C_6H_4-$ |

PREPARATION D

Imidoylaminoalkanoic Acid Chlorides

1. Formimidoylaminoacetyl Chloride Hydrochloride

A suspension of 1.05 g. (7.6 m moles) of formimidoylaminoacetic acid hydrochloride in 30 ml. of dry methylene chloride is treated with 1.57 g. (7.6 m moles) of phosphorous pentachloride, and the mixture allowed to stir at room temperature overnight. The product is collected by suction filtration and dried in vacuo, 1.09 g. (91% yield).

2. Benzimidoylaminoacetyl Chloride Hydrochloride

To benzimidoylaminoacetic acid hydrochloride (2.2 g., 10 m moles) in 40 ml. of dry methylene chloride is added 2.5 g. (12 m moles) of phosphorous pentachloride, and the reaction mixture allowed to stir overnight at room temperature. The product is filtered, washed successively with methylene chloride (50 ml.), chloroform 2 × 75 ml.) and hexane (50 ml.) and dried in vacuo, 2.5 g. (99% yield).

3. Following the above procedures and starting with the appropriate acid hydrochloride, the imidoylaminoalkanoic acid chloride hydrochlorides employed in the acylation of the α-aminoarylmethylpenicillins are conveniently prepared.

PREPARATION E 1,3-Diazacycloalk-2-enes

1. The 1,3-diazacycloalk-2-enes utilized as starting reagents in Preparation C-8 are prepared by methods known to those skilled in the art; in particular, the procedures of Faust, et al., *J. Am. Chem. Soc.*, 81, 2214 (1959), Baganz, et al., *Ber.*, 95, 1840 (1962) and Oxley, et al., *J. Chem. Soc.*, 497 (1947) and 859 (1950) were employed.

PREPARATION F

Amino Acids

1. The amino acids employed as intermediates leading to the present invention are either commercial reagents or are synthesized by commonly known methods, for example, according to the synthetic routes as taught by Greenstein, et al., "Chemistry of the Amino Acids," John Wiley & Sons, Inc., New York, N.Y., 1961 (Vols. 1, 2 and 3).

PREPARATION G

Haloesters

1. The halo esters employed as intermediates are either commercial chemicals or are easily synthesized by one or more of the preparative procedures taught by Wagner, et al., "Synthetic Organic Chemistry," John Wiley & Sons, Inc., New York, N.Y., 1953, Chapter 14.

PREPARATION H

6-[2-Aryl-2-(aminoalkanoylamino)acetamido]penicillanic Acid 1. 6-[D-2-Phenyl-2-(aminoacetamido)acetamido]-penicillanic Acid a. 6-[D-2-Phenyl-2-(benzyloxycarbonylaminoacetamido)acetamido]penicillanic Acid To a cooled (0° C.) solution of 41.8 g. (0.2 mole) of N-benzyloxycarbonylglycine and 23.0 g. (0.2 mole) of N-hydroxysuccinimide in 800 ml. of methylene chloride is added in one portion 41.2 g. (0.2 mole) of dicyclohexylcarbodiimide, and the resulting reaction mixture allowed to stir in the cold for 10 min. and at room temperature for one hour. The filtered solids are washed (2 × 25 ml.) with methylene chloride, and the combined washings and filtrate are added to 80 g. (0.18 mole) of D-α-aminobenzylpenicillin triethylamine salt in 600 ml. of methylene chloride at 5° C. over a 10 min. period. After stirring in the cold for 1 hour the solution is concentrated in vacuo to dryness and the residue partitioned between 1 l. of water and 600 ml. of ethyl acetate. The pH is adjusted to 8.5, the aqueous layer separated and washed with ethyl acetate (2 × 200 ml.), and the aqueous then added to 800 ml. of ethyl acetate. The pH is adjusted to 2.6, the organic phase separated and washed successively with water (500 ml.) of pH 2.8, water and finally a saturated sodium chloride solution (300 ml.). The ethyl acetate is dried over sodium sulfate and concentrated under reduced pressure to give 96 g. of the desired intermediate.

b. 6-[D-2-phenyl-2-(aminoacetamido)acetamido]-penicillanic Acid

To a mixture of 3.1 g. (0.037 mole) of sodium bicarbonate in 50 ml. of water and 75 ml. of ethyl acetate is added 20.0 g. (0.037 mole) of 6-[D-2-phenyl-2-(benzyloxycarbonylaminoacetamido)acetamido]penicillanic acid and the pH adjusted to 7.4 with a saturated aqueous sodium bicarbonate solution. To the separated aqueous layer is added 15 g. of 10% palladium-on-charcoal, and the mixture shaken in a hydrogen atmosphere at an initial pressure of 50 p.s.i. When the reaction is complete, the spent catalyst is filtered and the pH of the filtrate is adjusted to pH 4.5. The aqueous is filtered and freeze dried to give 15 g. of the crude intermediate, which is employed in subsequent reactions without further purification.

2. Employing the procedure of Preparation H-1a through 1b, the following penicillanic acid congeners, used as intermediates in the preparation of the compounds of the present invention, are synthesized:

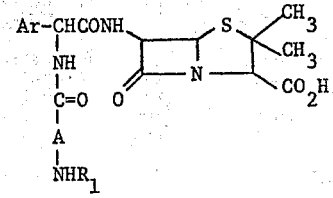

| Ar | A | R₁ |
| --- | --- | --- |
| C₆H₅— | —CH₂— | CH₃— |
| C₆H₅— | —CH₂— | C₂H₅— |
| C₆H₅— | —CH₂— | i-C₃H₇— |
| C₆H₅— | —CH₂— | n-C₃H₇— |
| C₆H₅— | CH₃CH— | H— |
| C₆H₅— | CH₃CH— | CH₃— |
| C₆H₅— | CH₃CH₂CH— | H— |
| C₆H₅— | CH₃CH₂CH— | CH₃— |
| 4-HOC₆H₅— | —CH₂— | H— |
| 4-HOC₆H₅— | —CH₂— | CH₃— |
| 4-HOC₆H₅— | —CH₂— | C₂H₅— |
| 4-HOC₆H₅— | CH₃CH— | H— |
| 4-HOC₆H₅— | CH₃CH— | CH₃— |
| 4-HOC₆H₅— | CH₃CH₂CH— | H— |
| 4-HOC₆H₅— | CH₃CH₂CH— | CH₃— |
| 2-C₄H₃S— | —CH₂— | H— |
| 2-C₄H₃S— | —CH₂— | CH₃— |
| 2-C₄H₃S— | —CH₂— | C₂H₅— |
| 2-C₄H₃S— | CH₃CH— | H— |
| 2-C₄H₃S— | CH₃CH— | CH₃— |
| 3-C₄H₃S— | —CH₂— | H— |
| 3-C₄H₃S— | —CH₂— | CH₃— |
| 3-C₄H₃S— | —CH₂— | C₂H₅— |
| 3-C₄H₃S— | CH₃CH— | H— |
| 3-C₄H₃S— | CH₃CH— | CH₃— |
| 3-C₄H₃S— | CH₃CH₂CH— | H— |

Synthesis of these intermediates is also taught in U.S. Pat. No. 3,340,252.

PREPARATION I

Iminoethers

The iminoethers and thioethers employed as intermediates in the present invention are synthesized by methods well known to those skilled in the art and reviewed by Rogers, et al., Chem. Rev., 61, 179 (1961) and taught by Paquette, J. Am. Chem. Soc., 86, 4096 (1964).

1. Ethyl 3,4-dichlorobenzimidate 3,4-Dichlorobenzamide (139 g.; 0.73 mole) suspended in 600 ml. of methylene chloride is added to 150 g. (0.8 mole) of triethyloxonium fluoroborate in 100 ml. of methylene chloride cooled in an ice-bath to 0° C. over a period of 10–15 min. At the end of the addition, the mixture is allowed to stir at room temperature overnight. The mixture is again cooled in an ice-bath and 141 g. of 50% potassium carbonate in water is added over 30 min. The mixture is stirred for 15 min., the methylene chloride layer separated and the solids washed with methylene chloride. The combined organic layer and washings are dried over sodium sulfate and concentrated in vacuo to a yellow oil which is treated with hexane. A small amount of solids are filtered and the filtrate concentrated to give, after drying in vacuo, 140 g. of the desired imino ether, m.p. 62°–64° C.

2. Methyl 2-pyridylimidate

To a solution of 26 g. (0.25 mole) of 2-cyanopyridine in 225 ml. of absolute methanol is added 1.35 g. of sodium methoxide, and the resulting solution allowed to stir at room temperature overnight. The reaction mixture is treated with 1.5 ml. of acetic acid and, after stirring 30 min., concentrated to a yellow oil. The product is extracted with 500 ml. of hexane, which is concentrated to give 30.4 g. of the desired intermediate product.

3. Ethyl 2,2-dimethyl-2-hydroxyacetimidate hydrochloride

Four grams of 2-methyllactonitrile is added to 100 ml. of diethyl ether containing 10 ml. of ethanol followed by saturation of the resulting solution with hydrogen chloride gas. The reaction mixture is allowed to stir at room temperature for 18 hrs. and subsequently concentrated to an oil which on slurrying in ether gave 7.2 g. of the desired product.

4. 4-Imidazolylthioformimidate dihydrochloride

To 900 mg. of 4-cyanoimidazole in 30 ml. of ethyl mercaptan cooled to 0° C. in a glass pressure bottle is added over 15 min. sufficient hydrogen chloride gas to saturate the solution. The sealed bottle is allowed to remain at room temperature for 20 min., and its contents then treated with 100 ml. of diethyl ether and filtered to give 1.7 g. of the product, m.p. 155°–158° C., dec.

4a. Methyl p-acetamidobenzthioimidate hydroiodide

To a mixture of 2.7 g. (0.014 mole) of p-acetamidobenzthioamide in 100 ml. of acetone is added 2.6 ml. of methyl iodide, and the resulting reaction mixture allowed to stir at room temperature overnight. The intermediate product is filtered and dried, 4.4 g., m.p. 216°–217° C.

5. Employing one of the indicated above procedures, the following iminoethers or thioethers are prepared as intermediates leading to the products of the present invention.

$$Q-\underset{\underset{R_2}{\overset{W-P}{|}}}{C}=N-R_2$$

| Q | $R_2$ | W | P | Preparation I |
|---|---|---|---|---|
| 3,4-$Cl_2C_6H_3$— | $CH_3$— | O | $C_2H_5$— | 1 |
| P-$\phi C_6H_4$— | H— | O | $C_2H_5$— | 3 |
| o-$ClC_6H_4$— | H— | O | $C_2H_5$— | 3 |
| p-$IC_6H_4$— | H— | O | $C_2H_5$— | 1 |
| 3,5-$Cl_2C_6H_3$— | H— | O | $C_2H_5$— | 1 |
| m-$NCC_6H_4$— | H— | O | $C_2H_5$— | 1 |
| p-$NCC_6H_4$— | H— | O | $C_2H_5$— | 1 |
| 3,5-$F_2C_6H_3$— | H— | O | $C_2H_5$— | 1 |
| 3-CN—5-$ClC_6H_3$— | H— | O | $C_2H_5$— | 1 |
| 3-CN—5-$BrC_6H_3$— | H— | O | $C_2H_5$— | 1 |
| 3,4-$Br_2C_6H_3$— | H— | O | $C_2H_5$— | 1 |
| 3,5-$Br_2C_6H_3$— | H— | O | $C_2H_5$— | 1 |
| 3,5-$I_2C_6H_3$— | H— | O | $C_2H_5$— | 1 |
| 3,4,5-$Cl_3C_6H_2$— | H— | O | $C_2H_5$— | 1 |
| 3,4,5-$Br_3C_6H_2$— | H— | O | $C_2H_5$— | 1 |
| 3,5-$Cl_2$—4-$BrC_6H_2$— | H— | O | $C_2H_5$— | 1 |
| 3,4-$Br_2$—4-$FC_6H_2$— | H— | O | $C_2H_5$— | 1 |
| 3,5-$Br_2$—4-$ClC_6H_2$— | H— | O | $C_2H_5$— | 1 |
| 3,5-$Br_2$—4-($C_2H_5$)—HN$C_6H_2$— | H— | O | $C_2H_5$— | 1 |
| m-$CF_3C_6H_4$— | H— | O | $C_2H_5$— | 1 |
| p-$CF_3C_6H_4$— | H— | O | $C_2H_5$— | 3 |
| 3,5-$(CF_3)_2C_6H_3$— | H— | O | $C_2H_5$— | 1 |
| 3,5-$(NC)_2C_6H_3$— | H— | O | $C_2H_5$— | 1 |
| p-$CF_3SC_6H_4$— | H— | O | $C_2H_5$— | 3 |
| p-$H_2NCOC_6H_4$— | H— | O | $C_2H_5$— | 3 |
| p-$H_2NCONHC_6H_4$— | H— | O | $C_2H_5$— | 3 |
| p-$CH_3CONHC_6H_4$— | H— | S | $CH_3$— | 4a |
| p-$CH_3COC_6H_4$— | H— | O | $C_2H_5$— | 3 |
| p-$H_2N-\underset{\underset{NH}{\overset{\parallel}{C}}}{}-C_6H_4$— | H— | O | $C_2H_5$— | 3 |
| p-$HOC_6H_4$— | H— | S | $C_2H_5$— | 4 |
| m-$HOC_6H_4$— | H— | S | $C_2H_5$— | 4 |
| m-$O_2NC_6H_4$— | H— | O | $C_2H_5$— | 3 |
| p-$O_2NC_6H_4$— | H— | O | $C_2H_5$— | 3 |
| p-$H_2NSO_2C_6H_4$— | H— | O | $C_2H_5$— | 3 |
| $C_6H_5CH_2$— | H— | S | $C_2H_5$— | 4 |

-continued $$Q-\underset{\underset{R_2}{\overset{W-P}{|}}}{C}=N-R_2$$

| Q | $R_2$ | W | P | Preparation I |
|---|---|---|---|---|
| 2,6-$Cl_2C_6H_3CH_2$— | H— | S | $C_2H_5$— | 4 |
| m-$ClC_6H_4CH_2$— | H— | S | $C_2H_5$— | 4 |
| p-$CH_3OC_6H_4CH_2$— | H— | S | $C_2H_5$— | 4 |
| p-$HOC_6H_4CH_2$— | H— | S | $C_2H_5$— | 4 |
| p-$FC_6H_4CH_2$— | H— | S | $C_2H_5$— | 4 |
| p-$C_2H_5O_2CC_6H_4$— | H— | O | $C_2H_5$— | 3 |
| 3,5-$(C_2H_5O_2C)_2C_6H_3$— | H— | O | $C_2H_5$— | 3 |
| m-$C_2H_5O_2CC_6H_4$— | H— | O | $C_2H_5$— | 3 |
| 3,5-$(i-C_4H_9O)_2C_6H_3$— | H— | O | $C_2H_5$— | 1 |
| 3,4-$(i-C_4H_9O)_2C_6H_3$— | H— | O | $C_2H_5$— | 1 |
| 3,5-$(i-C_3H_7O)_2C_6H_3$— | H— | O | $C_2H_5$— | 1 |
| 3,4-$(CH_2=CHCH_2O)_2C_6H_3$— | H— | O | $C_2H_5$— | 1 |
| 3,5-$(i-C_3H_7O)_2C_6H_3$— | H— | O | $C_2H_5$— | 1 |
| 3,4-$(CH_3CO_2)_2C_6H_3$— | H— | O | $C_2H_5$— | 1 |
| 3-$CH_3S$—4-$CH_3OC_6H_3$— | H— | O | $C_2H_5$— | 1 |
| p-$CH_3SC_6H_4$— | H— | O | $C_2H_5$— | 1 |
| 3,5-$(CH_3S)_2C_6H_3$— | H— | O | $C_2H_5$— | 1 |
| m-$CH_3SC_6H_4$— | H— | O | $C_2H_5$— | 1 |
| m-$(i-C_3H_7S)C_6H_4$— | H— | O | $C_2H_5$— | 1 |
| 3,4,5-$(CH_3O)_3C_6H_2$— | H— | O | $C_2H_5$— | 1 |
| m-$CH_3SO_2C_6H_4$— | H— | O | $C_2H_5$— | 1 |
| p-$CH_3SO_2C_6H_4$— | H— | O | $C_2H_5$— | 1 |
| 3-$CH_3SO_2$—4-$CH_3OC_6H_3$— | H— | O | $C_2H_5$— | 1 |
| 3,5-$(CH_3SO_2)_2C_6H_3$— | H— | O | $C_2H_5$— | 1 |
| p-$(CH_3)_3CCONHC_6H_4$— | H— | O | $C_2H_5$— | 3 |
| p-$(CH_3)_2NC_6H_4$— | H— | O | $C_2H_5$— | 3 |
| 2-$C_{10}H_7$— | H— | O | $C_2H_5$— | 1 |
| m-$H_2NSO_2C_6H_4$— | H— | O | $C_2H_5$— | 3 |
| p-$CH_3NHSO_2C_6H_4$— | H— | O | $C_2H_5$— | 1 |
| p-$(CH_3)_2NSO_2C_6H_4$— | H— | O | $C_2H_5$— | 3 |
| m-$(CH_3)_2NSO_2C_6H_4$— | H— | O | $C_2H_5$— | 1 |
| 3,5-$[(CH_3)_2NSO_2]_2C_6H_3$— | H— | O | $C_2H_5$— | 1 |
| 3-$(CH_3)_2NSO_2$—4-Cl—$C_6H_3$— | H— | O | $C_2H_5$— | 1 |
| 3-$(CH_3)_2NSO_2$—4-Br—$C_6H_3$— | H— | O | $C_2H_5$— | 1 |
| 2-F—5-$ClC_6H_3$— | H— | O | $C_2H_5$— | 3 |
| 3,5-$(H_2NSO_2)_2C_6H_3$— | H— | O | $C_2H_5$— | 3 |
| m-$CH_3COC_6H_4$— | H— | O | $C_2H_5$— | 3 |
| o-$FC_6H_4$— | H— | O | $C_2H_5$— | 3 |
| 3-CN—5-$BrC_6H_3$— | H— | O | $C_2H_5$— | 1 |
| 3,5-$(CN)_2C_6H_3$— | H— | O | $C_2H_5$— | 1 |
| 3-CN—5-$ClC_6H_3$— | H— | O | $C_2H_5$— | 1 |
| 3,5-$(CH_3O_2)_2C_6H_3$— | H— | O | $C_2H_5$— | 1 |
| 3,5-$Br_2C_6H_3$— | H— | O | $C_2H_5$— | 1 |
| 3,5-$(CF_3)_2C_6H_3$— | H— | O | $C_2H_5$— | 1 |
| 3,5-$Cl_2C_6H_3$— | H— | O | $C_2H_5$— | 1 |
| p-$ClC_6H_4CH_2$— | H— | O | $C_2H_5$— | 3 |
| 3,4-$Cl_2C_6H_3$— | H— | O | $C_2H_5$— | 1 |
| 3,5-$Br_2C_6H_3$— | H— | O | $C_2H_5$— | 1 |
| 3,5-$(CF_3)_2C_6H_3$— | H— | O | $C_2H_5$— | 1 |
| 3,5-$Cl_2C_6H_3$— | H— | O | $C_2H_5$— | 1 |
| p-$ClC_6H_4CH_2$— | H— | O | $C_2H_5$— | 3 |
| m-$(CH_3)_2NC_6H_4$— | $CH_3$— | O | $C_2H_5$— | 1 |
| p-$(CH_3)_2NC_6H_4$— | $CH_3$— | O | $C_2H_5$— | 1 |
| m-$\phi C_6H_4$— | $CH_3$— | O | $C_2H_5$— | 1 |
| m-$NCC_6H_4$— | n-$C_3H_7$—O | $C_2H_5$— | 1 |
| o-$HOC_6H_4$— | H— | O | $CH_3$— | 3 |
| p-$CH_3CONHC_6H_4$— | $CH_3$— | S | $CH_3$— | 4a |
| p-$C_2H_5CONHC_6H_4$— | H— | S | $CH_3$— | 4a |
| p-$CH_3SC_6H_4$— | $C_2H_5$— | O | $C_2H_5$— | 1 |
| p-$CH_3SO_2C_6H_4$— | $C_2H_5$— | O | $C_2H_5$— | 1 |
| 3,5-$Cl_2C_6H_3$— | $CH_3$— | O | $C_2H_5$— | 1 |
| 3,5-$F_2C_6H_3$— | $C_2H_5$— | O | $C_2H_5$— | 1 |
| 2-F—5-$ClC_6H_3$— | n-$C_3H_7$—O | $C_2H_5$— | 1 |
| 3-NC—5-$BrC_6H_3$— | $CH_3$— | O | $C_2H_5$— | 1 |
| 3,5-$(CH_3S)_2C_6H_3$— | $CH_3$— | O | $C_2H_5$— | 1 |
| 3,5-$Br_2C_6H_3$— | $CH_3$— | O | $C_2H_5$— | 1 |
| 3-$CH_3S$—4-$CH_3OC_6H_3$— | $CH_3$— | O | $C_2H_5$— | 1 |
| 3,4-$Cl_2C_6H_3$— | H— | O | $C_2H_5$— | 1 |
| 3,5-$(CF_3)_2C_6H_3$— | $CH_3$— | O | $C_2H_5$— | 1 |
| 3,4-$F_2C_6H_3$— | $CH_3$— | O | $C_2H_5$— | 1 |
| 3,4-$(CH_3O)_2C_6H_3$— | $C_2H_5$— | O | $C_2H_5$— | 1 |
| 3,4-$(CH_3O)_2C_6H_3$— | H— | O | $C_2H_5$— | 1 |
| 3-Cl—4-$BrC_6H_3$— | $CH_3$— | O | $C_2H_5$— | 1 |
| 3,5-$Br_2C_6H_3$— | $C_2H_5$— | O | $C_2H_5$— | 1 |
| 3-$(CH_3)_2NSO_2$—4-Cl—$C_6H_3$— | $CH_3$— | O | $C_2H_5$— | 1 |
| 3,5-$(i-C_3H_7O)C_6H_3$— | $CH_3$— | O | $C_2H_5$— | 1 |
| 3,5-$(C_2H_5O_2C)_2C_6H_3$— | $CH_3$— | O | $C_2H_5$— | 1 |
| 2-Cl—6-$FC_6H_3$— | H— | O | $C_2H_5$— | 1 |
| 3-$NO_2$—4-$HOC_6H_3$— | H— | O | $C_2H_5$— | 3 |
| 3-thienyl | H— | O | $C_2H_5$— | 1 |
| 3-furyl | H— | O | $C_2H_5$— | 1 |
| 5-isothiazolyl | H— | S | $C_2H_5$— | 4a |

| Q | R₂ | W | P | Preparation I |
|---|---|---|---|---|
| 4-(1,2,3-thiadiazolyl) | H— | S | C₂H₅— | 4a |
| 4-isothiazolyl | H— | S | C₂H₅— | 4a |
| 5-bromo-3-thienyl | H— | O | C₂H₅— | 1 |
| 5-bromo-3-furyl | H— | O | C₂H₅— | 1 |
| 5-bromo-2-furyl | H— | O | C₂H₅— | 1 |
| 5-bromo-2-thienyl | H— | O | C₂H₅— | 1 |
| 5-methyl-2-thienyl | H— | O | C₂H₅— | 1 |
| 2-methyl-4-thiazolyl | H— | S | C₂H₅— | 4a |
| 3-methyl-4-isoxazolyl | H— | S | C₂H₅— | 4a |
| 3-methyl-5-isoxazolyl | H— | S | C₂H₅— | 4a |
| 4-methyl-2-thienyl | H— | O | C₂H₅— | 1 |
| 5-chloro-2-thienyl | H— | O | C₂H₅— | 1 |
| 4-methoxy-2-thienyl | H— | O | C₂H₅— | 1 |
| 4-methoxy-5-bromo-2-thienyl | H— | O | C₂H₅— | 1 |
| 4-bromo-5-methyl-2-thienyl | H— | O | C₂H₅— | 1 |
| 4-methyl-5-bromo-2-thienyl | H— | O | C₂H₅— | 1 |
| 4-methyl-5-chloro-2-thienyl | H— | O | C₂H₅— | 1 |
| 4-methoxy-5-chloro-2-thienyl | H— | O | C₂H₅— | 1 |
| 4,5-dichloro-2-thienyl | H— | O | C₂H₅— | 1 |
| 5-diethylsulfamoyl-2-thienyl | H— | O | C₂H₅— | 1 |
| 2-benzofuryl | H— | O | C₂H₅— | 1 |
| 4-methoxy-5-diethylsulfamoyl-2-thienyl | H— | O | C₂H₅— | 1 |
| 2-benzothienyl | H— | O | C₂H₅— | 1 |
| 2-methyl-5-benzofuryl | H— | O | C₂H₅— | 1 |
| 2-thienyl | H— | O | C₂H₅— | 3 |
| 2-benzothiazolyl | H— | O | CH₃— | 2 |
| 2-benzoxazolyl | H— | O | CH₃— | 2 |
| 3-(1,2,4-oxadiazolyl) | H— | O | C₂H₅— | 3 |
| 4,5-dibromo-2-furyl | H— | O | C₂H₅— | 1 |
| 2-benzo-γ-pyrone | H— | O | C₂H₅— | 1 |
| 4-chloro-2-thienyl | H— | O | C₂H₅— | 1 |
| 4-sulfamoyl-2-thienyl | H— | O | C₂H₅— | 1 |
| 4-ethylsulfamoyl-5-chloro-2-thienyl | H— | O | C₂H₅— | 1 |
| 4-sulfamoyl-5-chloro-2-thienyl | H— | O | CH₃— | 3 |
| 4-diethylsulfamoyl-5-chloro-2-thienyl | H— | O | C₂H₅— | 1 |
| 4-bromo-2-thienyl | H— | O | C₂H₅— | 1 |
| 4,5-dibromo-2-thienyl | H— | O | C₂H₅— | 1 |
| 2-thienyl | H— | O | CH₃— | 3 |
| 2-furyl | H— | O | C₂H₅— | 1 |
| 4-methyl-5-bromo-2-furyl | H— | O | C₂H₅— | 1 |
| 4-methyl-2-thiazolyl | H— | O | CH₃— | 2 |
| 5-chloro-3-sulfamoyl-2-thienyl | H— | O | CH₃— | 3 |
| 3-thenyl | H— | O | CH₃— | 3 |
| 3-pyridyl | H— | O | CH₃— | 2 |
| 4-pyridyl | H— | O | CH₃— | 2 |
| 4-pyridyl-N-oxide | H— | O | CH₃— | 2 |
| 5-chloro-3-pyridyl | H— | O | C₂H₅— | 2 |
| 5-bromo-3-pyridyl | H— | O | C₂H₅— | 2 |
| 5-fluoro-3-pyridyl | H— | O | C₂H₅— | 3 |
| 3-picolyl | H— | | | |
| 4-pyridazinyl | H— | O | CH₃— | 2 |
| 3-pyridazinyl | H— | O | CH₃— | 2 |
| 2-pyrazinyl | H— | O | C₂H₅— | 3 |
| 6-chloro-2-pyrazinyl | H— | O | C₂H₅— | 3 |
| 2-pyrimidinyl | H— | O | CH₃— | 2 |
| 5-pyrimidinyl | H— | O | CH₃— | 2 |
| 2,6-dichloro-4-pyridyl | H— | O | C₂H₅— | 1 |
| 2-benzimidazolyl | H— | S | C₂H₅— | 4 |
| 2-methyl-5-benzimidazolyl | H— | O | C₂H₅— | 3 |
| 2-quinoxalinyl | H— | O | C₂H₅— | 3 |
| 6-quinoxalinyl | H— | O | C₂H₅— | 3 |
| 4-imidazolyl | H— | S | C₂H₅— | 4 |
| 5-chloro-2-benzimidazolyl | H— | S | C₂H₅— | 4 |
| 5-bromo-2-benzimidazolyl | H— | S | C₂H₅— | 4 |
| 4-isoquinolinyl | H— | O | CH₃— | 3 |
| 3-quinolinyl | H— | O | CH₃— | 3 |
| 4-quinolinyl | H— | O | CH₃— | 3 |
| 6-quinolinyl | H— | O | C₂H₅— | 3 |
| 2-pyrryl | H— | O | C₂H₅— | 2 |
| 3-pyrryl | H— | O | C₂H₅— | 2 |
| 2-chloro-4-pyridyl | H— | O | CH₃— | 2 |
| 3-pyridyl-N-oxide | H— | O | C₂H₅— | 2 |
| 2-fluoro-4-pyridyl | H— | O | CH₃— | 2 |
| 4-picolyl | H— | O | CH₃— | 2 |
| CH₃OCH₂— | H— | S | C₂H₅— | 4 |
| CH₃SCH₂— | H— | S | C₂H₅— | 4 |
| CH₃SO₂CH₂— | H— | O | C₂H₅— | 3 |
| CH₃SOCH₂— | H— | S | C₂H₅— | 4 |
| C₆H₅CH₂SCH₂— | H— | S | C₂H₅— | 4 |
| p-CH₃OC₆H₄SCH₂— | H— | S | C₂H₅— | 4 |
| p-CH₃C₆H₄SCH₂— | H— | S | C₂H₅— | 4 |
| p-ClC₆H₄SCH₂— | H— | S | C₂H₅— | 4 |
| p-BrC₆H₄SCH₂— | H— | S | C₂H₅— | 4 |
| 3,5-Cl₂C₆H₃OCH₂— | H— | S | C₂H₅— | 4 |
| p-ClC₆H₄OCH₂— | H— | S | C₂H₅— | 4 |
| 3,4-Cl₂C₆H₃OCH₂— | H— | S | C₂H₅— | 4 |
| ClCH₂— | H— | O | C₂H₅— | 3 |
| HOCH₂— | H— | O | C₂H₅— | 3 |
| FCH₂— | H— | O | C₂H₅— | 3 |
| CH₃NHCH₂— | H— | S | C₂H₅— | 4 |
| CH₃CONHCH₂— | H— | S | C₂H₅— | 4 |
| C₆H₅CONHCH₂— | H— | S | C₂H₅— | 4 |
| p-ClC₆H₄CONHCH₂— | H— | S | C₂H₅— | 4 |
| 3,4-Cl₂C₆H₃CONHCH₂— | H— | S | C₂H₅— | 4 |
| C₆H₅SO₂NHCH₂— | H— | O | C₂H₅— | 3 |
| C₆H₅CH₂O₂CNHCH₂— | H— | O | C₂H₅— | 3 |
| C₆H₅CO₂CH₂— | H— | S | C₂H₅— | 4 |
| 2-thienyl-CONHCH₂— | H— | S | C₂H₅— | 4 |
| p-ClC₆H₄NHCH₂— | H— | S | CH₃— | 4a |
| 3,4-Cl₂C₆H₃NHCH₂— | H— | S | CH₃— | 4a |
| C₆H₅CH₂O₂CNHCH₂CONHCH₂— | H— | O | C₂H₅— | 3 |
| n-C₃H₇SCH₂— | H— | S | C₂H₅— | 4 |
| i-C₃H₇OCH₂— | H— | O | C₂H₅— | 3 |
| m-ClC₆H₄SCH₂— | H— | S | C₂H₅— | 4 |
| n-C₃H₇SO₂CH₂— | H— | O | C₂H₅— | 3 |
| n-C₃H₇NHCH₂— | H— | S | C₂H₅— | 4 |
| C₂H₅SCH₂— | H— | S | C₂H₅— | 4 |
| C₂H₅NHCH₂— | H— | S | C₂H₅— | 4 |
| CH₃CH₂CONHCH₂— | H— | S | C₂H₅— | 4 |
| m-BrC₆H₄SCH₂— | H— | S | C₂H₅— | 4 |
| m-ClC₆H₄OCH₂— | H— | O | C₂H₅— | 3 |
| o-CH₃C₆H₄SCH₂— | H— | S | C₂H₅— | 4 |
| m-CH₃OC₆H₄SCH₂— | H— | S | C₂H₅— | 4 |
| CH₃(CH₃)₂CONHCH₂— | H— | S | C₂H₅— | 4 |
| m-ClC₆H₄CONHCH₂— | H— | S | C₂H₅— | 4 |
| o-FC₆H₄SCH₂— | H— | S | C₂H₅— | 4 |
| 3,5-Cl₂C₆H₃CONHCH₂— | H— | S | C₂H₅— | 4 |
| 3,5-Cl₂C₆H₃SCH₂— | H— | S | C₂H₅— | 4 |
| C₆H₅CH₂— | H— | O | C₂H₅— | 3 |
| C₂H₅CH(OH)— | H— | O | C₂H₅— | 3 |
| C₆H₅C(OH)(C₂H₅)— | H— | O | C₂H₅— | 3 |
| i-C₃H₇CH(OH)— | H— | O | C₂H₅— | 3 |
| C₆H₅C(OH)(n-C₃H₇)— | H— | O | C₂H₅— | 3 |
| (C₂H₅)₂C(OH)— | H— | O | C₂H₅— | 3 |
| CH₃CH(OH)— | H— | O | C₂H₅— | 3 |
| CH₃C(OH)(C₂H₅)— | H— | O | C₂H₅— | 3 |
| C₆H₅C(OH)(CH₃)— | H— | O | C₂H₅— | 3 |
| 5-chloro-2-benzothienyl | H— | O | C₂H₅— | 1 |
| 4-chloro-2-benzothienyl | H— | O | C₂H₅— | 1 |
| 6-chloro-2-benzo- | H— | O | C₂H₅— | 1 |

-continued

| | W—P | | | |
| | Q—C=N—R₂ | | | |
| Q | R₂ | W | P | Preparation I |
| thienyl | | | | |
| 5-fluoro-2-benzo-thienyl | H— | O | $C_2H_5$— | I |
| 5-bromo-2-benzo-thienyl | H— | O | $C_2H_5$— | I |

PREPARATION J

Nitriles

The nitriles utilized as intermediates in the preparation of the imino ethers or thioethers are either known compounds or are synthesized by methods familiar to one skilled in the art as taught by Wagner and Zook, "Synthetic Organic Chemistry," John Wiley & Sons, Inc., New York, N.Y., 1953, Chapt. 20, p. 590.

PREPARATION K

Amides

The amides employed in the synthesis of the imino ethers used as intermediates are reported in the literature or are prepared by one or more of the well-known methods as taught by Wagner and Zook, "Synthetic Organic Chemistry," John Wiley & Sons, Inc., New York, N.Y., 1953, Chapt. 19, p. 565.

What is claimed is:

1. A compound selected from those of the formula

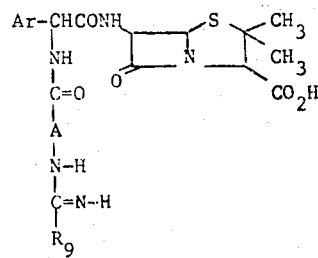

and the pharmaceutically acceptable basic salts or acid addition salts thereof, wherein Ar is selected from the group consisting of phenyl, 4-hydroxyphenyl, 2-thienyl and 3-thienyl;

A is methylene and $R_9$ is selected from the group consisting of pyridyl; pyrimidinyl; pyridazinyl; pyrazinyl; benzimidazolyl; pyrryl; 2-pyrrolinyl; picolyl; substituted pyridyl wherein said substituent is selected from the group consisting of fluoro, chloro, bromo and 2,6-dichloro; and pyridyl-1-oxide.

2. A compound of claim 1 wherein Ar is phenyl and A is —$CH_2$—.

3. The compound of claim 2 wherein $R_9$ is 4-pyridyl.

4. The compound of claim 2 wherein $R_9$ is 3-pyridyl.

5. The compound of claim 2 wherein $R_9$ is 4-pyridyl-N-oxide.

6. The compound of claim 2 wherein $R_9$ is 2,6-dichloro-4-pyridyl.

7. The compound of claim 2 wherein $R_9$ is 2-benzimidazolyl.

8. The compound of claim 2 wherein $R_9$ is 2-pyrryl.

* * * * *